United States Patent
Hans et al.

(10) Patent No.: US 8,293,511 B2
(45) Date of Patent: Oct. 23, 2012

(54) PRODUCTION OF β-LACTAM ANTIBIOTICS

(75) Inventors: Marcus Hans, Den Haag (NL); Roelof Ary Lans Bovenberg, Rotterdam (NL); Paul Klaassen, Dordrecht (NL); Rémon Boer, Dordrecht (NL); Jan Metske Van Der Laan, Breda (NL)

(73) Assignee: DSM IP Assets B.V., Heerlen (NL)

( * ) Notice: Subject to any disclaimer, the term of this patent is extended or adjusted under 35 U.S.C. 154(b) by 621 days.

(21) Appl. No.: 12/444,108

(22) PCT Filed: Oct. 2, 2007

(86) PCT No.: PCT/EP2007/060460
§ 371 (c)(1),
(2), (4) Date: May 8, 2009

(87) PCT Pub. No.: WO2008/040731
PCT Pub. Date: Apr. 10, 2008

(65) Prior Publication Data
US 2010/0009404 A1    Jan. 14, 2010

(30) Foreign Application Priority Data

Oct. 5, 2006  (EP) .................................. 06121817
Jul. 25, 2007  (EP) .................................. 07113095

(51) Int. Cl.
*C12N 9/00* (2006.01)
*C12P 37/00* (2006.01)
(52) U.S. Cl. .......................................... 435/183; 435/43
(58) Field of Classification Search .................... 435/43, 435/183
See application file for complete search history.

(56) References Cited

U.S. PATENT DOCUMENTS

2003/0088058 A1  5/2003  Schofield et al.
2004/0087000 A1  5/2004  Schofield et al.

FOREIGN PATENT DOCUMENTS

WO    98/16648    4/1998

OTHER PUBLICATIONS

Written Opinion (IPER) (Apr. 2005) for PCT/EP2007/60460, pp. 1-7.*
Sequence Alignment Between AC P27743 & SEQ ID No. 10, (1991).*
Barends et al. "Three-dimensional structures of enzymes useful for beta-lactam antibiotic production" Current Opinion in Biotechnology, vol. 15, No. 4, pp. 356-363 (Aug. 2004).
International Search Report for PCT/EP2007/060460, mailed Apr. 9, 2008.
Huffman et al. "Substrate specificity of isopenicillin N syntase" Journal of Medicinal Chemistry, vol. 35, No. 10, pp. 1897-1914 (1992).
Luengo et al. "Direct enzymatic synthesis of penicillin G using cyclases of *Penicillium chrysogenum* and *Acremonium chrysogenum*" Bio/Technology, vol. 4, No. 1, pp. 44-47 (1986).

* cited by examiner

*Primary Examiner* — Tekchand Saidha
(74) *Attorney, Agent, or Firm* — Nixon & Vanderhye P.C.

(57) ABSTRACT

The present invention describes a process for the production of an N-α-amino-hydroxyphenylacetyl or an N-α-aminophenylacetyl β-lactam antibiotic comprising an IPNS-catalysed conversion of a precursor tripeptide hydroxyphenylglycyl-cysteinyl-valine (HpgCV) or phenylglycyl-cysteinyl-valine (PgCV), respectively, to the N-hydroxyphenylglycyl or the N-phenylglycyl β-lactam antibiotic, respectively. The tripeptide HpgCV or the tripeptide PgCV may further be prepared by contacting the amino acids hydroxyphenylglycine (Hpg) or phenylglycine (Pg), cystein (C) and valine (V) with a non-ribosomal peptide synthetase (NRPS) to effect formation of the tripeptide HpgCV or the tripeptide PgCV, the NRPS comprising a first module M1 specific for Hpg or Pg, a second module M2 specific for C and a third module M3 specific for V An IPNS is further provided having an improved activity in this conversion, as well as an NRPS catalysing the formation of the tripeptides. Also a host cell is provided capable of fermentatively producing β-lactam antibiotics with N-α-amino-hydroxyphenylacetyl or an N-α-aminophenylacetyl side chains.

8 Claims, No Drawings

SEQUENCE LISTING

<160> NUMBER OF SEQ ID NOS: 37

<210> SEQ ID NO 1
<211> LENGTH: 331
<212> TYPE: PRT
<213> ORGANISM: Emericella nidulans

<400> SEQUENCE: 1

```
Met Gly Ser Val Ser Lys Ala Asn Val Pro Lys Ile Asp Val Ser Pro
1               5                   10                  15

Leu Phe Gly Asp Asp Gln Ala Ala Lys Met Arg Val Ala Gln Gln Ile
            20                  25                  30

Asp Ala Ala Ser Arg Asp Thr Gly Phe Phe Tyr Ala Val Asn His Gly
        35                  40                  45

Ile Asn Val Gln Arg Leu Ser Gln Lys Thr Lys Glu Phe His Met Ser
    50                  55                  60
```

```
Ile Thr Pro Glu Glu Lys Trp Asp Leu Ala Ile Arg Ala Tyr Asn Lys
 65                  70                  75                  80

Glu His Gln Asp Gln Val Arg Ala Gly Tyr Tyr Leu Ser Ile Pro Gly
                 85                  90                  95

Lys Lys Ala Val Glu Ser Phe Cys Tyr Leu Asn Pro Asn Phe Thr Pro
            100                 105                 110

Asp His Pro Arg Ile Gln Ala Lys Thr Pro Thr His Glu Val Asn Val
            115                 120                 125

Trp Pro Asp Glu Thr Lys His Pro Gly Phe Gln Asp Phe Ala Glu Gln
130                 135                 140

Tyr Tyr Trp Asp Val Phe Gly Leu Ser Ser Ala Leu Leu Lys Gly Tyr
145                 150                 155                 160

Ala Leu Ala Leu Gly Lys Glu Glu Asn Phe Phe Ala Arg His Phe Lys
                165                 170                 175

Pro Asp Asp Thr Leu Ala Ser Val Val Leu Ile Arg Tyr Pro Tyr Leu
            180                 185                 190

Asp Pro Tyr Pro Glu Ala Ala Ile Lys Thr Ala Ala Asp Gly Thr Lys
            195                 200                 205

Leu Ser Phe Glu Trp His Glu Asp Val Ser Leu Ile Thr Val Leu Tyr
210                 215                 220

Gln Ser Asn Val Gln Asn Leu Gln Val Glu Thr Ala Ala Gly Tyr Gln
225                 230                 235                 240

Asp Ile Glu Ala Asp Asp Thr Gly Tyr Leu Ile Asn Cys Gly Ser Tyr
                245                 250                 255

Met Ala His Leu Thr Asn Asn Tyr Tyr Lys Ala Pro Ile His Arg Val
            260                 265                 270

Lys Trp Val Asn Ala Glu Arg Gln Ser Leu Pro Phe Phe Val Asn Leu
            275                 280                 285

Gly Tyr Asp Ser Val Ile Asp Pro Phe Asp Pro Arg Glu Pro Asn Gly
            290                 295                 300

Lys Ser Asp Arg Glu Pro Leu Ser Tyr Gly Asp Tyr Leu Gln Asn Gly
305                 310                 315                 320

Leu Val Ser Leu Ile Asn Lys Asn Gly Gln Thr
                325                 330

<210> SEQ ID NO 2
<211> LENGTH: 1106
<212> TYPE: PRT
<213> ORGANISM: Streptomyces coelicolor

<400> SEQUENCE: 2

Met Ala Thr Leu Pro Glu Leu Phe Ala Glu Gln Ala Leu Arg Thr Pro
  1               5                  10                  15

Gly Ala Pro Ala Leu Val Arg Gly Gly Thr Thr Val Ser Tyr Ala Glu
                 20                  25                  30

Leu Asp Leu Arg Thr Asn Arg Leu Ala Arg Leu Arg Gln Gln Gly
             35                  40                  45

Val Arg Pro Gly Thr Pro Val Val Met Leu Met Glu Arg Ser Pro Ala
 50                  55                  60

His Val Val Ala Thr Leu Ala Ile Ala Lys Ala Gly Gly Ala Tyr Val
 65                  70                  75                  80

Pro Leu His Asp Thr Tyr Pro Leu Asp Arg Met Arg His Val Val Ala
                 85                  90                  95

Asp Thr Ala Thr Leu Ile Leu Thr Asp Arg Ala Glu Ala Ala Arg
            100                 105                 110
```

```
Ala Gly Gln Leu Gly Ala Arg Val Met Val Val Asp Glu Phe Gly Ala
            115                 120                 125
Ala Pro Ser Gly Ser Glu Ala Asp Ala Ala Pro Thr Gly Thr Gly
        130                 135                 140
Thr Gly Thr Gly Ser Arg Ser Gly Tyr Val Asp Asp Ala Pro Glu Val
145                 150                 155                 160
Gly Leu Arg Pro Gln Asp Leu Ala Tyr Val Met Tyr Thr Ser Gly Ser
                165                 170                 175
Thr Gly Val Pro Lys Gly Val Ala Val Thr His Arg Gly Val Val Asp
            180                 185                 190
Leu Val Arg Asp His Cys Trp Arg Pro Gly Val His Glu Arg Val Leu
        195                 200                 205
Leu His Ala Pro His Ala Phe Asp Val Ser Cys Tyr Glu Met Trp Val
    210                 215                 220
Pro Leu Val Ser Gly Gly Thr Val Val Ala Pro Pro Gly His Leu
225                 230                 235                 240
Asp Pro Ala Ala Ile Thr Asp Leu Ile Thr Ala His Asp Ile Thr Ala
                245                 250                 255
Ile His Leu Thr Ala Gly Phe Phe Arg Val Val Ala Glu Glu Ala Pro
            260                 265                 270
Glu Cys Phe Ala Gly Val Arg Glu Val Leu Thr Gly Gly Asp Val Val
        275                 280                 285
Ser Pro Ala Val Ala Arg Val Leu Ala His His Pro Arg Ile Val
290                 295                 300
Leu Arg His Leu Tyr Gly Pro Thr Glu Thr Thr Leu Cys Val Thr Gln
305                 310                 315                 320
His Glu Val Thr Ala Pro Tyr Glu Ala Arg Gly Ser Leu Pro Val Gly
                325                 330                 335
Arg Ala Thr Gly Asn Thr Arg Ala Tyr Val Leu Asp Arg Tyr Leu Gln
            340                 345                 350
Pro Val Pro Ala Gly Val Pro Gly Glu Leu Phe Ile Ser Gly Ser Gly
        355                 360                 365
Leu Ala Arg Gly Tyr Leu Asp Arg Pro Asp Leu Thr Cys Glu Arg Phe
    370                 375                 380
Val Ala Asp Pro Tyr Gly Gly Ser Gly Glu Arg Met Tyr Arg Thr Gly
385                 390                 395                 400
Asp Leu Val Arg Tyr Asn Ala Ala Gly Glu Leu Glu Tyr Leu Ala Arg
                405                 410                 415
Ala Asp Asp Gln Val Lys Ile Arg Gly Phe Arg Val Glu Leu Gly Glu
            420                 425                 430
Ile Glu Ala Val Leu Ala Thr Arg Pro Glu Leu Ala Gln Ala Ala Val
        435                 440                 445
Val Val Arg Glu Asp Arg Pro Gly Asp Arg Arg Leu Val Gly Tyr Val
    450                 455                 460
Val Ala Ala Ala Gly Arg Asp Gly Glu Val Asp Pro Asp Ala Leu Arg
465                 470                 475                 480
Ala Phe Ser Arg Gln Ala Leu Pro Asp Tyr Met Val Pro Ser Ala Phe
                485                 490                 495
Val Val Leu Gly Thr Leu Pro Leu Thr Ala Asn Gly Lys Leu Asp Arg
            500                 505                 510
Lys Ala Leu Pro Ala Pro Asp Tyr Gly Ala Ala Ser Thr Gly Arg Ala
        515                 520                 525
Ala Arg Thr Pro Ala Glu Glu Leu Leu Cys Thr Leu Phe Ala Gln Val
    530                 535                 540
```

```
Leu Gly Leu Ser Ala Val Gly Val Asp Asp Gly Phe Phe Asp Leu Gly
545                 550                 555                 560

Gly Asp Ser Ile Leu Ser Ile Gln Leu Val Ser Arg Ala Arg Ala Ala
                565                 570                 575

Gly Leu Ala Leu Ala Val Arg Asp Val Phe Glu His Gln Ser Thr Ala
                580                 585                 590

Arg Leu Ala Ala Ala Leu Thr Asp Arg Asp Asp Ala Ala Ser Val Pro
                595                 600                 605

Glu Ala Glu Ala Val Pro Pro Tyr Gly Pro Ala Pro Leu Thr Pro Val
610                 615                 620

Met Ala Arg Ile Ala Glu Leu Gly Leu Gly Gly Asp Asp Phe Asn Gln
625                 630                 635                 640

Ser Val Val Val Ser Leu Pro Pro Ala Val Asp Arg Asp Arg Leu Val
                645                 650                 655

Pro Ala Leu Gln Arg Val Leu Asp His His Asp Ala Leu Arg Leu Arg
                660                 665                 670

Val Leu Pro Asp Gly Ser Thr Glu Val Arg Ala Pro Gly Ser Val Pro
                675                 680                 685

Ala Ala Asp Val Leu Ser Val Val Thr Arg Ala Pro Gly Ala Thr Gly
690                 695                 700

Glu Ala Arg Asp Ala Leu Leu Val Glu Ala Ala Cys Ala Ala Arg Asp
705                 710                 715                 720

Arg Leu Ala Pro Ala Glu Gly Arg Met Leu Gln Ala Val Leu Val Asp
                725                 730                 735

Gly Thr Asp Asp Thr Asp Gly Thr Gly Gly Thr Ser Gly Ala Asp Gly
                740                 745                 750

Val Leu Ile Leu Val Ala His His Leu Val Val Asp Ser Val Thr Trp
                755                 760                 765

Ser Ile Val Val Pro Asp Leu Ala Ala Ala Tyr Arg Gly Glu Glu Pro
770                 775                 780

Ala Pro Val Gly Thr Ser Trp Arg Gln Trp Ala Thr Ser Leu Ala Arg
785                 790                 795                 800

Leu Ala Thr Asp Pro Arg Val Glu Ala Glu Thr Ala His Trp Glu His
                805                 810                 815

Thr Leu Thr Gly Ala Gly Thr Leu Arg Leu Asp Arg Gly Arg Asp Leu
                820                 825                 830

Gln Gly Asp Ala Gly Arg Ile Ser Leu Asp Leu Ala Pro His Thr Thr
                835                 840                 845

Glu Ala Leu Leu Thr Arg Leu Pro Gly Gly Val Asn Ala Ser Val His
850                 855                 860

Asp Val Leu Leu Thr Ala Phe Ala Phe Ala Val Ala Gly Trp Arg Arg
865                 870                 875                 880

Gly Arg Gly Glu Asp Pro Asp Ala Pro Val Val Leu Asp Leu Glu Ser
                885                 890                 895

His Gly Arg His Glu Glu Ala Val Pro Gly Ala Glu Leu Ser Arg Thr
                900                 905                 910

Ala Gly Trp Phe Thr Ala Leu His Pro Val Arg Leu Ala Pro Asp Val
                915                 920                 925

Thr Asp Trp Ala Arg Leu His Gln Asp Gly Asp Ala Leu Arg Asp Gly
                930                 935                 940

Leu Lys Gln Val Lys Glu Gln Leu Arg Ser Val Pro Gly Asp Gly Leu
945                 950                 955                 960

Gly His Gly Leu Leu Arg His Leu Asn Pro Thr Ala Gly Pro Arg Leu
```

```
              965                 970                975
Ala Arg Leu Pro Glu Pro Asp Phe Gly Phe Asn Tyr Leu Gly Arg Arg
                980                 985                990

Val Thr Pro Ala Thr Gly Thr Pro Glu Pro Trp Thr Val Thr Gly Gly
        995                1000               1005

Gly Leu Ala Ala Ser Arg Pro Thr Ala Pro Met Ala His Ala Val
    1010                1015                1020

Glu Leu Ser Ala Val Val His Glu Gly Ala Asp Gly Pro Arg Leu
    1025                1030                1035

Arg Ala Glu Trp Thr Tyr Ala Arg Arg Leu Val Pro Asp His Asp
    1040                1045                1050

Ala Arg Arg Leu Ala Glu Gln Trp Phe Arg Ala Leu Glu Ala Leu
    1055                1060                1065

Val Glu Gln Ala Asp Arg Ala Gly Thr Gly Gly Leu Thr Pro Ser
    1070                1075                1080

Asp Val Thr Leu Gly Ser Leu Ser Gln Ser Glu Ile Glu Glu Phe
    1085                1090                1095

Glu Ser Asp Leu Glu Ser Glu Trp
    1100                1105

<210> SEQ ID NO 3
<211> LENGTH: 3318
<212> TYPE: DNA
<213> ORGANISM: Streptomyces coelicolor

<400> SEQUENCE: 3
atggcgacgc tgccggaact gttcgcggag caggcgctcc ggacgcccgg ggcaccggcg      60
ctggtgcggg gcgggacgac ggtgtcgtac gccgaactcg acctgcgcac caaccggctg     120
gcccggctgc tgcggcagca gggggtgcgg ccgggcacgc cggtggtcat gctgatggag     180
cggtcgcccg cccatgtcgt ggcgacgctg gccatcgcca aggcgggcgg cgcctacgtg     240
cccctgcacg acacgtatcc cctcgaccgg atgcggcacg tggtggcgga caccgccgcg     300
acgctgatcc tcaccgaccg ggcgaggcg gcgcgggccg gcagctcgg cgcgcgggtg       360
atggtggtcg acgagttcgg cgccgccccg tccggctcgg aggccgacgc ggccccggc      420
accggcaccg gcaccggcac cggctcgcgc tccgggtacg tcgacgatgc tccggaggtg     480
ggcctgcgcc cgcaggatct cgcgtacgtg atgtacacct ccgggtccac cggggtgccg     540
aagggcgtcg cggtcaccca cgcggggtc gtggacctgg tccgcgacca ctgctggcgg      600
ccgggcgtcc acgagcgggt gctgctgcac gccccgcacg cgttcgacgt gtcctgctac     660
gagatgtggg tgccctggt ctcgggcgga acggtcgtcg tggcaccgcc cggacacctg      720
gacccggccg cgatcaccga cctgatcacc gctcacgaca tcaccgcgat ccacctcacc     780
gcgggcttct tccgggtcgt cgcggaggag gcaccggagt gcttcgccgg tgtgcgggag     840
gtgctgaccg gcgcgacgt ggtctcgcca gccgcgtgg cccgggtcct cgcgcaccac       900
ccgcggatcg tactgcgtca cctgtacggg ccgaccgaga cgacgctgtg cgtgacgcag     960
cacgaggtca ccgcgccgta cgaggcccgc ggcagcctgc cggtcgggcg ggcgacgggg    1020
aacacccggg cctacgtgct cgaccggtac ctccagccgg tgccggccgg cgtgccgggc    1080
gagctgttca tctccggctc cggtctggcg cgcggctacc tggaccgtcc gacctgacc     1140
tgtgagcggt tcgtcgccga tccgtacggc gggtccggcg agcggatgta ccgcacgggc    1200
gacctggtcc gctacaacgc ggcgggcgaa ctggagtacc tggcccgcgc cgacgaccag    1260
gtcaagatcc gcggcttccg ggtggaactg ggcgagatcg aggcggtcct ggccacgcgc    1320
```

```
ccggagctgg cccaggccgc cgtcgtcgtc cgcgaggacc ggcccggcga ccggcgcctg    1380
gtcggctacg tggtggccgc ggcgggccgg gacggcgagg tcgacccgga cgcgctgcgc    1440
gccttctccc gccaggcgct gccggactac atggtgccgt cggcgttcgt ggtcctcggc    1500
accctgccgc tgaccgccaa cggcaaactg gaccgcaagg cgctgcccgc gcccgactac    1560
ggggcggcgt ccaccgggcg gccgcccgc accccctgccg aggagctgct gtgcacgctc    1620
ttcgcccagg tgctcggcct gtccgcggtg ggcgtcgacg acgggttctt cgatctgggc    1680
ggcgacagca tcctgtccat ccagctcgtc agccgggccc cgccgccgg actcgccctc    1740
gccgtccgcg acgtcttcga gcaccagtcg acggcccggc tggccgccgc gctgacggac    1800
cgggacgacg cggcctccgt gccggaggcc gaagcggtgc cgccgtacgg tcccgccccg    1860
ctgaccccg tgatggcccg catcgccgaa ctgggcctgg gcgagacga cttcaaccag    1920
tcggtcgtgg tgtccctgcc gcccgcggtg gaccgggacc ggctcgtccc ggccctgcaa    1980
cgtgtgctcg accaccatga cgcgctgcgc ctgcgcgtcc tgcccgacgg gagcacggag    2040
gtacgcgccc cgggcagtgt ccggccgcg gacgtcctga gcgtcgtcac gcgggccccc    2100
ggcgccaccg cgcaggcgcg cgacgccctg ctcgtggagg cggcgtgcgc cgcacgggac    2160
cggctcgcac cggccgaggg ccgcatgctc caggcggtcc tggtcgacgg cacggacgac    2220
acggacggca cgggcgggac ctccggggcg gacgcgtgc tgatcctggt cgcccaccac    2280
ctggtggtcg actcggtgac gtggagcatc gtcgtaccgg acctcgccgc ggcctaccgg    2340
ggcgaggagc ccgcccgcggt gggcaccctg tggcggcagt gggccacctc cctggcacgg    2400
ctggccaccg accccgcgt cgaggcggag accgcccact gggagcacac gctcaccggg    2460
gcgggcaccc tgcggctgga ccgcggccgc gatctccagg gcgacgccgg acgcatcagc    2520
ctcgacctgg ccccgcacac gaccgaggcc ctgctcacgc gcctgccgg gggcgtcaac    2580
gcgagcgtgc acgacgtcct gctgaccgcc ttcgcgttcg ccgtcgccgg gtggcggcgc    2640
ggacgcggcg aggacccgga cgcgcccgtc gtgctcgacc tggagagcca cggccggcac    2700
gaggaggcgg tgccgggcgc cgaactcagc cgcacggcgg gctggttcac ggccctccac    2760
ccggtgcggc tggctccgga cgtcaccgac tgggcgcggc tgcaccagga cggcgacgcg    2820
ctccgggacg gcctcaagca ggtgaaggaa cagttgcggt ccgtaccggg cgacggcctc    2880
ggccacggct tgctgcgcca cctcaacccc accgctgggc cccgcctcgc acgccttccc    2940
gagcccgact tcggcttcaa ctacctgggc cgccgggtca ccccggccac cggcaccccg    3000
gaaccgtgga ccgtcacggg cggcggcctc gccgcctcgc ggcccacggc gccgatggcc    3060
cacgcggtgg agctgagcgc cgtcgtccac gaggggcgg acggccccg actgcgcgcg    3120
gagtggaccct acgcacgccg cctggtcccc gatcacgacg cccgccgcct ggccgagcaa    3180
tggttccggg cgctggaagc cctggtggag caggccgacc gggccggcac cggcggcctg    3240
accccgtccg acgtgaccct cggctcgctc agccagtccg agatcgagga attcgagtcc    3300
gaccttgagt ccgagtgg                                                 3318
```

<210> SEQ ID NO 4
<211> LENGTH: 1091
<212> TYPE: PRT
<213> ORGANISM: Artificial Sequence
<220> FEATURE:
<223> OTHER INFORMATION: Hybrid sequence

<400> SEQUENCE: 4

Met Ala Cys Leu Pro Arg Arg Ile Ala Glu Gln Ala Ala Arg Thr Pro

-continued

```
1               5                   10                  15
His Ala Val Ala Val Thr Glu Ala Gly Gly Thr Leu Ile Thr Tyr Ser
                20                  25                  30

Glu Leu Asp Ala Arg Ala Asn Arg Leu Ala Arg His Leu Ile Arg Arg
                35                  40                  45

Gly Val Thr Ala Glu Thr Arg Val Ala Val Leu Ala Glu Arg Ser Ala
                50                  55                  60

Gln Leu Val Val Thr Thr Leu Ala Ile Leu Lys Ala Gly Gly Val Tyr
 65                  70                  75                  80

Val Pro Leu His Thr Gly Tyr Pro Val Asp Arg Met Arg His Val Leu
                85                  90                  95

Ala Asp Thr Glu Ala Ala Leu Leu Leu Thr Asp Thr His His Ala Ala
                100                 105                 110

Thr Ala Ala Arg Leu Asp Thr Pro Ala Leu Thr Val Asp Glu Asp Thr
                115                 120                 125

Thr Ala Gly Glu Gln Asp Thr Thr Ala Pro Asp Val Thr Val Arg Pro
                130                 135                 140

Asp Gln Leu Ala Tyr Ile Met Phe Thr Ser Gly Ser Thr Gly Thr Pro
145                 150                 155                 160

Lys Gly Ile Gly Ile Thr His Arg Asp Ala Ile Ala Leu Ala Ala Asp
                165                 170                 175

Arg Cys Trp Asp Leu Asp Thr Gly Ser Arg Val Leu Met His Ser Pro
                180                 185                 190

Tyr Ala Phe Asp Ile Ser Thr Phe Glu Leu Phe Ala Pro Leu Leu Ala
                195                 200                 205

Gly Gly Arg Ile Val Val Ala Pro Arg Gly Asp Ile Asp Ala Ala Val
                210                 215                 220

Leu Gln Arg Thr Leu Ala Ala His Gly Val Thr Ser Leu Leu Leu Thr
225                 230                 235                 240

Ala Gly Leu Leu Gly Val Ile Ala Asp Glu Ala Pro Glu Val Phe Thr
                245                 250                 255

Gly Val Lys Asp Val Trp Thr Gly Gly Asp Val Val Ser Pro Thr Ala
                260                 265                 270

Val Arg Arg Val Leu Glu Ala Cys Pro Gly Thr Val Val Lys Thr Leu
                275                 280                 285

Tyr Gly Pro Thr Glu Thr Thr Leu Gly Cys Thr Trp Leu Pro Phe Thr
                290                 295                 300

Asp Pro Arg Arg Ile Pro Pro Ala Val Pro Ile Gly Arg Pro Leu Asp
305                 310                 315                 320

Asn Thr Arg Ala Tyr Val Leu Asp Glu Arg Leu Arg Pro Val Pro Pro
                325                 330                 335

Gly Val Thr Gly Glu Leu Tyr Ile Ala Gly Ala Gly Leu Ala Arg Gly
                340                 345                 350

Tyr Trp Asp Gln Ser Ala Arg Thr Ala Glu Arg Phe Thr Ala Asp Pro
                355                 360                 365

His Ala His Leu Phe Gly Asp Thr Gly Gly Arg Met Tyr Arg Thr Gly
                370                 375                 380

Asp Leu Ala Arg Arg Asp Ala Asp Gly Val Leu His Phe Cys Gly Arg
385                 390                 395                 400

Ala Asp Gln Gln Val Lys Ile Arg Gly Phe Arg Ile Glu Pro Gly Glu
                405                 410                 415

Ile Glu Thr Ala Leu Ala Ala His Pro Asp Val Thr Arg Ala Ala Val
                420                 425                 430
```

-continued

Val Ala Arg Pro Gly Arg Ala Gly Asp Lys Val Leu Val Ala Tyr Leu
    435                 440                 445

Val Thr Ala Pro Asp Ala Gly Asp Thr Thr Ala Glu Gln Leu Arg Ala
450                 455                 460

Gly Leu Glu Thr Gln Leu Pro Asp Tyr Met Val Pro Ala Ala Phe Val
465                 470                 475                 480

Ala Leu Pro Ala Leu Pro Val Thr Pro Asn Gly Lys Leu Asp Arg Asp
                485                 490                 495

Ala Leu Pro Glu Pro Asp Trp Gly Gly Ala Gly Arg Pro Pro Arg
            500                 505                 510

Gly Pro Arg Glu Glu Ile Leu Cys Gly Leu Phe Ala Glu Val Leu Gly
            515                 520                 525

Ala Pro Arg Val Gly Thr Asp Asp Asn Phe Phe Glu Leu Gly Gly His
        530                 535                 540

Ser Met Leu Ala Thr Arg Leu Val Gly Arg Val Lys Thr Val Leu Gly
545                 550                 555                 560

Ala Asp Ile Gly Val Arg Thr Leu Phe Glu Ala Pro Thr Val Ala Ala
                565                 570                 575

Leu Ala Ala Arg Ile Asp Gly Ala Asp Ala Ala Ser Val Pro Glu Ala
            580                 585                 590

Glu Ala Val Pro Pro Tyr Gly Pro Ala Pro Leu Thr Pro Val Met Ala
        595                 600                 605

Arg Ile Ala Glu Leu Gly Leu Gly Gly Asp Asp Phe Asn Gln Ser Val
    610                 615                 620

Val Val Ser Leu Pro Pro Ala Val Asp Arg Asp Arg Leu Val Pro Ala
625                 630                 635                 640

Leu Gln Arg Val Leu Asp His His Asp Ala Leu Arg Leu Arg Val Leu
                645                 650                 655

Pro Asp Gly Ser Thr Glu Val Arg Ala Pro Gly Ser Val Pro Ala Ala
            660                 665                 670

Asp Val Leu Ser Val Val Thr Arg Ala Pro Gly Ala Thr Gly Glu Ala
        675                 680                 685

Arg Asp Ala Leu Leu Val Glu Ala Ala Cys Ala Ala Arg Asp Arg Leu
    690                 695                 700

Ala Pro Ala Glu Gly Arg Met Leu Gln Ala Val Leu Val Asp Gly Thr
705                 710                 715                 720

Asp Asp Thr Asp Gly Thr Gly Thr Ser Gly Ala Asp Gly Val Leu
                725                 730                 735

Ile Leu Val Ala His His Leu Val Val Asp Ser Val Thr Trp Ser Ile
            740                 745                 750

Val Val Pro Asp Leu Ala Ala Ala Tyr Arg Gly Glu Glu Pro Ala Pro
        755                 760                 765

Val Gly Thr Ser Trp Arg Gln Trp Ala Thr Ser Leu Ala Arg Leu Ala
    770                 775                 780

Thr Asp Pro Arg Val Glu Ala Glu Thr Ala His Trp Glu His Thr Leu
785                 790                 795                 800

Thr Gly Ala Gly Thr Leu Arg Leu Asp Arg Gly Arg Asp Leu Gln Gly
                805                 810                 815

Asp Ala Gly Arg Ile Ser Leu Asp Leu Ala Pro His Thr Thr Glu Ala
            820                 825                 830

Leu Leu Thr Arg Leu Pro Gly Gly Val Asn Ala Ser Val His Asp Val
        835                 840                 845

Leu Leu Thr Ala Phe Ala Phe Ala Val Ala Gly Trp Arg Arg Gly Arg
    850                 855                 860

```
Gly Glu Asp Pro Asp Ala Pro Val Val Leu Asp Leu Glu Ser His Gly
865                 870                 875                 880

Arg His Glu Glu Ala Val Pro Gly Ala Glu Leu Ser Arg Thr Ala Gly
            885                 890                 895

Trp Phe Thr Ala Leu His Pro Val Arg Leu Ala Pro Asp Val Thr Asp
        900                 905                 910

Trp Ala Arg Leu His Gln Asp Gly Asp Ala Leu Arg Asp Gly Leu Lys
    915                 920                 925

Gln Val Lys Glu Gln Leu Arg Ser Val Pro Gly Asp Gly Leu Gly His
930                 935                 940

Gly Leu Leu Arg His Leu Asn Pro Thr Ala Gly Pro Arg Leu Ala Arg
945                 950                 955                 960

Leu Pro Glu Pro Asp Phe Gly Phe Asn Tyr Leu Gly Arg Arg Val Thr
                965                 970                 975

Pro Ala Thr Gly Thr Pro Glu Pro Trp Thr Val Thr Gly Gly Gly Leu
            980                 985                 990

Ala Ala Ser Arg Pro Thr Ala Pro Met Ala His Ala Val Glu Leu Ser
        995                 1000                1005

Ala Val Val His Glu Gly Ala Asp Gly Pro Arg Leu Arg Ala Glu
    1010                1015                1020

Trp Thr Tyr Ala Arg Arg Leu Val Pro Asp His Asp Ala Arg Arg
    1025                1030                1035

Leu Ala Glu Gln Trp Phe Arg Ala Leu Glu Ala Leu Val Glu Gln
    1040                1045                1050

Ala Asp Arg Ala Gly Thr Gly Gly Leu Thr Pro Ser Asp Val Thr
    1055                1060                1065

Leu Gly Ser Leu Ser Gln Ser Glu Ile Glu Glu Phe Glu Ser Asp
    1070                1075                1080

Leu Glu Ser Glu Trp Leu Ile Asn
    1085                1090

<210> SEQ ID NO 5
<211> LENGTH: 3436
<212> TYPE: DNA
<213> ORGANISM: Artificial Sequence
<220> FEATURE:
<223> OTHER INFORMATION: Hybrid nucleotide sequence

<400> SEQUENCE: 5
agtcttaagc tcgggcccca ataatgatt ttattttgac tgatagtgac ctgttcgttg      60
caacaaattg atgagcaatg ctttttata atgccaactt tgtacaaaaa agcaggctcc     120
gcggccgcct tgtttaactt taagaaggag cccttcacca tggcctgcct gccccgccgc     180
atcgccgaac aggccgcccg caccccgcac gcggtcgccg tcaccgaagc cggcggcacc     240
ctgatcacct acagcgaact cgacgcccgc gccaaccgcc tggcccgcca cctgatccgc     300
cgcggcgtca ccgcggagac ccgcgtcgcc gtcctcgccg aacgctccgc ccagctcgtc     360
gtcaccaccc tcgcgatcct caaggccggc ggcgtgtacg tgccccctgca caccggctat     420 cccgtcgacc ggatgcggca cgtcctcgcc gacaccgaag cggccctgct gctcaccgac     480
acccaccacg ccgccaccgc ggcccgcctg acacccccg ccctcaccgt cgacgaggac     540
accacggccg gcgagcagga caccaccgcc ccggacgtca ccgtgcggcc cgaccagctc     600
gcctacatca tgttcacctc cggctcgacc ggcacccca agggcatcgg catcacccac     660
cgcgacgcca tcgccctggc cgccgaccgc tgctgggacc tggacaccgg ctcccgcgtc     720
```

-continued

```
ctgatgcact ccccgtacgc cttcgacatc tccaccttcg aactgttcgc cccgctgctg      780
gccggcgggc ggatcgtcgt cgcaccccgc ggcgacatcg acgcggccgt cctgcagcgc      840
accctcgccg cccacggcgt cacctcgctg ctgctgaccg ccggcctgct cggcgtgatc      900
gccgacgagg caccggaggt cttcaccggc gtcaaggacg tgtggaccgg cggcgacgtc      960
gtctctccca ccgccgtgcg ccgcgtcctc gaagcctgcc ccggcaccgt cgtcaagacc     1020
ctctacgggc cgaccgagac caccctgggc tgcacctggc tgccgttcac cgaccccgc      1080 cgcatcccgc ccgccgtccc catcggccgg ccgctggaca cacccgcgc ctacgtcctc      1140 gacgaacggc tgcggcccgt accgcccggc gtcaccggcg agctgtacat cgccggcgcc     1200
ggcctcgccc gcggctactg ggaccagagc gcccgcaccg cggaacgctt caccgccgac     1260
ccgcacgccc acctgttcgg cgacacgggc ggccgcatgt accgcaccgg cgacctggcc     1320
cgccgcgacg ccgacggcgt cctccacttc tgcggccgcg ccgaccagca ggtcaagatc     1380
cgcggcttcc gcatcgaacc cggcgagatc gagaccgcgc tcgccgccca ccccgacgtc     1440
acccgcgccg ccgtcgtcgc ccgccccggc cgggccggcg acaaggtcct cgtcgcctac     1500
ctcgtcaccg ccccgacgc gggcgacacc ccgccgaaac aactgcgcgc cggcctcgag     1560
acccaactgc ccgactacat ggtccccgcc gcgttcgtcg cgctgcccgc cctgcccgtc     1620
acgcccaacg gcaaactcga ccgcgacgca ctgcccgaac ccgactgggg cggcggcgcc     1680
ggacgcccgc cccgcggccc ccgcgaggaa atcctgtgcg gcctgttcgc cgaggtcctc     1740 ggcgccccc gggtcggcac cgacgacaac ttcttcgaac tcggcggcca ctccatgctc     1800
gccacccgcc tcgtcggccg cgtcaagacc gtcctcggcg ccgacatcgg cgtacgcacc     1860
ctcttcgagg cgccgaccgt cgccgccctc gccgcccgca tcgacggcgc cgacgcggcc     1920
tccgtgccgg aggccgaagc ggtgccgccg tacggtcccg ccccgctgac ccccgtgatg     1980
gcccgcatcg ccgaactggg cctgggcgga cgacttca accagtcggt cgtggtgtcc     2040
ctgccgcccg cggtggaccg ggaccggctc gtcccggccc tgcaacgtgt gctcgaccac     2100
catgacgcgc tgcgcctgcg cgtcctgccc gacgggagca cggaggtacg cgccccgggc     2160
agtgtgccgg ccgcggacgt cctgagcgtc gtcacgcggg ccccggcgc caccggcgag     2220 gcgcgcgacg ccctgctcgt ggaggcggcg tgccgcgcac gggaccggct cgcaccggcc     2280
gagggccgca tgctccaggc ggtcctggtc gacggcacgg acgacacgga cggcacgggc     2340
gggacctccg gggcggacgg cgtgctgatc ctggtcgccc accacctggt ggtcgactcg     2400
gtgacgtgga gcatcgtcgt accggacctc gccgcgcct accggggcga ggagcccgcc     2460
ccggtgggca cctcgtggcg gcagtgggcc acctccctgg cacggctggc caccgacccc     2520
cgcgtcgagg cggagaccgc ccactgggag cacacgctca ccggggcggg caccctgcgg     2580
ctggaccgcg gccgcgatct ccagggcgac gccggacgca tcagcctcga cctggccccg     2640
cacacgaccg aggccctgct cacgcgcctg cccgggggcg tcaacgcgag cgtgcacgac     2700
gtcctgctga ccgccttcgc gttcgccgtc gccgggtggc ggcgcggacg cggcgaggac     2760
ccggacgcgc ccgtcgtgct cgacctggag agccacggcc ggcacgagga ggcggtgccg     2820
ggcgccgaac tcagccgcac ggcgggctgg ttcacggccc tccacccggt gcggctggct     2880
ccggacgtca ccgactgggc gcggctgcac caggacggca cgcgctccgg gacggcctc     2940 aagcaggtga aggaacagtt gcggtccgta ccgggcgacg gcctcggcca cggcttgctg     3000
cgccacctca accccaccgc tgggcccgc ctcgcacgcc ttcccgagcc cgacttcggc     3060
ttcaactacc tgggccgccg ggtcaccccg gccaccggca ccccggaacc gtggaccgtc     3120
```

```
acgggcggcg gcctcgccgc ctcgcggccc acggcgccga tggcccacgc ggtggagctg     3180
agcgccgtcg tccacgaggg ggcggacggc ccccgactgc gcgcggagtg gacctacgca     3240
cgccgcctgg tccccgatca cgacgcccgc cgcctggccg agcaatggtt ccgggcgctg     3300
gaagccctgg tggagcaggc cgaccgggcc ggcaccggcg gcctgacccc gtccgacgtg     3360
accctcggct cgctcagcca gtccgagatc gaggaattcg agtccgacct tgagtccgag     3420
tggttaatta attgaa                                                     3436
```

<210> SEQ ID NO 6
<211> LENGTH: 1087
<212> TYPE: PRT
<213> ORGANISM: Artificial Sequence
<220> FEATURE:
<223> OTHER INFORMATION: Hybrid amino acid sequence

<400> SEQUENCE: 6

```
Ser Gln Gln Pro Thr Arg Ala Arg Gly Lys Ile Glu Asp Ile Leu Pro
 1               5                  10                  15

Leu Ser Pro Leu Gln Glu Gly Phe Val Phe Leu Gly Leu Leu His Thr
            20                  25                  30

Glu Gly Pro Asp Leu Tyr Ile Gly Gln Val Ala Phe Asp Leu Glu Gly
        35                  40                  45

Pro Phe Asp Gly Ala Arg Met Arg Glu Ala Ala Arg Ala Leu Leu Arg
    50                  55                  60

Arg His Ala Asn Leu Arg Ala Gly Phe Arg Gln Arg Lys Asn Gly Ala
65                  70                  75                  80

Trp Ala Gln Leu Val Leu Arg Asp Val Asp Leu Pro Trp Gln Asp Ala
                85                  90                  95

Asp Leu Ser Thr Leu Ser Glu Glu Arg Arg Ala Glu Ala Asp Arg
            100                 105                 110

Leu Ala Ala Ala Asp Arg Ala Arg Arg Phe Asp Leu Gly Arg Pro Pro
        115                 120                 125

Leu Leu Arg Phe Thr Ala Ile Arg Leu Ser Ala Asp Arg Val Arg Leu
    130                 135                 140

Val Met Thr Asn His His Ile Val Leu Asp Gly Trp Ser Met Pro Val
145                 150                 155                 160

Leu Leu Arg Glu Leu Met Ala Leu Tyr Ala Ala Glu Gly Asp Pro Ser
                165                 170                 175

Ala Leu Pro Arg Val Arg Pro Tyr Arg Asp Tyr Leu Ala Trp Leu Asp
            180                 185                 190

Ala Arg Asp Arg Asp Ala Ala Arg Asp Ala Trp Arg Arg Ser Leu Ser
        195                 200                 205

Gly Leu Asp Glu Ala Thr Leu Leu Ala Pro Asp Ala Gly Pro Ala Ser
    210                 215                 220

Thr Ala Pro Ser Gln Val Ser Phe Thr Val Asp Ser Glu Val Ser Gly
225                 230                 235                 240

Ala Leu Ser Ala Trp Ala Arg Gly Gln Gly Val Thr Met Asn Thr Val
                245                 250                 255

Val Gln Gly Ala Trp Ala Leu Ala Leu Ala Gln Ala Thr Gly Arg Asp
            260                 265                 270

Asp Val Val Phe Gly Ala Thr Val Ser Gly Arg Pro Pro Glu Leu Pro
        275                 280                 285

Gly Val Glu Ser Met Ile Gly Leu Phe Ile Asn Thr Leu Pro Val Arg
    290                 295                 300

Ala Arg Leu Asp Gln Ala Glu Pro Leu Gly Asp Leu Phe Arg Arg Leu
```

```
            305                 310                 315                 320
Gln Asn Glu Gln Ala Arg Leu Leu Asp His Gln Trp Pro Gly Leu Ala
                325                 330                 335
Asp Ile Gln His Trp Ala Gly His Gly Glu Leu Phe Asp Thr Ala Met
                340                 345                 350
Val Phe Gln Asn Tyr Pro Val Glu Glu Gly Asp Leu Thr Ala Pro Ala
                355                 360                 365
Asp Pro Asp Arg Leu Arg Val Ala Ser Ala Asp Ile Lys Gly Gly Thr
        370                 375                 380
His Phe Ala Val Asn Val Val Ala Thr Met Arg Gly Ala Glu Leu Ser
385                 390                 395                 400
Phe Arg Val Asp Tyr Arg Pro Asp Leu Tyr Asp Glu Ala Tyr Ala Arg
                405                 410                 415
Asp Phe Gly Arg Arg Met Leu Arg Val Leu Glu Thr Leu Ile Ser Asp
                420                 425                 430
Pro Asp Arg Pro Val Ala His Leu Asp Thr Leu Asp Pro Ala Val Arg
        435                 440                 445
Glu Arg Val Leu Val Glu Trp Asn Gly Ala Pro Thr Gln Leu Pro Gly
    450                 455                 460
Thr Pro Leu His Glu Leu Thr Ser Leu Ile Ser Pro Ser Met Arg Ala
465                 470                 475                 480
Arg Phe Asp Ser Trp Asn Glu Thr Ala Glu Glu Phe Pro Ala Asp Lys
                485                 490                 495
Thr Leu His Ala Val Phe Glu Glu Met Ala Glu Arg Trp Pro Asp Glu
                500                 505                 510
Ile Ala Val Val Tyr Arg Glu Asn Arg Leu Thr Tyr Arg Glu Leu Asn
                515                 520                 525
Glu Arg Ala Asn Arg Leu Ala His Tyr Leu Arg Ser Val Val Glu Leu
        530                 535                 540
Arg Pro Asp Asp Leu Val Ala Leu Val Leu Asp Lys Ser Glu Leu Met
545                 550                 555                 560
Ile Thr Ala Ile Ile Ala Ala Trp Lys Thr Gly Ala Ala Tyr Val Pro
                565                 570                 575
Ile Asp Ser Gly Tyr Pro Asp Asp Arg Ile Ser Phe Met Leu Ser Asp
                580                 585                 590
Thr Ala Ala Arg Val Val Val Thr Asn Glu Ile His Ser Asp Arg Leu
                595                 600                 605
Arg Ser Leu Ala Glu Thr Gly Thr Pro Val Leu Glu Ile Glu Leu Leu
        610                 615                 620
His Leu Asp Asp Gln Pro Ala Val Asn Pro Val Thr Glu Thr Thr Ser
625                 630                 635                 640
Thr Asp Leu Ala Tyr Ala Ile Tyr Thr Ser Gly Thr Thr Gly Lys Pro
                645                 650                 655
Lys Ala Val Leu Val Glu His Arg Gly Val Val Asn Leu Gln Val Ser
                660                 665                 670
Leu Ala Lys Leu Phe Gly Leu Asp Lys Ala His Arg Asp Glu Ala Leu
        675                 680                 685
Leu Ser Phe Ser Asn Tyr Ile Phe Asp His Phe Val Glu Gln Met Thr
    690                 695                 700
Asp Ala Leu Leu Asn Gly Gln Lys Leu Val Val Leu Asp Gly Ser Met
705                 710                 715                 720
Arg Thr Asp Pro Gly Arg Leu Cys Arg Tyr Met Asn Asp Glu Gln Val
                725                 730                 735
```

```
Thr Tyr Leu Ser Gly Thr Pro Ser Val Leu Ser Leu Tyr Asp Tyr Ser
            740                 745                 750

Ser Ala Thr Ser Leu Thr Arg Ile Asp Ala Ile Gly Glu Asp Phe Thr
            755                 760                 765

Glu Pro Val Phe Ala Lys Ile Arg Gly Thr Phe Pro Gly Leu Ile Ile
770                 775                 780

Asn Gly Tyr Gly Pro Thr Glu Ile Ser Ile Thr Ser His Lys Arg Pro
785                 790                 795                 800

Tyr Pro Pro Asp Val His Arg Val Asn Lys Ser Ile Gly Phe Pro Val
            805                 810                 815

Ala Asn Thr Lys Cys His Val Leu Asn Lys Ala Met Lys Pro Val Pro
            820                 825                 830

Val Gly Gly Ile Gly Glu Leu Tyr Ile Gly Gly Ile Gly Val Thr Arg
            835                 840                 845

Gly Tyr Leu Asn Arg Glu Asp Leu Thr Ala Asp Arg Phe Val Glu Asn
850                 855                 860

Pro Phe Gln Thr Ala Glu Arg Arg Leu Gly Glu Asn Gly Arg Leu
865                 870                 875                 880

Tyr Lys Thr Gly Asp Leu Val Arg Trp Leu Pro Asn Gly Glu Val Glu
            885                 890                 895

Tyr Leu Gly Arg Thr Asp Leu Gln Val Lys Ile Arg Gly Gln Arg Val
            900                 905                 910

Glu Leu Gly Glu Val Glu Ala Ala Leu Ser Ser Tyr Pro Gly Val Val
            915                 920                 925

Arg Ser Leu Val Val Ala Arg Glu His Ala Val Gly Gln Lys Tyr Leu
930                 935                 940

Val Gly Phe Tyr Val Gly Glu Gln Glu Phe Asp Glu Gln Asp Leu Lys
945                 950                 955                 960

Gln Trp Met Arg Lys Lys Leu Pro Glu Ser Val Val Pro Ala Arg Val
                965                 970                 975

Leu Arg Ile Thr Asp Ile Pro Val Thr Pro Ser Gly Lys Leu Asp Ala
            980                 985                 990

Arg Arg Leu Pro Glu Thr Asp Phe Gly Ala Gly Glu Gly Ala Glu Tyr
            995                 1000                1005

Val Ala Pro Val Ser Glu Phe Glu Leu Lys Leu Cys Gly Ile Trp
1010                1015                1020

Ala Gln Val Leu Glu Ile Ala Pro Asp Arg Ile Gly Val His Asp
1025                1030                1035

Asp Phe Phe Ala Leu Gly Gly Asp Ser Ile Arg Ala Met Ala Leu
1040                1045                1050

Ala Gln Ala Ile Thr Thr Gly Phe Gly Gln Gly Leu Gly Val Ala
1055                1060                1065

Thr Val Leu Gln His Thr Thr Leu Ala Ala Gln Ala Glu His Ile
1070                1075                1080

Gln Ala Ala Ala
1085
```

<210> SEQ ID NO 7
<211> LENGTH: 3263
<212> TYPE: DNA
<213> ORGANISM: Artificial Sequence
<220> FEATURE:
<223> OTHER INFORMATION: Hybrid nucleotide sequence

<400> SEQUENCE: 7
agccagcaac cgacccgtgc gcgcggcaag atcgaggaca tccttccgct ctccccgctg    60

```
caagagggct tcgtgttcct cgggctgctg cacaccgagg ggcccgacct ctacatcggc    120
caggtggcct tcgacctgga gggccccttc gacggcgccc ggatgcgcga ggcggcccgg    180
gcgctgctgc gccggcacgc caacctgcgc gccgggttcc ggcagcgcaa gaacggggcc    240
tgggcccaac tggtcctgcg cgacgtcgac ctgccgtggc aggacgccga cctgagcacg    300
ctgtccgagg aggagcgccg gcggaggcc gaccggctcg cggccgccga ccgtgccccgc    360 cgtttcgacc tgggccggcc cccgctgctg cgcttcaccg ccatccggct gtccgccgac    420
cgcgtccgcc tggtgatgac caaccaccac atcgtgctgg acggctggtc catgccggtc    480
ctgctgcgcg aactcatggc gctctacgcc gccgagggtg accccctccgc gctcccccgg    540 gtccgtccct accgcgacta cctggcctgg ctcgacgccc gcgaccggga cgccgcccgc    600
gacgcctggc ggcggtccct gtccgggctc gacgaggcca ccctcctcgc cccggacgcc    660
ggcccggcgt cgaccgctcc ctcgcaggtg tccttcaccg tggactccga ggtcagcggc    720
gccctgtcgg cctgggctcg gggccagggc gtgaccatga acacggtggt ccagggtgcc    780
tgggccctcg cgctggccca ggccaccgga cgcgacgacg tcgtcttcgg cgccaccgtc    840 tccgccgcc cgcccgagct gccccggcgtc gagtccatga tcggcctgtt catcaacacc    900
ctgcccgtcc gcgcccgcct cgaccaggcc gaacccctcg gcgacctctt ccgccgcctc    960
cagaacgaac aggcccgcct cctggaccac cagtggcccg gactcgccga catccagcac   1020
tgggccggac acggcgaact cttcgacacc gccatggtct tccagaacta cccggtcgag   1080
gagggcgacc tcaccgcccc cgccgacccg gaccggctcc gggtcgcctc ggccgacatc   1140
aagggcggca cgcacttcgc cgtcaacgtc gtcgcgacga tgcgcggcgc cgaactgtcc   1200
ttccgcgtcg actaccgacc cgacctctac gacgaggcgt acgcccgcga cttcggccga   1260
cggatgctac gggtactgga aaccctgatc tccgacccgg accgtccgt ggcccacctg   1320 gacaccctcg acccggccgt acgggagcgg gtcctggtgg agtggaacgg gccccgacc   1380 cagcttcccg gaacgccgct gcacgaactg actagtctca tctcaccgtc gatgcgcgcg   1440
cggttcgatt cgtggaacga gaccgccgag gaattccccg cggacaagac gctgcacgcg   1500
gtgttcgagg agatggccga gcgctggccg gacgagatcg ccgtggtgta ccgggaaaac   1560
cggctgacct accgcgagct gaacgagcgg gccaaccgcc tcgcgcacta cctgcgctcg   1620
gtggtcgaac tgcgcccgga cgacctcgtc gcgctggtgc tggacaagag cgaactgatg   1680
atcaccgcga tcatcgcggc gtggaagacc ggtgcggcct acgtgccgat cgactccggc   1740
tacccggacg accggatctc gttcatgctc tccgacaccg ccgcgcgcgt ggtggtgacc   1800
aacgagatcc acagcgaccg gctgcgttcg ctggcggaga ccggcacgcc cgtgctggag   1860
atcgaactgc tgcacctcga cgaccagccg gcggtgaacc cggtcaccga gaccaccagc   1920
accgacctcg cctacgcgat ctacacctcc ggcaccaccg gcaagcccaa ggcggtgctt   1980
gtcgaacacc gcggcgtggt caacctccag gtgtcgctgg cgaagctgtt cggtctggac   2040
aaggcgcacc gcgacgaggc gctgctgtcg ttctcgaact acatcttcga ccacttcgtc   2100
gagcagatga ccgacgcgct gctcaacggg cagaagctgg tggtgctcga cggcagcatg   2160
cgcaccgatc ccgggcgcct gtgcggtac atgaacgacg agcaggtcac ctacctctcg   2220
ggcacgccgt cggtgctctc gctctacgac tactcgtcgg cgacctcgct gacccggatc   2280
gacgcgatcg gcgaggactt caccgagccg gtgttcgcca agatccgcgg caccttcccc   2340
ggcctgatca tcaacggcta cgggccgacg gaaatctcga tcaccagcca caacgcgccc   2400
tacccgccgg acgtgcaccg ggtgaacaag agcatcggct tcccggtcgc caacaccaag   2460
```

```
tgccacgtgc tgaacaaggc gatgaagccg gtcccggtcg gcggtatcgg cgagctctac   2520
atcggcggca tcggcgtgac caggggggtac ctcaaccgcg aggacctgac cgccgaccgg   2580
ttcgtggaga acccgttcca gaccgcggag aacggcggc tgggcgagaa cggccgcctg    2640
tacaagaccg gcgacctggt gcgctggctg cccaacggcg aggtggagta cctcggccgc   2700
accgacctgc aggtcaagat ccgcggccag cgcgtggaac tcggcgaggt ggaggcggcg   2760
ctgtcgtcct accccggggt ggtgcgctcg ctggtcgtgg cccgagagca cgcggtgggg   2820
cagaagtacc tggtcgggtt ctacgtcggc gagcaggagt tcgacgagca ggacctcaag   2880
cagtggatgc gcaagaagtt gcccgagtcc gtggtgcccg cgcgcgtcct gcggatcacc   2940
gacatcccgg tgaccccgag cggcaagctg acgcgcggc gcctgccgga cgcggacttc   3000
ggggccggtg agggcgccga atacgtcgcg ccggtcagcg agttcgagct gaagctgtgc   3060
ggtatctggg cccaggtgct ggagatcgcg ccggaccgca tcggcgtgca cgacgacttc   3120
ttcgcgctcg gcggcgacag catccgcgcg atggcgctcg cgcaggcgat caccaccggc   3180
ttcggccagg gcctcggtgt ggcgaccgtg ctccagcaca ccacgctcgc cgcccaggcc   3240
gagcacatcc aggcggccgc gct                                           3263
```

<210> SEQ ID NO 8
<211> LENGTH: 1095
<212> TYPE: PRT
<213> ORGANISM: Artificial Sequence
<220> FEATURE:
<223> OTHER INFORMATION: Hybrid amino acid sequence

<400> SEQUENCE: 8

```
Ile Glu His Cys Ala Ala Gln Glu His Ile His Leu Thr Pro Ser Asp
1               5                   10                  15

Ile Ser Leu Lys Asp Ile Thr Ile Glu Glu Leu Asp Gln Phe Val Lys
            20                  25                  30

Gln Thr Gln His Ile Gly Asp Ile Glu Asn Ile Tyr Pro Leu Thr Pro
        35                  40                  45

Met Gln Lys Gly Met Leu Phe His Ser Leu Ile Asp Ser Ala Ser Arg
    50                  55                  60

Ala Tyr Phe Glu Gln Ala Ala Phe Asp Leu Lys Gly Asp Leu Asp Ile
65                  70                  75                  80

Glu Ala Phe Thr Met Ser Leu Ser Tyr Leu Ala Glu Ser His Glu Ile
                85                  90                  95

Leu Arg Thr His Phe Tyr Thr Glu Trp Lys Asp Gln Pro Leu Gln Ile
            100                 105                 110

Val Phe Arg Lys Lys Pro Ile Glu Ile Thr Val Glu Asp Ile Arg Ser
        115                 120                 125

Met Lys Asn Lys Gln Arg Asn Glu Phe Ile Ala Gly Phe Val Gln Lys
    130                 135                 140

Asp Lys Ala Arg Gly Phe Asp Leu Thr Gln Asp Ala Leu Met Arg Val
145                 150                 155                 160

Ser Ile Leu Arg Thr Glu Asp Asp Gln Val Arg Leu Ile Trp Ser Phe
                165                 170                 175

His His Ile Leu Met Asp Gly Trp Cys Leu Pro Leu Ile Thr Lys Glu
            180                 185                 190

Val Phe Glu Thr Tyr Tyr Glu Leu Leu Glu Arg Arg Gln Pro Glu Arg
        195                 200                 205

Glu Ala Val Thr Pro Tyr Ser Arg Tyr Ile Glu Trp Leu Glu Asp Gln
    210                 215                 220
```

```
Asp His Gln Asn Ala Leu Ala Tyr Trp Gln Lys Tyr Leu Asp Gly Tyr
225                 230                 235                 240

Glu Gly Gln Thr Val Leu Leu Lys Glu Pro Val Ser Asn Gln Ala Lys
            245                 250                 255

Gly Tyr Gln Lys Gln Arg Leu Ala Cys Arg Leu Gly Lys Gln Leu Ser
        260                 265                 270

Glu Glu Ile Arg Gln Thr Ala Ser Lys His His Val Thr Val Asn Thr
    275                 280                 285

Phe Ile Gln Ser Ala Trp Gly Leu Leu Leu Gln Arg Tyr Asn Asn Ser
290                 295                 300

Gln Asp Val Val Phe Gly Ser Val Val Ser Gly Arg Pro Ala Glu Ile
305                 310                 315                 320

Pro Gly Ile Glu Ser Met Val Gly Leu Phe Ile Asn Thr Ile Pro Val
            325                 330                 335

Arg Ile Thr Ala Gln Pro Gly Met Thr Val Glu Gln Val Leu Lys Met
        340                 345                 350

Ser Gln Glu Gln Ala Leu Ala Ser Gln Ala Tyr Asp Thr Phe Pro Leu
    355                 360                 365

Tyr Glu Ile Gln Ala Gln Thr Glu Gln Lys Gln Gln Leu Ile Ser His
370                 375                 380

Ile Met Val Phe Glu Asn Tyr Pro Val Glu Lys Gln Met Glu His Met
385                 390                 395                 400

Lys Pro Asn Arg Asp Ala Leu Asp Ile Ile Asn Phe His Met Glu Glu
            405                 410                 415

His Thr His Tyr Asp Phe Asn Phe Ile Val Met Pro Ala Gly Glu Ile
        420                 425                 430

Asp Ile His Phe Val Tyr Asn Ser Asn Val Tyr Asp His Ala Ser Val
    435                 440                 445

Lys Arg Met Glu Glu His Phe Met Gln Ile Ile Lys Gln Met Val Asn
450                 455                 460

Ser Gln Ala Ile Arg Val Gln Asp Leu Asp Ile Leu Thr Gly Thr Ser
465                 470                 475                 480

Leu Ile Ser Pro Ser Met Arg Ala Arg Phe Asp Ser Trp Asn Glu Thr
            485                 490                 495

Ala Glu Glu Phe Pro Ala Asp Lys Thr Leu His Ala Val Phe Glu Glu
        500                 505                 510

Met Ala Glu Arg Trp Pro Asp Glu Ile Ala Val Val Tyr Arg Glu Asn
    515                 520                 525

Arg Leu Thr Tyr Arg Glu Leu Asn Glu Arg Ala Asn Arg Leu Ala His
530                 535                 540

Tyr Leu Arg Ser Val Val Glu Leu Arg Pro Asp Asp Leu Val Ala Leu
545                 550                 555                 560

Val Leu Asp Lys Ser Glu Leu Met Ile Thr Ala Ile Ala Ala Trp
            565                 570                 575

Lys Thr Gly Ala Ala Tyr Val Pro Ile Asp Ser Gly Tyr Pro Asp Asp
        580                 585                 590

Arg Ile Ser Phe Met Leu Ser Asp Thr Ala Ala Arg Val Val Val Thr
    595                 600                 605

Asn Glu Ile His Ser Asp Arg Leu Arg Ser Leu Ala Glu Thr Gly Thr
610                 615                 620

Pro Val Leu Glu Ile Glu Leu Leu His Leu Asp Asp Gln Pro Ala Val
625                 630                 635                 640

Asn Pro Val Thr Glu Thr Thr Ser Thr Asp Leu Ala Tyr Ala Ile Tyr
```

```
                645                 650                 655
Thr Ser Gly Thr Thr Gly Lys Pro Lys Ala Val Leu Val Glu His Arg
                660                 665                 670

Gly Val Val Asn Leu Gln Val Ser Leu Ala Lys Leu Phe Gly Leu Asp
                675                 680                 685

Lys Ala His Arg Asp Glu Ala Leu Leu Ser Phe Ser Asn Tyr Ile Phe
        690                 695                 700

Asp His Phe Val Glu Gln Met Thr Asp Ala Leu Asn Gly Gln Lys
705                 710                 715                 720

Leu Val Val Leu Asp Gly Ser Met Arg Thr Asp Pro Gly Arg Leu Cys
                725                 730                 735

Arg Tyr Met Asn Asp Glu Gln Val Thr Tyr Leu Ser Gly Thr Pro Ser
                740                 745                 750

Val Leu Ser Leu Tyr Asp Tyr Ser Ser Ala Thr Ser Leu Thr Arg Ile
                755                 760                 765

Asp Ala Ile Gly Glu Asp Phe Thr Glu Pro Val Phe Ala Lys Ile Arg
        770                 775                 780

Gly Thr Phe Pro Gly Leu Ile Ile Asn Gly Tyr Gly Pro Thr Glu Ile
785                 790                 795                 800

Ser Ile Thr Ser His Lys Arg Pro Tyr Pro Pro Asp Val His Arg Val
                805                 810                 815

Asn Lys Ser Ile Gly Phe Pro Val Ala Asn Thr Lys Cys His Val Leu
                820                 825                 830

Asn Lys Ala Met Lys Pro Val Pro Val Gly Gly Ile Gly Glu Leu Tyr
                835                 840                 845

Ile Gly Gly Ile Gly Val Thr Arg Gly Tyr Leu Asn Arg Glu Asp Leu
        850                 855                 860

Thr Ala Asp Arg Phe Val Glu Asn Pro Phe Gln Thr Ala Glu Glu Arg
865                 870                 875                 880

Arg Leu Gly Glu Asn Gly Arg Leu Tyr Lys Thr Gly Asp Leu Val Arg
                885                 890                 895

Trp Leu Pro Asn Gly Glu Val Glu Tyr Leu Gly Arg Thr Asp Leu Gln
                900                 905                 910

Val Lys Ile Arg Gly Gln Arg Val Glu Leu Gly Glu Val Glu Ala Ala
                915                 920                 925

Leu Ser Ser Tyr Pro Gly Val Val Arg Ser Leu Val Val Ala Arg Glu
                930                 935                 940

His Ala Val Gly Gln Lys Tyr Leu Val Gly Phe Tyr Val Gly Glu Gln
945                 950                 955                 960

Glu Phe Asp Glu Gln Asp Leu Lys Gln Trp Met Arg Lys Lys Leu Pro
                965                 970                 975

Glu Ser Val Val Pro Ala Arg Val Leu Arg Ile Thr Asp Ile Pro Val
                980                 985                 990

Thr Pro Ser Gly Lys Leu Asp Ala Arg Arg Leu Pro Glu Thr Asp Phe
                995                1000                1005

Gly Ala Gly Glu Gly Ala Glu Tyr Val Ala Pro Val Ser Glu Phe
        1010                1015                1020

Glu Leu Lys Leu Cys Gly Ile Trp Ala Gln Val Leu Glu Ile Ala
        1025                1030                1035

Pro Asp Arg Ile Gly Val His Asp Asp Phe Phe Ala Leu Gly Gly
        1040                1045                1050

Asp Ser Ile Arg Ala Met Ala Leu Ala Gln Ala Ile Thr Thr Gly
        1055                1060                1065
```

```
Phe Gly Gln Gly Leu Gly Val Ala Thr Val Leu Gln His Thr Thr
    1070            1075                1080

Leu Ala Ala Gln Ala Glu His Ile Gln Ala Ala Ala
    1085            1090            1095

<210> SEQ ID NO 9
<211> LENGTH: 3287
<212> TYPE: DNA
<213> ORGANISM: Artificial Sequence
<220> FEATURE:
<223> OTHER INFORMATION: Hybrid nucleotide sequence

<400> SEQUENCE: 9
atcgaacatt gcgcagctca agaacacatt cacctgacgc caagcgatat ttcgctgaag      60
gacataacaa tcgaggaatt agatcaattt gttaagcaaa cacagcatat cggcgacatt     120
gaaaatatat atcctttaac tcccatgcag aaaggtatgc tgttccatag tttaatcgat     180
tcggcttcca gagcttactt tgaacaagcc gcttttgacc tcaaaggcga cttggatatt     240
gaggcattta caatgagttt gtcgtatctg gcggaaagcc atgagattct ccggactcat     300
ttttatacgg aatggaaaga tcagcctttg cagatcgtat tccgaaaaaa accgatcgaa     360
ataaccgttg aagatattcg aagcatgaag aataaacaac gaaacgagtt cattgccggc     420
tttgtacaaa aagataaggc aagaggattc gaccttaccc aagatgcgtt aatgcgcgta     480
tcaatccttc gtacagagga cgaccaagtc cgattgatat ggagcttcca tcatatttta     540
atggatggct ggtgtctgcc tcttattacg aaagaagtgt ttgaaaccta ttatgagctt     600
cttgagagaa gacaaccgga gcgggaagcc gtcaccccgt acagccgata tatcgaatgg     660
ctggaagacc aggatcatca gaacgctttg gcctattggc aaaaatattt ggacggttat     720
gaaggacaaa ccgttttact gaaagaacct gtctcaaacc aagccaaggg atatcaaaaa     780
caaaggcttg catgccggct cggaaagcag ctatcagaag aaatcagaca gactgcaagc     840
aagcatcacg tcaccgtgaa tacattcatt caaagtgcgt gggggctatt gctgcaaaga     900
tacaacaaca gtcaggatgt cgttttcggg tcggttgtat ccggacgccc ggcagaaatt     960
ccgggtattg aatccatggt cggcttattt atcaacacca ttccccgtacg tattaccgct    1020 cagcctggaa tgactgtgga acaagtgttg aaaatgagcc aggagcaggc attggcttct    1080
caggcgtatg atacatttcc gttgtatgaa attcaggctc aaaccgaaca aaagcagcag    1140
ctgatcagtc atatcatggt atttgaaaat tatccggtcg agaaacaaat ggagcatatg    1200
aaaccgaatc gtgacgcgct ggacattatc aatttccata tggaagagca tacccattac    1260
gatttcaatt tcattgtcat gccggctgga gaaatcgaca ttcattttgt atacaatagc    1320
aacgtctatg atcatgcaag tgtcaagcgg atggaagagc attttatgca aatcattaag    1380
cagatggtga acagtcaggc gattcgcgtc caagacttgg atatacttac gggaactagt    1440
ctcatctcac cgtcgatgcg cgcgcggttc gattcgtgga cgagaccgc cgaggaattc    1500 cccgcggaca agacgctgca cgcggtgttc gaggagatgg ccgagcgctg gccggacgag    1560
atcgccgtgg tgtaccggga aaaccggctg acctaccgcg agctgaacga gcgggccaac    1620
cgcctcgcgc actacctgcg ctcggtggtc gaactgcgcc cggacgacct cgtcgcgctg    1680
gtgctggaca gagcgaact gatgatcacc gcgatcatcg cggcgtggaa gaccggtgcg    1740
gcctacgtgc cgatcgactc cggctacccg gacgaccgga tctcgttcat gctctccgac    1800
accgccgcgc gcgtggtggt gaccaacgag atccacagcg accggctgcg ttcgctggcg    1860
gagaccggca cgcccgtgct ggagatcgaa ctgctgcacc tcgacgacca gccggcggtg    1920
```

-continued

```
aacccggtca ccgagaccac cagcaccgac ctcgcctacg cgatctacac ctccggcacc     1980
accggcaagc ccaaggcggt gcttgtcgaa caccgcggcg tggtcaacct ccaggtgtcg     2040
ctggcgaagc tgttcggtct ggacaaggcg caccgcgacg aggcgctgct gtcgttctcg     2100
aactacatct cgaccacttt cgtcgagcag atgaccgacg cgctgctcaa cgggcagaag     2160
ctggtggtgc tcgacggcag catgcgcacc gatcccgggc gcctgtgccg gtacatgaac     2220
gacgagcagg tcacctacct ctcgggcacg ccgtcggtgc tctcgctcta cgactactcg     2280
tcggcgacct cgctgacccg gatcgacgcg atcggcgagg acttcaccga gccggtgttc     2340
gccaagatcc gcggcacctt ccccggcctg atcatcaacg gctacgggcc gacggaaatc     2400
tcgatcacca gccacaaacg gccctacccg ccggacgtgc accgggtgaa caagagcatc     2460
ggcttcccgg tcgccaacac caagtgccac gtgctgaaca aggcgatgaa gccggtcccg     2520
gtcggcggta tcggcgagct ctacatcggc ggcatcggcg tgaccagggg gtacctcaac     2580
cgcgaggacc tgaccgccga ccggttcgtg gagaacccgt tccagaccgc ggaggaacgg     2640
cggctgggcg agaacggccg cctgtacaag accggcgacc tggtgcgctg gctgcccaac     2700
ggcgaggtgg agtacctcgg ccgcaccgac ctgcaggtca agatccgcgg ccagcgcgtg     2760
gaactcggcg aggtggaggc ggcgctgtcg tcctaccccg gggtggtgcg ctcgctggtc     2820
gtggcccgag agcacgcggt ggggcagaag tacctggtcg ggttctacgt cggcgagcag     2880
gagttcgacg agcaggacct caagcagtgg atgcgcaaga gttgcccga gtccgtggtg     2940
cccgcgcgcg tcctgcggat caccgacatc ccggtgaccc cgagcggcaa gctggacgcg     3000
cggcgcctgc cggagacgga cttcggggcc ggtgagggcg ccgaatacgt cgcgccggtc     3060
agcgagttcg agctgaagct gtgcggtatc tgggcccagg tgctggagat cgcgccggac     3120
cgcatcggcg tgcacgacga cttcttcgcg ctcggcggcg acagcatccg cgcgatggcg     3180
ctcgcgcagg cgatcaccac cggcttcggc cagggcctcg gtgtggcgac cgtgctccag     3240
cacaccacgc tcgccgccca ggccgagcac atccaggcgg ccgcgct                   3287
```

<210> SEQ ID NO 10
<211> LENGTH: 1706
<212> TYPE: PRT
<213> ORGANISM: Nocardia lactamdurans

<400> SEQUENCE: 10

```
Glu His Thr Ala Trp Thr Pro Pro Thr Ala Val Glu His Pro Pro
1               5                   10                  15

Val Ser Leu Ala Gln Glu Arg Leu Leu Phe Ile Asp Asp Phe Glu Gly
            20                  25                  30

Gly Thr Ala Ala Tyr Asn Ile Pro Phe Val Leu Arg Leu Pro Ala His
        35                  40                  45

Thr Arg Ala Ala Leu Pro Gly Ala Leu Gly Thr Leu Val Arg Arg His
    50                  55                  60

Pro Ala Leu Arg Thr Leu Leu Lys Thr Asp Asp Gln Gly Val Arg Arg
65                  70                  75                  80

Gln Tyr Pro Ile Pro Ala Asp Asp Val Arg Leu Glu Val Pro Ser Thr
                85                  90                  95

Thr Val Asp Ser Arg Ala Glu Leu Asp Glu Val Leu Thr Glu Arg Ala
            100                 105                 110

Gly Tyr Val Phe Arg Leu His Glu Glu Leu Pro Ile Arg Ala Glu Ala
        115                 120                 125

Phe Asp His Gly Asp Glu Ile Tyr Leu Ser Val Val His His Ser
    130                 135                 140
```

-continued

```
Cys Phe Asp Gly Trp Ser Trp Asp Ile Phe Arg Arg Glu Leu Ala Ala
145                 150                 155                 160

Leu Leu Asp Gly Val Pro Glu Ala Asp Leu Gly Ala Leu Arg Gly Thr
                165                 170                 175

Tyr Gly Glu Phe Ala Val Trp Gln Arg Gln Tyr Leu Thr Gly Lys Arg
            180                 185                 190

Leu Ala Ala Leu Thr Glu Phe Trp Thr Gly Ala Leu Gly Gly Phe Glu
        195                 200                 205

Thr Ile Ala Leu Pro Leu Asp His Pro Arg Pro Arg Phe Asp Tyr
    210                 215                 220

Arg Gly Arg Glu Leu Glu Phe Glu Leu Asp Glu Arg Thr Thr Glu Ala
225                 230                 235                 240

Leu Arg Glu Leu Ala Arg Thr Ala Arg Val Ser Leu Tyr Ser Val Leu
                245                 250                 255

Leu Gly Ala Trp Cys Leu Met Leu Asn Met Tyr Thr Gly Gln His Asp
            260                 265                 270

Leu Val Val Gly Thr Pro Ser Ala Asn Arg Gly Arg Pro Glu Phe Asp
        275                 280                 285

Arg Ala Val Gly Phe Phe Ala Asn Leu Leu Ala Leu Arg Val Arg Val
290                 295                 300

Asp Pro Ala Ala Thr Leu Pro Ala Tyr Val Arg Ser Val Gly Glu Ala
305                 310                 315                 320

Val Val Ala Ala Gln Val His Gly Glu Leu Pro Phe Glu Gln Leu Val
                325                 330                 335

Lys Glu Leu Lys Val Glu Lys Asp Pro Ser Arg His Pro Ile Leu Gln
            340                 345                 350

Leu Asn Phe Thr Leu Gln Asn Val Ser Asp His Thr Ser Ala Leu Thr
        355                 360                 365

Gly Tyr Gln Pro Asp Ser Gly Gly Trp Thr Thr Thr Lys Phe Asp Leu
    370                 375                 380

Ser Ala Thr Met Thr Glu Thr Ala Thr Gly Leu Ala Gly Asn Leu Thr
385                 390                 395                 400

Tyr Ala Ala Ser Leu Phe Asp Asp Thr Ser Ala Ser Gly Phe Ile Ala
                405                 410                 415

Thr Phe Lys His Val Leu Ala Glu Phe Ala Ser Ala Ala Ala Gln Thr
            420                 425                 430

Pro Ile Ala Gln Leu Thr Ala Leu Asp Glu Pro Gly Gln Ala Ala Leu
        435                 440                 445

Leu Thr Pro Pro Ala Glu Pro Ala Ala Arg Arg Thr Arg Thr Leu His
    450                 455                 460

Ala Val Phe Glu Glu Val Ala Ala Thr Trp Pro Asp Arg Val Ala Val
465                 470                 475                 480

Val His Gly Asp Val Arg Leu Thr Tyr Arg Glu Leu Asn Glu Arg Ala
                485                 490                 495

Asn Arg Leu Ala His His Leu Arg Ser Val Ala Glu Pro Arg Ala Asp
            500                 505                 510

Glu Leu Ile Ala Leu Val Leu Asp Lys Ser Glu Leu Thr Leu Val Ala
        515                 520                 525

Ile Leu Ala Val Trp Lys Ala Gly Ala Ala Tyr Met Pro Ile Asp Pro
    530                 535                 540

Ser Tyr Pro Asp Asp Arg Ile Ala Phe Met Leu Ser Asp Thr Gly Ala
545                 550                 555                 560

Lys Leu Val Leu Ala Gly Glu Ala His Gly Ser Arg Val Arg Gly Leu
```

-continued

```
                565                 570                 575
Thr Ser Gly Asp Val Leu Asp Leu Glu Gln Leu Asp Leu Thr Gly Glu
                580                 585                 590
Pro Ala Glu Asn Pro Val Thr Glu Thr Thr Ser Thr Glu Leu Ala Tyr
            595                 600                 605
Ala Ile Tyr Thr Ser Gly Thr Thr Gly Lys Pro Lys Ala Val Leu Val
        610                 615                 620
Ser His Gly Ser Val Asp Ser Phe Arg Ala Gln Leu Ser Gly Arg Tyr
625                 630                 635                 640
Phe Gly Ser Pro Asp Glu Ser Ala Glu Ala Val Leu Phe Leu Ala Asn
                645                 650                 655
Tyr Val Phe Asp Phe Ser Val Glu Gln Leu Ala Leu Ser Val Leu Gly
            660                 665                 670
Gly His Lys Leu Leu Val Pro Pro Ser Ala Ala Asp Asp Pro Ala
        675                 680                 685
Phe Tyr Glu Leu Ala Asn Arg Glu Gly Leu Ser Tyr Leu Ser Gly Thr
    690                 695                 700
Pro Thr Gln Val Glu Arg Phe Asp Leu Ala His Leu Ser His Leu Arg
705                 710                 715                 720
Cys Val Leu Val Ala Gly Glu Ala Phe Gln Pro Gln His Phe Glu Lys
                725                 730                 735
Met Arg Gly Glu Phe Ala Gly Pro Ile Leu Asn Ala Tyr Gly Thr Thr
            740                 745                 750
Glu Thr Thr Val Tyr Asn Thr Val His Arg Phe Glu Pro Gly Asp Ala
        755                 760                 765
Tyr Arg Asn Thr Leu Gly Ala Pro Leu Gly Asn Thr Arg Leu Tyr Val
    770                 775                 780
Leu Gly Asp Gly Met Lys Leu Leu Pro Thr Gly Ala Val Gly Glu Leu
785                 790                 795                 800
Tyr Leu Ala Gly Asp Cys Val Thr Glu Gly Tyr Leu His Arg Pro Glu
                805                 810                 815
Leu Thr Arg Glu Arg Phe Leu Pro Asn Pro Phe Ala Ala Glu Ser Gly
            820                 825                 830
Arg Phe Pro Met Ile Tyr Arg Thr Gly Asp Val Val Arg Arg Gly Pro
        835                 840                 845
Asp Gly Glu Leu Gln Tyr Leu Gly Arg Asn Asp Ala Gln Val Lys Ile
    850                 855                 860
Asn Gly Leu Arg Ile Glu Pro Gly Glu Val Glu Ala Ala Leu Ala Gly
865                 870                 875                 880
Cys Ser Gly Val Arg Gln Cys Ala Val Val Ala Gly Ala Asp Pro Gln
                885                 890                 895
Ala Pro Glu Arg Lys Arg Leu Val Gly Tyr Tyr Leu Pro Glu Pro Gly
            900                 905                 910
Ala Ala Val Asp Glu Ala Asp Leu Phe Ala Ala Leu Arg Ala Gln Leu
        915                 920                 925
Met Pro Ser Met Val Pro Ser Leu Leu Val Arg Leu Asp Arg Pro Leu
    930                 935                 940
Pro Met Thr Ile Thr Gly Lys Leu Asp Val Asp Ala Leu Pro Ser Ala
945                 950                 955                 960
Asp Phe Ser Pro Lys Arg Ala Ala Tyr Ala Ala Pro Arg Asp Arg Val
                965                 970                 975
Glu Ala Arg Leu Cys His Leu Trp Ser Ala Gln Leu Pro Gly Gly Thr
            980                 985                 990
```

-continued

```
Val Gly Ile Asp Asp Asp Phe Phe Arg Cys Gly Gly Asp Ser Ile Ser
        995                 1000                1005

Ala Leu His Leu Ala Ser Gln Val Gln Arg Glu Ile Glu Arg Lys
    1010                1015                1020

Val Ser Val Lys Tyr Leu Phe Asp His Pro Thr Val Arg Ser Phe
    1025                1030                1035

Val Asp Asn Val Leu Ser Gly Leu Ala Glu Ser Ser Gly Asp Asp
    1040                1045                1050

Glu Pro Glu Gln Gly Arg Leu Thr Gly Glu Cys Pro Met Leu Pro
    1055                1060                1065

Ile Gln Glu Trp Phe Ala Lys Pro Leu Ala Asp Arg His Arg
    1070                1075                1080

Trp Asn His Asn Phe Ala Ile Arg Thr Pro Pro Leu Asp Pro Gly
    1085                1090                1095

Glu Leu Arg Thr Ala Leu Asp Arg Leu Val Glu His His Asp Ala
    1100                1105                1110

Phe Arg Leu Arg Phe Pro Glu Ser Gly Gly Gln Val Tyr Ala Glu
    1115                1120                1125

Asp Ala Ala Pro Ile Thr Leu His Glu Leu Asp Val Arg Gly Leu
    1130                1135                1140

Ala Asp Ala Asp Leu Arg Gln Arg Leu Val Asp Trp Gln Arg Thr
    1145                1150                1155

Phe Asp Leu Ala Asn Gly Pro Thr Ala Cys Ala Ala Tyr Leu His
    1160                1165                1170

Gly Phe Asp Asp Gly Thr Ala Arg Val Trp Phe Ala Leu His His
    1175                1180                1185

Leu Val Val Asp Thr Val Ser Trp His Ile Leu Ala Gln Asp Leu
    1190                1195                1200

Glu Ile Leu Tyr Asn Gly Gly Asp Leu Gly Ala Lys Thr Gly Ser
    1205                1210                1215

Tyr Arg Gln Trp Ala Gln Ala Val Arg Asp Tyr Thr Pro Ala Glu
    1220                1225                1230

Gly Glu Arg Glu Phe Trp Ala Glu Thr Thr Arg Asp Met Glu Ser
    1235                1240                1245

Ala Glu Leu Leu Ala Gln Thr Glu Gly Thr Thr Arg Arg Arg Glu
    1250                1255                1260

Glu Phe Ala Leu Thr Ala Pro Asp Thr Arg Thr Leu Leu Ala Glu
    1265                1270                1275

Ser Pro Trp Ala Tyr Asp Thr Glu Val Asn Asp Leu Leu Leu Thr
    1280                1285                1290

Ala Thr Gly Ser Ala Leu Arg Ser Ile Thr Arg Gln Ala Thr Asn
    1295                1300                1305

His Leu Thr Val Glu Gly His Gly Arg Glu Leu Phe Glu Gly Ala
    1310                1315                1320

Pro Asp Val Arg Asp Thr Val Gly Trp Phe Thr Thr Met His Pro
    1325                1330                1335

Phe Ala Val Glu Val Asp Pro Gly Asp Leu Gly Arg Ser Val Leu
    1340                1345                1350

Ala Thr Arg Ala Asn Arg Arg Arg Val Pro His His Gly Ile Gly
    1355                1360                1365

Tyr Gly Ala Leu Phe Gly Gly Glu Ala Pro Leu Pro Ala Val Ser
    1370                1375                1380

Phe Asn Tyr Leu Gly Arg Leu Gly Glu Gly Asp Gly Gln Pro Thr
    1385                1390                1395
```

```
Glu Ala Trp Gln Leu Asp Pro Ala Leu Ser Gly Ser His Thr Val
    1400                1405                1410

Asp Gly Asn Arg Leu Ala Asn Arg Ser Ser Ile Asp Val Thr Met
    1415                1420                1425

Ser Cys Thr Gly Gly Arg Leu Val Ala Val Val Asp Ser Leu Leu
    1430                1435                1440

Gly Glu Ala Ala Thr Arg Leu Phe Ala Ser Glu Leu Lys Val Trp
    1445                1450                1455

Leu Glu Arg Leu Val Ser His Thr Ala Thr Val Ala Arg Asn Glu
    1460                1465                1470

Pro Ala Arg Glu Ala Thr Thr Glu Leu Phe Asp Pro Tyr Ile Leu
    1475                1480                1485

Val Asn Glu Asp Ala Glu Arg Thr Leu Phe Val Leu Pro Pro Gly
    1490                1495                1500

Glu Gly Gly Ala Glu Ser Tyr Leu Ser Asn Leu Ala Arg Gln Leu
    1505                1510                1515

Pro Asp Leu Arg Leu Val Leu Phe Asn Asn Val His Leu His Thr
    1520                1525                1530

Pro Met Gly Ser Phe Glu Glu Leu Gly Arg Tyr Tyr Val Glu His
    1535                1540                1545

Ile Arg Arg Leu Gln Pro Ser Gly Pro Tyr His Leu Leu Gly Trp
    1550                1555                1560

Ser Phe Gly Gly Val Leu Ser Leu Glu Ile Ser Arg Gln Leu Ala
    1565                1570                1575

Arg Ala Gly Glu Arg Ile Asp Asp Leu Leu Leu Ile Asp Pro Tyr
    1580                1585                1590

Phe Gly Met Arg Gln Ala Ser Ala Asn Ile Gly Leu Pro Gly Val
    1595                1600                1605

Glu Asp Ile Leu Asp Pro Ile Asn Tyr His Tyr Arg Pro Asp Glu
    1610                1615                1620

Ala Asp Leu Ala Arg Leu Ala Gly Arg Leu Gly Asn Leu Val Leu
    1625                1630                1635

Phe Lys Ala Gly Glu Pro Asn Asp Val Val Asn Gly Pro His Gln
    1640                1645                1650

Pro Arg Leu Phe Glu Tyr Tyr His Gly Thr Arg Phe Asn His Leu
    1655                1660                1665

Asp Leu Leu Leu Pro Ala Ala Ile Glu Val Cys Asp Leu Ala
    1670                1675                1680

Gly Glu Thr His His Ser Trp Val Arg Asn Glu Lys Leu Val Arg
    1685                1690                1695

Leu Met Cys Glu Arg Ile Ser Thr
    1700                1705

<210> SEQ ID NO 11
<211> LENGTH: 5120
<212> TYPE: DNA
<213> ORGANISM: Nocardia lactamdurans

<400> SEQUENCE: 11
cgagcacacc gcgtggacgc cgccgcccac cgcggtcgag cacccgccgg tctcgctggc      60
gcaggaacgc ctgctgttca tcgacgactt cgaaggcggc acggcggcct acaacatccc     120
gttcgtgctc cggctgcccg cgcacacccg tgcgcgctc cccggtgcgc tgggcacgct     180
cgtgcgccgc cacccggccc tgcgcacgct gctgaagacc gacgaccagg gcgtgcggcg     240
```

```
gcagtacccg atcccggcgg acgacgtccg gctcgaggtc ccgtcgacca cagtggacag    300
ccgggccgag ctggacgagg tgctgaccga gcgcgccggg tacgtgttcc ggctgcacga    360
ggaactgccc atccgcgccg aagcgttcga ccacggcgac gagatctacc tcagcgtcgt    420
ggtgcaccac agctgcttcg acggctggtc gtgggacatc ttccgccgcg agctggcggc    480
cctgctcgac ggcgtccccg aagccgatct cggcgcgctg cgcggcacct acggcgagtt    540
cgcggtgtgg cagcggcagt acctgaccgg caagcggctg gccgcgctga ccagttctg     600 gaccggcgcg ctcggcggct tcgagaccat cgccctgccg ctggaccacc gcgcccgcc    660 gcggttcgac taccgcggcc gcgagctgga gttcgagctg gacgagcgga ccaccgaggc    720
gctgcgcgag ctggccagga ccgccagggt gagcctctac agcgtgctgc tcggcgcctg    780
gtgcctgatg ctcaacatgt acaccgggca gcacgacctc gtggtcggca cgccgtcggc    840
gaaccgcggc cgcccggagt cgacagggc ggtcggcttc ttcgcgaacc tgctcgccct    900
gcgggtccgc gtcgacccgg ccgcgaccct gccggcctac gtccggtcgg tcggcgaggc    960
ggtggtggcc gcgcaggtgc acggcgagct gccgttcgag cagctggtca aggaactcaa   1020
ggtggagaag gacccgagcc gtcacccgat cctgcagctc aacttcaccc tgcagaacgt   1080
ctccgaccac accagcgcgc tgaccgggta ccagccggac agcggtggct ggaccaccac   1140
caagttcgac ctgtccgcga cgatgaccga gaccgcgacc gggctggccg gcaacctgac   1200
ctacgccgcg tccctgttcg acgacaccag cgcgagcggg ttcatcgcca ccttcaagca   1260
cgtgctggcc gagttcgcct cggccgccgc gcagaccccg atcgcccagc tcaccgcgct   1320
cgacgagccg gggcaggcgg cgctgctgac gccaccccgcc gagcccgccg cccggcggac   1380
ccggacgctg cacgcggtct tcgaggaggt ggcggcgacc tggccggacc gggtcgccgt   1440
ggtccacggt gacgtgcggc tgacctaccg cgaattgaac gagcgggcca accgcctcgc   1500
ccaccacctg cggtcggtgg ccgaaccgcg ggccgacgag ctgatcgcgc tggtgctgga   1560
caagtccgag ctgaccctcg tggcgatcct cgcggtgtgg aaggccgggg cggcgtacat   1620
gccgatcgat ccgagctacc ccgacgaccg gatcgcgttc atgctgtccg acaccggcgc   1680
gaaactggtg ctcgccgggg aagcacacgg ctcgcgggtg cgcggcctga cctcgggcga   1740
cgtgctcgac ctcgaacagc tcgacctgac cggcgaaccc gcggagaacc cggtcaccga   1800
gaccaccagc accgaactgg cctacgcgat ctacacctcc ggcaccaccg gcaagcccaa   1860
ggcggtgctc gtctcgcacg gctcggtcga cagcttccgc gcgcagctga gcgggcgcta   1920
cttcggctcg ccggacgagt ccgccgaagc cgtgttgttc ctggcgaact acgtgttcga   1980
cttctccgtc gagcaactgg cgctgtcggt gctcggcggg cacaagctgc tcgtgccgcc   2040
gccctcggcc gccgacgatc cggcgttcta cgagctggcg aaccgcgagg tctgagcta    2100 cctcagcggt actccgacgc aggtggagcg cttcgacctg gcgcacctga gccacctgcg   2160
gtgcgtgctg gtcgccggtg aggcgttcca gccgcagcac ttcgagaaga tgcgcggcga   2220
gttcgccggg ccgatcctca cgcctacgg caccaccgaa accaccgtgt acaacaccgt    2280
gcaccgcttc gagcccggtg acgcctaccg gaacaccctc ggcgcgccgc tgggcaacac   2340
ccggctctac gtgctcggcg acgggatgaa gctgctgccc acgggcgcgg tcggcgagct   2400
gtacctggcg ggcgactgcg tgaccgaggg gtacctgcac cggcccgagc tgacccgcga   2460
gcggttcctg ccgaacccgt tcgcggcgga atccggccgg ttcccgatga tctaccgcac   2520
cggggacgtg gtccgccgcg gcccggacgg cgaactccag tacctgggcc gcaacgacgc   2580
ccaggtgaag atcaacggcc tgcggatcga gcccggcgag gtcgaagcgg cactggccgg   2640
```

```
ctgttccggc gtgcgccagt gcgcggtcgt cgcgggcgcg gacccgcagg cacccgagcg    2700
caaacggctc gtcggctact acctgcccga gcccggcgcg gccgtggacg aagccgacct    2760
cttcgccgcg ctgcgggcgc agctgatgcc gagcatggtg ccctcgctgc tggtgcggct    2820
cgatcgcccg ctgccgatga cgatcaccgg caagctggac gtggatgcct tgcccagcgc    2880
ggacttctcc ccgaagcggg cggcctacgc ggcccctcgt gaccgggtgg aagcgcggct    2940
gtgccacctg tggagcgcgc agctgccggg cggcacggtc ggcatcgacg acgacttctt    3000
ccgctgcggt ggcgacagca tcagcgcgct gcacctggcg agccaggtgc agcgggagat    3060
cgagcgcaag gtcagcgtca agtacctctt cgaccacccg accgtgcggt ccttcgtgga    3120
caacgtgctc tccggcctcg ccgagagctc cggcgacgac gaacccgagc agggcaggct    3180
gaccggcgag tgcccgatgc tgcccatcca ggagtggttc ttcgccaagc cgctggccga    3240
ccggcaccgc tggaaccaca acttcgccat ccggaccccg ccgctggacc ccggcgagct    3300
gcggaccgcg ctggaccggc tggtcgagca ccacgacgcc ttccggctgc ggttcccgga    3360
aagcggcggg caggtctacg ccgaggacgc cgcgccgatc accctgcacg agctcgacgt    3420
gcgcggcctg gccgacgccg acctgcggca gcgcctggtc gactggcagc gcaccttcga    3480
cctggcgaac gggccgacgg cctgtgcggc ctacctgcac gggttcgacg acggcaccgc    3540
acgggtctgg ttcgccctgc accacctcgt ggtggacacg gtgagctggc acatcctcgc    3600
ccaggacctg gaaatcctgt acaacggcgg cgacctgggc gcgaagaccg gcagctaccg    3660
gcagtgggcc caggcggtgc gcgactacac cccggccgag ggggagcgcg agttctgggc    3720
ggagaccacc cgggacatgg agtccgcgga actgctggcg cagaccgaag gcaccaccag    3780
gcgccgcgag gagttcgcgc tcaccgcccc ggacacgcgg acgctgctgg cggagagccc    3840
gtgggcctac gacaccgagg tcaacgacct gctgctgacc gcgaccggct ccgcgctgcg    3900
gtcgatcacc cggcaggcga cgaaccacct caccgtcgag ggccacgcc gcgagctgtt    3960 cgagggcgcg ccggacgtgc gggacaccgt cggctggttc accaccatgc acccgttcgc    4020
cgtcgaggtg gatcccggcg acctcgggcg cagcgtgctc gccaccaggg cgaaccggcg    4080
ccgggtgccg caccacggca tcggctacgg cgcgctcttc ggcggtgagg ccccgctgcc    4140
ggcggtcagc ttcaactacc tcggcaggct gggcgagggg gacgggcagc cgaccgaggc    4200
gtggcagctc gacccggcgt tgtccggcag ccacaccgtc gacggcaacc gcctggcgaa    4260
ccggtccagc atcgacgtga cgatgagctg caccggcggc cgcctggtcg cggtggtgga    4320
cagcctgctc ggcgaagcgg ccacgcgcct gttcgccagc gagctgaagg tgtggctgga    4380
gcggctggtc tcgcacaccg cgaccgtcgc ccgcaacgaa ccggcacgcg aagccaccac    4440
cgagctgttc gacccgtaca tcctggtcaa cgaggacgcc gagcgcacgc tcttcgtgct    4500
gccgccgggc gaaggcggcg cggagagcta cctgagcaac ctcgcgcggc agttaccgga    4560
cctgcggctc gtgctgttca acaacgtcca cctgcacacg cccatgggct cgttcgagga    4620
actggggcgc tactacgtcg agcacatccg gcggctgcag ccgtccgggc cgtaccacct    4680
gctcggctgg agcttcggcg gcgtgctgtc gctggagatc tcccggcagc tcgcgcgggc    4740
gggggagcgg atcgacgacc tgctgctgat cgacccgtac ttcgggatgc ggcaggcctc    4800
ggcgaacatc gggctgcccg gggtcgagga catcctcgac ccgatcaact accactaccg    4860
cccggacgag gccgacctcg cgcggctggc cgggcggctc gggaacctgg tgctgttcaa    4920
ggccggtgag ccgaacgacg tggtgaacgg cccgcaccag ccccggttgt tcgagtacta    4980
ccacgggacg cgcttcaacc acctcgacct gctgctgccc gcggccgcga tcgaggtctg    5040
```

```
cgacctggcc ggggagacgc accactcgtg ggtgcgcaac gagaagctgg tgcggctgat    5100
gtgcgagcgg atttcgacga                                                5120
```

<210> SEQ ID NO 12
<211> LENGTH: 28
<212> TYPE: DNA
<213> ORGANISM: Artificial Sequence
<220> FEATURE:
<223> OTHER INFORMATION: PCR primer

<400> SEQUENCE: 12

```
caccatggcg acgctgccgg aactgttc                                         28
```

<210> SEQ ID NO 13
<211> LENGTH: 34
<212> TYPE: DNA
<213> ORGANISM: Artificial Sequence
<220> FEATURE:
<223> OTHER INFORMATION: PCR primer

<400> SEQUENCE: 13

```
tcaattaatt aaccactcgg actcaaggtc ggac                                  34
```

<210> SEQ ID NO 14
<211> LENGTH: 34
<212> TYPE: DNA
<213> ORGANISM: Artificial Sequence
<220> FEATURE:
<223> OTHER INFORMATION: PCR primer

<400> SEQUENCE: 14

```
caccttaatt aatgaggaga atgcagcaac ggac                                  34
```

<210> SEQ ID NO 15
<211> LENGTH: 21
<212> TYPE: DNA
<213> ORGANISM: Artificial Sequence
<220> FEATURE:
<223> OTHER INFORMATION: PCR primer

<400> SEQUENCE: 15

```
tcaatagcga gcgaggtgtt c                                                21
```

<210> SEQ ID NO 16
<211> LENGTH: 31
<212> TYPE: DNA
<213> ORGANISM: Artificial Sequence
<220> FEATURE:
<223> OTHER INFORMATION: PCR primer

<400> SEQUENCE: 16

```
caccactagt ctggagtatc tctcatctat c                                     31
```

<210> SEQ ID NO 17
<211> LENGTH: 31
<212> TYPE: DNA
<213> ORGANISM: Artificial Sequence
<220> FEATURE:
<223> OTHER INFORMATION: PCR primer

<400> SEQUENCE: 17

```
caccttaatt aatgccgaag aggtcaccac c                                     31
```

<210> SEQ ID NO 18
<211> LENGTH: 17
<212> TYPE: DNA

```
<213> ORGANISM: Artificial Sequence
<220> FEATURE:
<223> OTHER INFORMATION: PCR primer

<400> SEQUENCE: 18
ggtcatcgct ccctagg                                                        17

<210> SEQ ID NO 19
<211> LENGTH: 28
<212> TYPE: DNA
<213> ORGANISM: Artificial Sequence
<220> FEATURE:
<223> OTHER INFORMATION: PCR primer

<400> SEQUENCE: 19
caccactagt ctcatctcac cgtcgatg                                            28

<210> SEQ ID NO 20
<211> LENGTH: 34
<212> TYPE: DNA
<213> ORGANISM: Artificial Sequence
<220> FEATURE:
<223> OTHER INFORMATION: PCR primer

<400> SEQUENCE: 20
caccttaatt aatagccagc aaccgacccg tgcg                                     34

<210> SEQ ID NO 21
<211> LENGTH: 29
<212> TYPE: DNA
<213> ORGANISM: Artificial Sequence
<220> FEATURE:
<223> OTHER INFORMATION: PCR primer

<400> SEQUENCE: 21
ttactagtgt cgcgggcgta cgcctcgtc                                           29

<210> SEQ ID NO 22
<211> LENGTH: 1531
<212> TYPE: DNA
<213> ORGANISM: Artificial Sequence
<220> FEATURE:
<223> OTHER INFORMATION: Hybrid nucleotide sequence

<400> SEQUENCE: 22
ggttaattaa tatcgaacat tgcgcagctc aagaacacat tcacctgacg ccaagcgata        60
tttcgctgaa ggacataaca atcgaggaat tagatcaatt tgttaagcaa acacagcata       120
tcggcgacat tgaaaatata tatccttttaa ctcccatgca gaaaggtatg ctgttccata      180
gtttaatcga ttcggcttcc agagcttact ttgaacaagc cgcttttgac ctcaaaggcg       240
acttggatat tgaggcattt acaatgagtt tgtcgtatct ggcggaaagc catgagattc       300
tccggactca ttttttatacg gaatggaaag atcagccttt gcagatcgta ttccgaaaaa      360
aaccgatcga aataaccgtt gaagatattc gaagcatgaa gaataaacaa cgaaacgagt       420
tcattgccgg ctttgtacaa aaagataagg caagaggatt cgaccttacc caagatgcgt      480
taatgcgcgt atcaatcctt cgtacagagg acgaccaagt ccgattgata tggagcttcc      540
atcatatttt aatggatggc tggtgtctgc ctcttattac gaaagaagtg tttgaaacct      600
attatgagct tcttgagaga agacaaccgg agcgggaagc cgtcaccccg tacagccgat      660
atatcgaatg gctggaagac caggatcatc agaacgcttt ggcctattgg caaaaatatt       720
tggacggtta tgaaggacaa accgttttac tgaaagaacc tgtctcaaac caagccaagg      780
```

```
gatatcaaaa acaaaggctt gcatgccggc tcggaaagca gctatcgaaa gaaatcagac      840
agactgcaag caagcatcac gtcaccgtga atacattcat tcaaagtgcg tgggggctat      900
tgctgcaaag atacaacaac agtcaggatg tcgttttcgg gtcggttgta tccggacgcc      960
cggcagaaat tccgggtatt gaatccatgg tcggcttatt tatcaacacc attcccgtac     1020
gtattaccgc tcagcctgga atgactgtgg aacaagtgtt gaaaatgagc caggagcagg     1080
cattggcttc tcaggcgtat gatacatttc cgttgtatga aattcaggct caaaccgaac     1140
aaaagcagca gctgatcagt catatcatgg tatttgaaaa ttatccggtc gagaaacaaa     1200
tggagcatat gaaaccgaat cgtgacgcgc tggacattat caatttccat atggaagagc     1260
atacccatta cgatttcaat ttcattgtca tgccggctgg agaaatcgac attcattttg     1320
tatacaatag caacgtctat gatcatgcaa gtgtcaagcg gatggaagag catttttatgc     1380 aaatcattaa gcagatggtg aacagtcagg cgattcgcgt ccaagacttg gatatactta     1440
cgggagatga acgttcgctc cttatagagg catttaatga tacggaagca gattatccaa     1500
aggaaaagac gcttcatcaa ttgactagta a                                    1531
```

<210> SEQ ID NO 23
<211> LENGTH: 1909
<212> TYPE: DNA
<213> ORGANISM: Artificial Sequence
<220> FEATURE:
<223> OTHER INFORMATION: Hybrid nucleotide sequence
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (175)..(175)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t

<400> SEQUENCE: 23

```
tcgagcggcc ggcgtattgg gtgttacgga gcattcacta ggcaaccatg catggttact       60
attgtatacc atcttagtag gaantgattt cgaggtttat acctacgatg aatgtgtgtc      120
ctgtaggctt gagagttcaa ggaagaaaca tgcaattatc tttgcgaacc caggngctgg      180
tgacggaatt ttcatagtca agctatcaga gtaaagaaga ggagcatgtc aaagtacaat      240
tagagacaaa tatatagtcg cgtggagcca agagcggatt cctcagtctc gtaggtctct      300
tgacgaccgt tgatctgctt gatctcgtct cccgaaaatg aaaatagctc tgctaagcta      360
ttcttctctt cgccggagcc tgnaaggcgt tactaggttg cagtcaatgc attaatgcat      420
tgcagatgag ctgtatctgg aagaggtaaa cccgaaaacg cgttttattc ttgttgacat      480
ggagctatta aatcactaga aggcactctt tgctgcttgg acaaatgaac gtatcttatc      540
gagatcctga acaccatttg tctcaactcc ggagctgaca tcgacaccaa cgatcttata      600
tccagattcg tcaagctgtt tgatgatttc agtaacgtta agtggatctc aagctcctgg      660
gacccgtggg ccgccgtcgg accggcggtg ttggtcggcg tcggtcagtc ctgctcctcg      720
gccacgaagt gcacgcagtt gccggccggg tcgcgcaggg cgaactcccg ccccacggc      780 tgctcgccga tctcggtcat ggccggcccg gaggcgtccc ggaagttcgt ggacacgacc      840
tccgaccact cggcgtacag ctcgtccagg ccgcgcaccc acaccaggc cagggtgttg      900 tccggcacca cctggtcctg gaccgcgctg atgaacaggg tcacgtcgtc ccggaccaca      960
```

```
ccggcgaagt cgtcctccac gaagtcccgg gagaacccga gccggtcggt ccagaactcg    1020
accgctccgg cgacgtcgcg cgcggtgagc accggaacgg cactggtcaa cttggccatg    1080
gtgatgtctg ctcaagcggg gtagctgtta gtcaagctgc gatgaagtgg gaaagctcga    1140
actgaaaggt tcaaaggaat aagggatggg aaggatggag tatggatgta gcaaagtact    1200
tacttagggg aaataaaggt tcttggatgg gaagatgaat atactgaaga tgggaaaaga    1260
aagagaaaag aaaagagcag ctggtgggga gagcaggaaa atatggcaac aaatgttgga    1320
ctgacgcaac gaccttgtca accccgccga cacaccgggc ggacagacgg ggcaaagctg    1380
cctaccaggg actgagggac ctcagcaggt cgagtgcaga gcaccggatg ggtcgactgc    1440
cagcttgtgt tcccggtctg cgccgctggc cagctcctga gcggcctttc cggtttcata    1500
caccgggcaa agcaggagag gcacgatatt tggacgccct acagatgccg gatgggccaa    1560
ttagggagct tacgcgccgg gtactcgctc tacctacttc ggagaaggta ctatctcgtg    1620
aatcttttac cagatcggaa gcaattggac ttctgtacct aggttaatgg catgctattt    1680
cgccgacggc tatacacccc tggcttcaca ttctccttcg cttactgccg gtgattcgat    1740
gaagctccat attctccgat gatgcaatag attcttggtc aacgaggggc acaccagcct    1800
ttccacttcg gggcggaggg gcggccggtc ccggattaat aatcatccac tgcacctcag    1860
agccgccaga gctgtctgga agcttctgca gacgcgtcga cgtcatatg               1909
```

<210> SEQ ID NO 24
<211> LENGTH: 25
<212> TYPE: DNA
<213> ORGANISM: Artificial Sequence
<220> FEATURE:
<223> OTHER INFORMATION: PCR primer

<400> SEQUENCE: 24
ttatcgattt gcataaaaaa cagac                                          25

<210> SEQ ID NO 25
<211> LENGTH: 26
<212> TYPE: DNA
<213> ORGANISM: Artificial Sequence
<220> FEATURE:
<223> OTHER INFORMATION: PCR primer

<400> SEQUENCE: 25
ttatcgatgc ttaccttcaa gcttcg                                         26

<210> SEQ ID NO 26
<211> LENGTH: 16
<212> TYPE: DNA
<213> ORGANISM: Artificial Sequence
<220> FEATURE:
<223> OTHER INFORMATION: PCR primer

<400> SEQUENCE: 26
gcctggtgcc tgatgc                                                    16

<210> SEQ ID NO 27
<211> LENGTH: 16
<212> TYPE: DNA
<213> ORGANISM: Artificial Sequence
<220> FEATURE:
<223> OTHER INFORMATION: PCR primer

<400> SEQUENCE: 27
ggtgtggtcg gagacg                                                    16

<210> SEQ ID NO 28
<211> LENGTH: 30
<212> TYPE: DNA
<213> ORGANISM: Artificial Sequence
<220> FEATURE:
<223> OTHER INFORMATION: PCR primer

<400> SEQUENCE: 28
caggaggaat tacatatgca gaatttcgag                                    30

<210> SEQ ID NO 29
<211> LENGTH: 30
<212> TYPE: DNA
<213> ORGANISM: Artificial Sequence
<220> FEATURE:
<223> OTHER INFORMATION: PCR primer

<400> SEQUENCE: 29
cggccaggga tgcatacgtc atcgccgagc                                    30

<210> SEQ ID NO 30
<211> LENGTH: 30
<212> TYPE: DNA
<213> ORGANISM: Artificial Sequence
<220> FEATURE:
<223> OTHER INFORMATION: PCR primer

<400> SEQUENCE: 30
caggaggaat tacatatgcc gcccagtgac                                    30

<210> SEQ ID NO 31
<211> LENGTH: 30
<212> TYPE: DNA
<213> ORGANISM: Artificial Sequence
<220> FEATURE:
<223> OTHER INFORMATION: PCR primer

<400> SEQUENCE: 31
gaattcccat atgcatccag gtcatcggcc                                    30

<210> SEQ ID NO 32
<211> LENGTH: 30
<212> TYPE: DNA
<213> ORGANISM: Artificial Sequence
<220> FEATURE:
<223> OTHER INFORMATION: PCR primer

<400> SEQUENCE: 32
caggaggaat tacatatgac caccaccacc                                    30

<210> SEQ ID NO 33
<211> LENGTH: 30
<212> TYPE: DNA
<213> ORGANISM: Artificial Sequence
<220> FEATURE:
<223> OTHER INFORMATION: PCR primer

<400> SEQUENCE: 33
tcccatatgc atcctcaacc gttagacgcc                                    30

<210> SEQ ID NO 34
<211> LENGTH: 30
<212> TYPE: DNA
<213> ORGANISM: Artificial Sequence
<220> FEATURE:
<223> OTHER INFORMATION: PCR primer

```
<400> SEQUENCE: 34
gtgaggtaac atatgagcca gaatctcttt                                  30

<210> SEQ ID NO 35
<211> LENGTH: 30
<212> TYPE: DNA
<213> ORGANISM: Artificial Sequence
<220> FEATURE:
<223> OTHER INFORMATION: PCR primer

<400> SEQUENCE: 35
gtaatcaatg catcactcat gcgtgtgttc                                  30

<210> SEQ ID NO 36
<211> LENGTH: 30
<212> TYPE: DNA
<213> ORGANISM: Artificial Sequence
<220> FEATURE:
<223> OTHER INFORMATION: PCR primer

<400> SEQUENCE: 36
caggaggaat tacatatgtc tatttatagc                                  30

<210> SEQ ID NO 37
<211> LENGTH: 38
<212> TYPE: DNA
<213> ORGANISM: Artificial Sequence
<220> FEATURE:
<223> OTHER INFORMATION: PCR primer

<400> SEQUENCE: 37
gtcctcggtc tcatgcatct cgagttagcc caggaggt                         38
```

PRODUCTION OF β-LACTAM ANTIBIOTICS

This application is the U.S. national phase of International Application No. PCT/EP2007/060460 filed 2 Oct. 2007 which designated the U.S. and claims priority to Application Nos. EP 06121817.8, filed 5 Oct. 2006 and EP 07113095.9, filed 25 Jul. 2007; the entire contents of each of which are hereby incorporated by reference.

FIELD OF THE INVENTION

The present invention relates to the production of β-lactam antibiotics.

BACKGROUND OF THE INVENTION

β-Lactam antibiotics are the largest family of secondary metabolites produced in nature by microorganisms. The most important classes of the β-lactam antibiotics both clinically and economically are the penicillins (penam) and cephalosporins (cephem). Their biosynthesis occurs via a complex pathway of enzymatic steps. The first two steps are the key steps in the biosynthetic pathways of the penam and cephem classes of β-lactam antibiotics. After these two steps the biosynthetic pathways to the penicillins and cephalosporins diverge. The first step in the biosynthesis of the penicillin, cephalosporin and cephamycin antibiotics is the condensation of the L-isomers of three amino acids, L-α-amino adipic acid (A), L-cystein (C) and L-valine (V) into a tripeptide, δ-(L-α-aminoadipyl)-L-cysteinyl-D-valine or ACV. This step is catalyzed by δ-(L-α-aminoadipyl)-L-cysteinyl-D-valine synthetase or ACVS. In the second step, the tripeptide ACV is oxidatively cyclised by the action of Isopenicillin N synthase (hereinafter referred to as IPNS) or cyclase. The product of this reaction is Isopenicillin N; this compound contains the typical β-lactam and thiazolidine ring structures and possesses antibacterial activity. From Isopenicillin N the penicillins G or V are formed by exchange of the hydrophilic α-aminoadipyl side chain by a hydrophobic side chain. The side chains commonly used in industrial processes are either phenylacetic acid (PA), yielding penicillin G, or phenoxyacetic acid (POA), yielding penicillin V; this exchange reaction is catalyzed by the enzyme acyltransferase (AT).

Due to the substrate specificity of the enzyme AT, it is not possible to exchange the α-aminoadipyl side chain for any side chain of interest, although it was shown that adipic acid and certain thio-derivatives of adipic acid could be exchanged (see WO 95/04148 and WO 95/04149). In particular, the side chains of industrially important penicillins and cephalosporins cannot be directly exchanged via AT. Consequently, most of the β-lactam antibiotics presently used are prepared by semi-synthetic methods. These semi-synthetic β-lactam antibiotics are obtained by modifying an N-substituted β-lactam product by one or more chemical and/or enzymatic reactions. These semi-synthetic methods have the disadvantage that they include many steps, are not environmentally friendly and are rather costly. It would therefore be highly desirable to avail of a completely fermentative route to β-lactam antibiotics, for instance to amoxicillin, ampicillin, cefadroxil and cefalexin.

Various options can be thought of for a completely fermentative route to semi-synthetic penam and cephem antibiotics.

For instance, one could focus at exchanging the α-aminoadipyl side chain of Isopenicillin N for the appropriate side chain of interest, e.g. the α-amino-p-hydroxyphenylacetyl side chain in case of amoxicillin. This would require modification of the substrate specificity of the enzyme AT, since the native enzyme has a rather narrow substrate specificity and is not capable of catalyzing such an exchange. In addition, this would require modification of the enzyme CoA ligase that activates the side chain to be exchanged.

Alternatively, one could focus at modifying the first two steps in the penicillin biosynthetic route in such a way that amoxicillin is directly synthesized and secreted. However, this would require substantial modification of the ACVS and IPNS enzymes.

For instance, for amoxicillin, it firstly would require the production of a tripeptide producing the amoxicillin side chain, i.e. the tripeptide D-p-hydroxyphenylglycyl-L-cysteinyl-D-valine, instead of ACV. Secondly, it would require an enzyme that is able to cyclise this tripeptide.

ACVS is a non-ribosomal peptide synthetase (NRPS) that catalyses the formation of the tripeptide LLD-ACV (δ-(L-α-aminoadipyl)-L-cysteinyl-D-valine). In this tripeptide, a peptide bond is formed between the δ-carboxylic group of L-α-aminoadipic acid and the amino group of L-cystein, and additionally the stereochemical conformation of valine is changed from L to D.

In recent years, several laboratories and institutions probed the options for the targeted engineering of NRPS. As main approaches, domains and modules were exchanged and as a consequence new specificities were introduced, leading to changed peptide products. In most cases, the engineering approaches were restricted to the enzyme fragments of the same organism (or even the same NRPS), severely limiting the options for enzyme engineering. A main problem of recent NRPS engineering addressed in the literature is the change of stereochemistry of an amino acid of the peptide, i.e. a change from L- to D- stereochemistry. A peptide bond-forming condensation domain immediately downstream of an epimerization domain is D-specific for the peptidyl or aminoacyl donor and L-specific for the amino acyl acceptor. Such a condensation domain is represented as $^{D}C_L$. An $^{L}C_L$ domain at this position does not yield condensation of the donor and acceptor moieties (Clugston S. L. et al. 2003, *Biochemistry*, 42, 12095-12104). A further problem that may limit options for engineering is that C and A domains are regarded as an inseparable couple (Mootz H. D. et al. 2000, *Proc. Natl. Acad. Sci. USA*, 97, 5848-5853).

It is now surprisingly found that engineering of ACVS is feasible to provide an engineered enzyme that is capable of catalysing the formation of a tripeptide HpgCV or PgCV, wherein in the N-terminal peptide bond an α-carboxylic group is used instead of the δ-carboxylic group that is used in the natural tripeptide ACV and, additionally, that is capable of modifying the L stereochemical configuration of the first amino acid to a D configuration.

Several groups have further investigated the substrate specificity of the enzyme IPNS. See for reviews on this topic Baldwin and Bradley, Chem. Rev. 1990, 90, 1079-1088 and Huffman et al. J. Med. Chem. 1992, 35, 1897-1914. For instance, a m-COOH-DL-phenylglycyl-L-cysteinyl-D-valine and a p-hydroxyphenylacetyl-L-cysteinyl-D-valine substrate were mentioned not to result in antibiotic activity (Huffman et al, supra).

It is also surprisingly found that the native enzyme IPNS is capable of acting on the tripeptides Hydroxyphenylglycyl-Cysteinyl-Valine (HpgCV) and Phenylglycyl-Cysteinyl-Valine (PgCV), more particularly on the DLD-variants of these tripeptides. The finding of this feature of IPNS opens up the road to further developments, among which the screening of IPNS variants to isolate IPNS molecules with an improved activity on these non-native peptides. The findings of the present invention for the first time enable a completely fermentative production of antibiotics that formerly could be obtained via semi-synthetic ways only.

DETAILED DESCRIPTION OF THE INVENTION

Thus, in a first aspect, the present invention provides a process for the production of an N-α-amino-hydroxyphenylacetyl or an N-α-aminophenylacetyl β-lactam antibiotic comprising contacting a tripeptide hydroxyphenylglycyl-cysteinyl-valine (HpgCV) or a tripeptide phenylglycyl-cysteinyl-valine (PgCV) with an IPNS to effect formation of the N-α-amino-hydroxyphenylacetyl or the N-α-aminophenylacetyl β-lactam antibiotic.

The present invention surprisingly shows for the first time that the enzyme IPNS is able to convert the non-native tripeptide substrates HpgCV or PgCV, respectively, to β-lactam compounds with a N-α-amino-hydroxyphenylacetyl or an N-α-aminophenylacetyl side chain, respectively, such as amoxicillin or ampicillin, respectively.

According to the invention, an "IPNS enzyme" or an "enzyme with IPNS activity" is an enzyme that cyclises a tripeptide HpgCV or PgCV to a penam antibiotic molecule. Such IPNS enzymes typically have a degree of identity to the *Emericella (Aspergillus) nidulans* IPNS amino acid sequence of SEQ ID NO: 1 of at least 50%.

The amino acids hydroxyphenylglycine (Hpg) and phenylglycine (Pg) in these tripeptides may be in the D- as well as the L-form, but preferably are in the D-form. The hydroxyphenylglycine preferably is p-hydroxyphenylglycine.

The detection of this non-native tripeptide-cyclising activity of IPNS is done using a bioassay and/or using LC/MS analysis.

The development of the bioassay required various choices to be made. For instance, a suitable microorganism needed to be selected for testing of antibiotic activity. In addition, a suitable IPNS needed to be selected, since IPNS enzymes from different species appear to differ in specific activity and stability.

Now that the non-native tripeptide cyclising activity of IPNS as mentioned above has been detected, it is possible to optimise the reaction conditions and to screen IPNS variants for enzymes with improved specific activity and/or altered substrate specificity.

The in vitro cyclisation of the non-native tripeptide to give a penam antibiotic typically is done using the reaction conditions as mentioned below.

The pH of the reaction mixture may be between 6 and 8, using any suitable buffer. The reaction mixture should further contain a suitable amount of Fe(II) ions. Finally, presence of a reducing agent, for instance DTT or TCEP (Tris(2-carboxyethyl)phosphine), is necessary to keep the precursor tripeptide in a reduced state. Preferably, the precursor tripeptide is pretreated with such a suitable reducing agent.

Optionally, the formed penam antibiotic, such as amoxicillin or ampicillin, may be further converted to produce a cephem antibiotic compound. This conversion requires at least the enzyme expandase, for instance to form cefadroxil or cefalexin. Optionally, other cephem compounds may be formed by further enzyme conversions using for instance hydroxylase and acetyl transferase enzyme activities or hydroxylase and carbamoyl transferase enzyme activities. The enzymes necessary for these conversions are suitably obtainable from cephem-producing microorganisms, such as *Streptomyces clavuligerus, Nocardia lactamdurans* or *Acremonium chrysogenum*. See for a recent review Liras and Martin, International Microbiology (2006) 9: 9-19.

In a preferred embodiment of the invention, an IPNS enzyme is used as is described herein below.

In one embodiment, custom made HpgCV and PgCV tripeptides are used as starting compounds in the process. In another embodiment, the tripeptides HpgCV and PgCV are produced in a process comprising i) contacting the amino acids hydroxyphenylglycine (Hpg) or phenylglycine (Pg), cystein (C) and valine (V) with a non-ribosomal peptide synthetase (NRPS) to effect formation of the tripeptide hydroxyphenylglycyl-cysteinyl-valine (HpgCV) or phenylglycyl-cysteinyl-valine (PgCV).

The NRPS for use in this embodiment is a non-natural NRPS with a modular structure comprising three modules, a first module M1 specific for Hpg or Pg, a second module M2 specific for C and a third module M3 specific for V, as is described herein below.

The overall process for the production of an N-α-amino-hydroxyphenylacetyl or an N-α-aminophenylacetyl β-lactam antibiotic from its precursor amino acids thus comprises i) contacting the amino acids hydroxyphenylglycine (Hpg) or phenylglycine (Pg), cystein (C) and valine (V) with a non-ribosomal peptide synthetase (NRPS) to effect formation of the tripeptide hydroxyphenylglycyl-cysteinyl-valine (HpgCV) or phenylglycyl-cysteinyl-valine (PgCV), and ii) contacting said tripeptides with IPNS to effect formation of—the N-α-amino-hydroxyphenylacetyl or the N-α-aminophenylacetyl β-lactam antibiotic.

The processes may be performed in vivo using a suitably engineered microbial strain, as described herein below.

In a second aspect of the invention, variant IPNS polypeptides are provided that are modified as compared to a parent IPNS polypeptide and that have an improved cyclising activity on a tripeptide HpgCV or PgCV as compared to the parent IPNS.

An "improved activity" of a variant IPNS enzyme according to the invention is an activity that ensures the production of at least 2 times the amount of antibiotic activity from the precursor tripeptide as compared to the parent IPNS, preferably at least 5 times the amount, more preferably at least 10 times the amount. If the parent IPNS has an undetectable activity on the precursor peptide, an improved activity encompasses any measurable activity above the detection limit.

Suitable positions for modification in a parent IPNS may be selected based on the criteria of a) creating space in the active center, and/or b) weakening of the binding of the C-terminus to the active site. The C-terminus of the IPNS molecule acts as a quasi-substrate when the enzyme is not loaded with a substrate and thus competes with the substrate for active site binding. Upon approach of the substrate to the active center, the C-terminus withdraws, creating space for the substrate. It may thus be beneficial to shift this competition in favour of the binding of the substrate.

The parent IPNS may originate from any suitable microbial source, as mentioned herein below.

A particular variant IPNS enzyme of the invention, when aligned to an IPNS of SEQ ID NO: 1, is modified as compared to a parent IPNS enzyme in at least one of the positions 75, 91, 183, 185, 287, 321, 324, 331, and is capable of converting the tripeptide HpgCV or PgCV, respectively, to the antibiotic amoxicillin or ampicillin, respectively. Modifications at these positions create more space in the peptide side chain binding pocket to accommodate the more bulky Hpg and Pg side chains of the HpgCV and PgCV tripeptides as compared to the linear and flexible α-amino-adipyl side chain of ACV. A preferred variant contains a modification on all of the above positions. Preferred modifications at these positions are the modifications 75LVT, 91FH, 183ACGTVL, 185STGAC, 287HSDQMK, 321FSAVTQEM, 324NDSTVA, 331GAS-CVDN. Especially preferred modifications are 75VT, 183AG, 185GA, 287HQ, 321AVTM, 324NSA, 331ASVDN.

A modification may be a substitution of a particular amino acid at the indicated position(s) for a different amino acid, may be an insertion of an amino acid at the indicated position(s) or may be a deletion of an amino acid from the indicated position(s).

Another particular variant IPNS enzyme of the invention, when aligned to an IPNS of SEQ ID NO: 1, is modified as compared to a parent IPNS enzyme in at least position 185, and optionally in at least one of the following positions, using the position numbering of SEQ ID NO: 1: 91, 104, 183, 190, 321, 324, 325, 331, and is capable of converting the tripeptide HpgCV or PgCV, respectively, to the antibiotic amoxicillin or ampicillin, respectively. Modifications at these positions shift the competition between the substrate and IPNS —C-terminal residues -Q330-T331 for binding in the active site in favour of the substrate by weakening the binding of the C-terminus to the active site and/or by stabilising the conformation in which the active site is available for substrate binding. It was surprisingly shown that the modification in at least position 185 confers a highly improved cyclisation activity to the IPNS enzyme containing the modification as compared to a parent IPNS not containing the modification.

A preferred variant according to the invention comprises the modification 185RKH, more preferably the modification 185RK, most preferably the modification 185R. The original amino acid at position 185 depends on the parent IPNS that is used, for instance may be S, T or V.

In one embodiment, the 185RKH modification is combined with a modification in at least one of the positions 91, 104, 183, 190, 321, 324, 325, 331, as mentioned in the table below. In particular, R and K can interact favourably with the C-terminal T331 when the C-terminal region N-G-Q-T331 has adopted the active conformation. Surprisingly, the interaction between 185RK and T331 is very beneficial for increasing the activity for HpgCV and PgCV. Likely 185RK favours the formation of the active conformation using HpgCV and PgCV as substrates.

| Native* | Preferred modifications | Particularly preferred modifications |
|---|---|---|
| Y91 | H F | F |
| C104 | A V S T L I | V T L I |
| 183 | A C V T L I | A C T |
| P190 | G A V N D Q E S T K R Y | A V S T |
| 321 | A I M Q | A M Q |
| L324 | N D S T V A | N D |
| I325 | A L N Q E M | L M Q |
| T331 | G A V S C | C S |

*At those positions where an amino acid is specified, the particular amino acid is conserved within all native IPNS enzymes known to date.

In the present invention, a denotation like e.g. "185RK" means that the amino acid in position 185 of the parent IPNS in question is substituted with either R or K, or that at position 185 of the parent IPNS either R or K are inserted when in the parent IPNS no amino acid is present at this position. The nature of the original amino acid residue will depend on the parent IPNS that is used. A denotation like e.g. "VST185RK" means that a specific amino acid residue at position 185 present in the parent IPNS, in this example V, S or T, is substituted for a different amino acid, in this example R or K.

A suitable parent IPNS is an IPNS polypeptide obtainable from a fungal or bacterial organism capable of producing β-lactams. A preferred parent IPNS is an IPNS obtainable from *Cephalosporium acremonium, Penicillium chrysogenum, Aspergillus (Emericella) nidulans, Streptomyces jumonjinensis, Nocardia lactamdurans, Streptomyces microflavis, Lysobacter lactamgenus, Flavobacterium* species, *Streptomyces clavuligerus, Streptomyces griseus* and/or *Streptomyces cattleya*. An especially preferred parent IPNS is obtainable from *Streptomyces clavuligerus* and/or *Aspergillus (Emericella) nidulans*. Typically, such a parent IPNS is a polypeptide with IPNS activity that has a degree of identity of at least 50%, preferably at least 55%, more, preferably at least 60%, more preferably at least 65%, more preferably at least 70%, more preferably at least 75%, or most preferably at least 80% to the amino acid sequence of SEQ ID NO: 1.

In addition to the modifications as set out above, preferably the modification 185RKH, the IPNS polypeptide may comprise additional modifications that concern positions in the polypeptide wherein a modification does not substantially affect the folding or activity of the polypeptide. Typically, such modifications may be conservative modifications, for instance substitutions wherein a non-polar, polar uncharged, polar charged or aromatic amino acid is substituted for a different amino acid from the same category, or may be due to intra-strain or intra-species variation. Polypeptides having such additional modifications typically have a degree of identity to the sequence of SEQ ID NO: 1 of at least 50%.

Thus, in one embodiment, the polypeptide having IPNS activity and comprising at least one of the modifications as set out above has a degree of identity of at least 50%, preferably at least 55%, more, preferably at least 60%, more preferably at least 65%, more preferably at least 70%, more preferably at least 75%, or most preferably at least 80% to the amino acid sequence of SEQ ID NO: 1.

The terms "homology" or "percent identity" are used interchangeably herein. For the purpose of this invention, it is defined here that in order to determine the percent identity of two amino acid sequences, the sequences are aligned for optimal comparison purposes (e.g., gaps can be introduced in each sequence for optimal alignment). The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences (i.e., % identity=number of identical positions/total number of positions (i.e. overlapping positions including gaps)×100). Preferably, the two sequences are the same length.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the Accelrys GCG software package (available at http[colon]slash][slash]www[dot]accelrys[dot]com[slash]products[slash]gcg[slash]), using either a Blossom 62 matrix or a PAM250 matrix, and a gap weight of 16, 14, 12, 10, 8, 6, or 4 and a length weight of 0.5, 1, 2, 3, 4, 5, or 6. The skilled person will appreciate that all these different parameters will yield slightly different results but that the overall percentage identity of two sequences is not significantly altered when using different algorithms. Preferably, the matrix is a Blossom 62 matrix with a gap weight of 10.0 and a length weight of 0.5.

The protein sequences of the present invention can further be used as a "query sequence" to perform a search against public databases to, for example, identify other family members or related sequences. Such searches can be performed using the blastp, psi-blast, phi-blast and tblastn programs (version 2.0) of Altschul, et al. (1990) J. Mol. Biol. 215:403-10. When utilizing blastp, psi-blast, phi-blast and tblastn programs, the default parameters of the respective programs (e.g., blastp, psi-blast, phi-blast and tblastn programs) can be used. See the homepage of the National Center for Biotechnology Information at www[dot]ncbi[dot]nlm[dot]nih[dot]gov.

In a third aspect, a polypeptide is provided that is a Non-Ribosomal Peptide Synthetase comprising three modules, a first module M1 specific for Hpg or Pg, a second module M2 specific for C and a third module M3 specific for V. With the term "specific for" an amino acid to characterise a module is meant that the particular module enables incorporation of the indicated amino acid. The first module M1 enables incorporation of a first amino acid L-p-hydroxyphenylglycine or L-phenylglycine and, preferably, its conversion to the corresponding D-amino acid. The second module M2 enables incorporation of the amino acid L-cystein while being coupled to the amino acid Hpg or Pg. In particular, when the amino acid Hpg or Pg is in its D-form, the M2 module specific for C comprises a $^DC_L$ domain that is fused to an A domain that is heterologous thereto. The third module M3 enables incorporation of the amino acid L-valine and its conversion to the corresponding D-amino acid. In this way, the peptide synthetase catalyzes the formation of a DLD-tripeptide Hydroxyphenylglycyl-Cysteinyl-Valine (HpgCV) or Phenylglycyl-Cysteinyl-Valine (PgCV) from its L-amino acid precursors Hpg or Pg, C and V.

The term "module" as used in the present invention defines a catalytic unit that enables incorporation of one peptide building block, usually an amino acid, in the product, usually a peptide, and may include domains for modifications like epimerisation and methylation.

Each module of an NRPS is composed of so-called "domains", each domain being responsible for a specific reaction step in the incorporation of one peptide building block. Each module at least contains an adenylation domain (A domain), responsible for recognition and activation of a dedicated amino acid, and a thiolation domain (T or PCP domain), responsible for transport of intermediates to the catalytic centers. The second and further modules further contain a condensation domain (C domain), responsible for formation of the peptide bond, and the last module further contains a termination domain (TE domain), responsible for release of the peptide. Optionally, a module may contain additional domains such as an epimerization domain (E-domain), responsible for conversion of the L-form of the incorporated amino acid to the D-form. See Sieber S. A. et al. 2005, Chem. Rev., 105, 715-738 for a review of the modular structure of NRPS.

A suitable source for the M1 module of the hybrid peptide synthetase is an NRPS enzyme catalyzing formation of a peptide comprising the amino acid X, wherein X is Hpg or Pg, to be incorporated as first amino acid in the XCV tripeptide. Thus, a suitable M1 module is selected taking into account the nature of the amino acid to be incorporated as first amino acid of the tripeptide. In particular, the A domain of a module determines selectivity for a particular amino acid. Thus, an M1 module may be selected based on the specificity of an A domain for the amino acid to be incorporated. Such a selection may occur according to the specificity determining signature motif of A domains as defined by Stachelhaus T. et al. 1999, Chem. & Biol., 8, 493-505.

The M1 module does not need to contain a C-domain and a TE domain, as being the first module of the NRPS. Thus, if present in the source module, a C and/or a TE domain may suitably be removed, to obtain a first module M1 without a C and/or a TE domain. In addition to an A and a T domain, the module M1 of the NRPS should contain an E-domain, if an L-amino acid needs to be converted to a D-amino acid. Thus, if not present in the source module, an E domain is fused to the T domain of the source module, to obtain a first module M1 containing an A, T and E domain.

In general, the specificity of module M1 of the NRPS for p-hydroxyphenylglycine or phenylglycine may be judged by experimental data and/or may be based on the specificity determining signature motif of A domains published by Stachelhaus T. et al. 1999, Chem. & Biol., 8, 493-505.

Preferably, a first module M1 with p-hydroxyphenylglycine specificity is obtainable from a CDA (Calcium-Dependent Antibiotic) Synthetase, in particular is the sixth module of a CDA synthetase (numeration of CDA Synthetase modules is given as published by Hojati Z. et al. 2002, Chem. & Biol., 9, 1175-1187). Preferably, the CDA synthetase is obtainable from Streptomyces coelicolor. Alternatively, Hpg-specific modules may be obtainable from a Chloroerenomycin Synthetase, in particular are the fourth and fifth module of a Chloroerenomycin Synthetase, preferably a Chloroerenomycin Synthetase obtainable from Amycolatopsis orientalis (Trauger J. W. et al. 2000, Proc. Nat. Acad. Sci. USA, 97, 3112-3117); or from a Complestatin Synthetase, in particular is the seventh module of a Complestatin Synthetase, preferably a Complestatin Synthetase obtainable from Streptomyces lavendulae (Chiu H. T. et al. 2001, Proc. Nat. Acad. Sci. USA, 98, 8548-8553). All these modules have specifity for L-Hpg and convert it into the D-stereoisomer.

Preferably, a first module M1 with phenylglycine specificity is obtainable from a Pristinamycin Synthetase, in particular is the C-terminal module of the SnbD protein of Pristinamycin Synthetase, as published in Thibaut, D. et al. 1997, J. Bact., 179, 697-704. Preferably, the Pristinamycin Synthetase is obtainable from Streptomyces pristinaspiralis.

The C-terminal source module from Pristinamycin Synthetase contains a TE domain and does not contain an E domain. To prepare a module functioning as a first module in the peptide synthetase of the invention, the TE domain suitably is removed from the C-terminal source module and an E domain is fused to the T domain of the thus—modified C-terminal module. An E domain may be obtainable from any suitable NRPS, for instance from another module of the same NRPS enzyme, or also from a module of a different NRPS enzyme with similar (e.g. p-hydroxyphenylglycine or phenylglycine) or different amino acid specificity of the adenylation domain. Preferably, the E domain is obtainable from a CDA Synthetase from Streptomyces coelicolor, preferably from the sixth module, as specified above. Thus, in this embodiment, the module M1 of the NRPS is a hybrid module.

The second module M2 of the peptide synthetase should enable incorporation of the amino acid cystein as second amino acid of the tripeptide DLD-XCV, wherein X is Hpg or Pg. Selection of this module may be based on the specificity determining signature motif of A domains as published by Stachelhaus T. et al. 1999.

To enable coupling of the L-cysteinyl acceptor to the D-X-aminoacyl donor, the C domain of the M2 module is a $^DC_L$ domain (as mentioned above and as explained in Clugston S. L. et al. 2003). This $^D C_L$ domain is fused to an A domain that is heterologous thereto. The term "heterologous" as used in this context means that the C and A domains are from different modules. These different modules may be from the same enzyme or may be from different enzymes. Preferably, the A domain is obtainable from the second module of an ACVS. Surprisingly, the hybrid M2 module comprising such a $^D C_L$-A domain configuration appears to be capable of incorporation of the amino acid cystein.

In a preferred embodiment, the $^D C_L$ domain of the M2 module is obtainable from the module immediately downstream of the module that is the source of the first module M1 of the peptide synthetase of the invention. For instance, the $^D C_L$ domain of the M2 module of the peptide synthetase is the $^D C_L$ domain of the seventh module of the CDA synthetase that is the source of the first module M1.

In another embodiment, the $^D C_L$ domain of the M2 module of the peptide synthetase is the $^D C_L$ domain of the second module of the *Bacillus subtilis* RB14 Iturin Synthetase Protein ItuC, as defined by Tsuge K. et al. 2001, *J. Bact.*, 183, 6265-6273.

In a preferred embodiment of the invention, the second module M2 of the peptide synthetase is at least partly obtainable from the enzyme that is the source of the third module M3 of the peptide synthetase. In particular, the A and T domains of the M2 module of the peptide synthetase are obtainable from the module immediately upstream of the module that is the source of the third module of the peptide synthetase of the invention. For instance, the A and T domains of the M2 module of the peptide synthetase may be the A and T domains of the second module of an ACVS.

The third module M3 of the peptide synthetase should enable incorporation of the amino acid valine as the third amino acid of the tripeptide, as well as its conversion to the D-form, to yield the tripeptide DLD-XCV.

In a preferred embodiment of the invention, the third module of the peptide synthetase is obtainable from an ACVS, in particular is the third module of an ACVS.

The ACVS as mentioned above preferably is a bacterial or fungal ACVS, more preferably a bacterial ACVS obtainable from *Nocardia lactamdurans* or a fungal ACVS obtainable from a filamentous fungus such as *Penicillium chrysogenum, Acremonium chrysogenum, Aspergillus nidulans*.

The modules M1, M2 and M3 of the peptide synthetase may have the amino acid sequences as shown below. However, these sequences are merely shown as examples and are not intended to limit the scope of the invention. The skilled person will appreciate that NRPS A domains for instance share about 30-60% amino acid sequence identity, even A domains with specificity for the same amino acid but from a different source, and comprise several core motifs among which a specificity determining signature motif (Stachelhaus T. et al. 1999).

The M1 module of the peptide synthetase for instance has an amino acid sequence according to SEQ ID NO: 2 or SEQ ID NO: 4 or an amino sequence with a percentage identity of at least 30%, more preferably at least 40%, even more preferably at least 50%, most preferably at least 60% to the amino acid sequence of SEQ ID NO: 2 or SEQ ID NO: 4. Such polypeptide modules with a percentage identity of at least 30% are also called homologous sequences or homologues.

The M2 module of the peptide synthetase for instance has an amino acid sequence according to SEQ ID NO: 6 or to SEQ ID NO: 8 or an amino sequence with a percentage identity of at least 30%, more preferably at least 40%, even more preferably at least 50%, most preferably at least 60%, to the amino acid sequence of SEQ ID NO: 6 or SEC ID NO: 8.

The M3 module of the peptide synthetase for instance has an amino acid sequence according to SEQ ID NO: 10 or an amino sequence with a percentage identity of at least 30%, more preferably at least 40%, even more preferably at least 50%, most preferably at least 60%, to the amino acid sequence of SEQ ID NO: 10.

The modules of the peptide synthetase may be obtained from natural NRPS enzymes as specified above or may de derived from such natural NRPS enzymes by mutagenesis techniques, such as random and/or site-directed mutagenesis and/or gene shuffling. If necessary, the source module may further be engineered to add necessary domains, delete unnecessary domains or substitute a domain for a corresponding domain from another module. Typically, the A domain of a module determines specificity for a particular amino acid, whereas E and C domains may be obtained form any module of choice. For instance, in a situation that the selected source module for incorporation of the first amino acid X is not a first module (M1 Module) in the source enzyme and thus comprises a C domain, the C domain of the source module may be deleted. In a situation that the source module does not contain an E domain while epimerization of the incorporated amino acid is desired, a suitable E domain may be added.

Engineered NRPS enzymes may be constructed by fusion of the appropriate domains and/or modules in the appropriate order. It is also possible to exchange a module or domain of an enzyme for a suitable module or domain of another enzyme. This fusion or exchange of domains and/or modules may be done using genetic engineering techniques commonly known in the art. Fusion of two different domains or modules may typically be done in the linker regions that are present in between modules or domains. See for instance EP 1 255 816 and Mootz H. D. et al. 2000 disclosing these types of constructions. Part or all of the sequences may also be obtained by custom synthesis of the appropriate polynucleotide sequence(s).

For instance, the fusion of an ATE tri-domain fragment from a Hpg-specific NRPS module to the bi-modular Cys-Val-specific fragment of an ACVS may be done as follows. The ATE fragment of a Hpg specific module may be isolated by restriction enzyme digestion of the corresponding NRPS gene at the linker positions, more specifically, between the C domain and the A domain of the Hpg specific module, in case of a C-terminal module or between the C domain and the A domain of the Hpg specific module and between the E domain and the subsequent domain (C or TE domain), in case of an internal elongation module. The bi-modular Cys-Val fragment of ACVS may be obtained by 1) leaving the C-terminus intact, and 2) exchanging the C domain of the Cys specific module 2 for a C-domain which has $^D C_L$ specificity. In analogy to isolation of the ATE fragment, an ATEC four-domain fragment may be isolated including the C domain of the adjacent downstream module. The latter is fused to the bi-modular Cys-Val fragment of ACVS without the upstream C domain.

The NRPS enzymes as described herein may be suitably subjected to mutagenesis techniques, e.g. to improve the catalytic properties of the enzymes.

Polypeptides as described herein may be produced by synthetic means although usually they will be made recombinantly by expression of a polynucleotide sequence encoding the polypeptide in a suitable host organism.

In a fourth aspect, polynucleotides (e.g. isolated and/or purified) are provided comprising a polynucleotide sequence encoding the variant IPNS or the NRPS polypeptides of the previous aspects of the invention. The polynucleotides of the present invention further include any degenerate versions of a polynucleotide sequence encoding the polypeptide. For example, the skilled person may, using routine techniques, make nucleotide substitutions that do not affect the protein sequence encoded in the polynucleotides of the invention to reflect the codon usage of any particular host organism in which the polypeptides of the invention are to be expressed. Preferably, coding sequences in the polynucleotides are optimized by codon-pair optimization.

The polynucleotide sequence of the invention may be RNA or DNA and includes genomic DNA, synthetic DNA or cDNA. Preferably, the polynucleotide is a DNA sequence.

The polynucleotides encoding the modules M1, M2 and M3 of the NRPS enzyme of the first aspect may for instance have a nucleotide sequence according to SEQ ID NO: 3, SEQ ID NO: 5, SEQ ID NO: 7, SEQ ID NO: 9 and SEQ ID NO: 11, encoding the amino acid sequences of SEQ ID NO: 2, SEQ ID NO: 4, SEQ ID NO: 6, SEQ ID NO: 8 and SEQ ID NO: 10, or may be nucleotide sequences encoding homologues of the above mentioned amino acid sequences, as defined above.

Polynucleotides may be synthesized according to methods well known in the art. They may be produced by combining oligonucleotides synthesized according to and along the nucleotide sequence of the polynucleotide of the invention. Alternatively, they may be synthesized by mutagenising a parental polynucleotide at any desired position. Polynucleotides may further be used to obtain polynucleotides encoding a further modified polypeptide, e.g. by subjecting polynucleotides to additional mutagenesis techniques.

Thus, polypeptides with improved activity typically are obtained by a method comprising the steps of subjecting a polynucleotide encoding the polypeptide to mutagenesis, screening the obtained population of variant polypeptides for desired activity and isolating variants with an improved activity.

The mutagenesis may be done using any suitable technique known to the person skilled in the art. The mutagenesis may encompass subjecting a polynucleotide to random mutagenesis as well as site-directed mutagenesis. When site-directed mutagenesis is used, it is preferably combined with saturation mutagenesis at the selected position(s), enabling the substitution of the original amino acid for any other amino acid. Polynucleotide shuffling (gene shuffling) technology (for instance as disclosed in WO95/22625, WO98/27230, WO98/01581, WO00/46344 and/or WO03/010183) may be used to obtain variants with a random combination of any variant position present in any member of a starting population of molecules. The starting population may further include one or more variants according to the invention.

The invention also provides vectors comprising a polynucleotide of the invention, including cloning and expression vectors or cassettes.

In an expression vector or cassette, the polynucleotide is operably linked to a regulatory sequence that is capable of providing for the expression of a polypeptide from its coding sequence by the host cell. The term "operably linked" refers to a juxtaposition wherein the components described are in a relationship permitting them to function in their intended manner. A regulatory sequence such as a promoter, an enhancer or another expression regulatory signal "operably linked" to a coding sequence is positioned in such a way that expression of a polypeptide from its coding sequence is achieved under conditions compatible with the regulatory sequences.

Promoters/enhancers and other expression regulatory signals may be selected to be compatible with the host cell for which the expression cassette or vector is designed. If the polypeptide is produced as a secreted protein, the polynucleotide sequence encoding a mature form of the polypeptide in the expression cassette is operably linked to a polynucleotide sequence encoding a signal peptide.

The DNA sequence encoding the polypeptide of the invention is preferably introduced into a suitable host as part of an expression cassette. For transformation of the suitable host with the expression cassette, transformation procedures are available which are well known to the skilled person. The expression cassette can be used for transformation of the host as part of a vector carrying a selectable marker, or the expression cassette may be co-transformed as a separate molecule together with the vector carrying a selectable marker. The vector may comprise one or more selectable marker genes.

For most filamentous fungi and yeasts, the expression construct is preferably integrated in the genome of the host cell in order to obtain stable transformants. In that case, the constructs are either integrated at random loci in the genome, or at predetermined target loci using homologous recombination.

Thus, a fifth aspect of the invention provides host cells transformed with or comprising a polynucleotide or vector of the invention.

Suitable host cells are host cells that allow for a high expression level of a polypeptide of interest. Such host cells are usable in case the polypeptides need to be produced and further to be used, e.g. in in vitro reactions. A heterologous host may be chosen wherein the polypeptide of the invention is produced in a form that is substantially free from other polypeptides with a similar activity as the polypeptide of the invention. This may be achieved by choosing a host that does not normally produce such polypeptides with similar activity.

Suitable host cells also are cells capable of production of β-lactam compounds, preferably host cells possessing the capacity to produce β-lactam compounds in high levels. The host cells may for example be prokaryotic (for example bacterial), fungal or yeast cells. The host may be selected based on the choice to produce a penam or a cephem compound. When production of a cephem compound is envisaged, the host may natively contain the necessary genes of the biosynthetic pathway leading to a cephem compound, in particular genes encoding expandase activity, and, optionally, hydroxylase and acetyl transferase activity. Alternatively, one or more genes of the biosynthetic pathway leading to a cephem compound may be transformed into a host cell devoid of these genes. It is thereby known to the skilled person that the enzymes expandase and expandase/hydroxylase are capable of expanding ampicillin and amoxicillin (Chin et al. 2003, FEMS Microbiol. Lett., 218, 251-257; Lloyd et al. 2004, J. Biol. Chem. 279, 15420-15426).

In one embodiment, a suitable host cell is a cell wherein the native genes encoding the ACVS and/or IPNS enzymes are inactivated, for instance by insertional inactivation. It is also possible to delete the complete penicillin biosynthetic cluster comprising the genes encoding ACVS, IPNS and AT. In this way the production of the β-lactam compound of interest is possible without simultaneous production of the natural β-lactam. Insertional inactivation may thereby occur using a gene encoding a NRPS and/or a gene encoding an IPNS as described above. In host cells that contain multiple copies of β-lactam gene clusters, host cells wherein these clusters are spontaneously deleted may be selected. For instance, the deletion of β-lactam gene clusters is described in patent application PCT/EP2007/054045.

Another suitable host cell is a cell that is capable of synthesising the precursor amino acids Hpg or Pg. Heterologous expression of the genes of the biosynthetic pathway leading to Hpg or Pg is disclosed in WO 02/34921. The biosynthesis of Pg or Hpg is achieved by withdrawing phenylpyruvate (PP) or p-hydroxyphenylpyruvate (HPP), respectively, from the aromatic amino acid pathway, converting PP or HPP to mandelic acid (MA) or p-hydroxymandelic acid (HMA), respectively, converting MA or HMA to phenylglyoxylate (PGL) or p-hydroxyphenylglyoxylate (HPGL), respectively, and finally converting PGL or or HPGL to D-Pg or D-Hpg, respectively. Example 15 exemplifies expression of the Hpg or Pg biosynthetic pathway in *Penicillium chrysogenum*.

Another suitable host cell is a cell that (over)expresses a 4'-phosphopantetheine transferase (PPTase). 4'-Phosphopantetheine (PPT) is an essential prosthetic group of amongst others acyl-carrier proteins of fatty acid synthases and polyketide synthases, and peptidyl carrier proteins of NRPS's. The free thiol moiety of PPT serves to covalently bind the acyl reaction intermediates as thioesters during the multistep assembly of the monomeric precursors, typically acetyl, malonyl, and aminoacyl groups. The PPT moiety is derived from coenzyme A (CoA) and posttranslationally transferred onto an invariant serine side chain. This $Mg^{2+}$-dependent conversion of the apoproteins to the holoproteins is catalyzed by the 4'-phosphopantetheine transferases (PPTases). It is advantageous to (over)express a PPTase with a broad substrate specificity. Such a PPTase is for instance encoded by the gsp gene from *Bacillus brevis* (Borchert et al. 1994, J. Bacteriology, 176, 2458-2462).

A host may suitably include one or more of the modifications as mentioned above. A preferred host is a strain of *Penicilium chrysogenum*.

In a further aspect the invention provides a process for preparing a polypeptide according to the invention by cultivating a host cell (e.g. transformed with an expression vector or cassette as described above) under conditions conducive to expression (by the vector or cassette) of the polypeptide according to the invention, and optionally recovering the expressed polypeptide. The polypeptide may be produced as a secreted protein in which case the polynucleotide sequence encoding a mature form of the polypeptide in the expression construct is operably linked to a polynucleotide sequence encoding a signal peptide. The polypeptide may also be produced as a fusion protein, i.e. fused to (part of) another polypeptide, for instance fused to maltose-binding protein.

For in vitro reactions, a secreted polypeptide or a cell-free extract comprising the polypeptide may be used. Optionally, the polypeptide may be (partially) purified prior to its use.

In a further aspect, the invention provides a process for preparing a β-lactam compound by cultivating a host cell of the previous aspect under conditions to provide for expression of the IPNS and/or NRPS polypeptide(s) as described herein and conducive to the production of a β-lactam compound, and optionally recovering the β-lactam compound. According to the invention, the β-lactam compound that is produced is an N-acylated β-lactam compound, wherein the N-acyl side chain is a N-α-aminohydroxyphenylacetyl or an N-α-aminophenylacetyl side chain. Advantageously, the present invention discloses the fully fermentative production of such β-lactam antibiotics. Examples of such β-lactam antibiotics are amoxicillin, ampicillin, cefadroxil and cefalexin.

The host cells according to the invention may be cultured using procedures known in the art. For each combination of a promoter and a host cell, culture conditions are available which are conducive to expression of the polypeptide of the invention. After reaching the desired cell density or titre of the polypeptide the culture is stopped and the polypeptide is recovered using known procedures. Additionally, fermentation conditions may be established conducive to the production of a β-lactam.

The fermentation medium may comprise a known culture medium containing a carbon source (e.g. glucose, maltose, molasses), a nitrogen source (e.g. ammonium sulphate, ammonium nitrate, ammonium chloride, organic nitrogen sources e.g. yeast extract, malt extract, peptone), vitamins, and other inorganic nutrient sources (e.g. phosphate, magnesium, potassium, zinc, iron, trace elements, etc.). Optionally, an inducer may be included.

The selection of the appropriate medium may be based on the choice of expression host and/or based on the regulatory requirements of the expression construct. Such media are known to those skilled in the art. The medium may, if desired, contain additional components favouring the transformed expression hosts over other potentially contaminating microorganisms. It may also be necessary to supplement the medium with precursor compounds for the β-lactam compounds to be produced. For instance, it may be necessary, depending on the host that is used, to include the amino acids Hpg or Pg in the culture medium. If so, these amino acids are preferably added as a separate feed.

The fermentation can be performed over a period of 0.5-30 days. It may be a batch, continuous or fed-batch process, suitably at a temperature in the range of between 0 and 45° C. and, for example, at a pH between 2 and 10. Preferred fermentation conditions are a temperature in the range of between 20 and 37° C. and/or a pH between 3 and 9. The appropriate conditions are usually selected based on the choice of the expression host and the protein and/or β-lactam compound to be expressed. After fermentation, if necessary, the cells can be removed from the fermentation broth by means of centrifugation or filtration. After fermentation has stopped and/or after removal of the cells, the polypeptide of the invention or the produced β-lactam compound may be recovered using conventional means. Recovery may include purification and/or extraction and/or crystallization steps.

Conveniently, the polypeptide of the invention or the β-lactam compound is combined with suitable (solid or liquid) carriers or diluents including buffers to produce a polypeptide or β-lactam compound composition. The polypeptide or the β-lactam compound may be attached to or mixed with a carrier, e.g. immobilized on a solid carrier. Thus the present invention provides in a further aspect a composition comprising a polypeptide of the invention or a β-lactam compound. This may be in a form suitable for packaging, transport and/or storage, preferably where the activity of the polypeptide is retained. Compositions may be of paste, liquid, emulsion, powder, flake, granulate, pellet or other extrudate form.

EXAMPLES

General Materials and Methods

Standard DNA procedures were carried out as described elsewhere (Sambrook, J. et al., 1989, *Molecular cloning: a laboratory manual*, $2^{nd}$ Ed., Cold Spring Harbor Laboratory Press, Cold Spring Harbor, N.Y.) unless otherwise stated. DNA was amplified using the proofreading enzyme Phusion polymerase (Finnzymes). Restriction enzymes were from Invitrogen or New England Biolabs. Fungal growth was performed in a mineral medium, containing (g/L): glucose (5); lactose (80); urea (4.5); $(NH_4)_2SO_4$ (1.1); $Na_2SO_4$ (2.9); $KH_2PO_4$ (5.2); $K_2HPO_4$ (4.8) and 10 mL/L of a trace element solution A containing citric acid (150); $FeSO_4.7H_2O$ (15); $MgSO_4.7H_2O$ (150); $H_3BO_3$ (0.0075); $CuSO_4.5H_2O$ (0.24);

CoSO$_4$.7H$_2$O (0.375); ZnSO$_4$.7H$_2$O (5); MnSO$_4$.H$_2$O (2.28); CaCl$_2$.2H$_2$O (0.99); pH before sterilization 6.5. As rich medium YEPD was used, containing (g/L): yeast extract (10); peptone (10); glucose (20). The cultures are incubated at 25° C. in an orbital shaker at 280 rpm for 72-168 h.

Penicillium chrysogenum transformations were carried out with the strain Wisconsin 54-1255 (ATCC 28089). Other strains of P. chrysogenum, including mutants of strain Wisconsin 54-1255, having an improved β-lactam yield, are also suitable. An example of such a strain is CBS 455.95. Furthermore, P. chrysogenum strains with mutations or deletions leading to absence or a decrease of β-lactam production are also suitable as transformation hosts, for instance strains wherein the β-lactam gene clusters are deleted as described in patent application PCT/EP2007/054045.

The transformation of P. chrysogenum was performed as described in WO2004/106347.

Example 1

Cultivation of Penicillium Chrysogenum and Analysis of Non-Natural Tripeptides such as DLD-Hpg-Cys-Val or DLD Pg-Cys-Val Penicillium chrysogenum was cultivated in mineral medium (25 mL) for 96 h at 25° C. Optionally, cultures were grown with or without amino acids such as L-Hpg (1 mM final concentration) or L-Pg (1 mM final concentration). At the end of the fermentation, the mycelium was removed by centrifugation or filtration and the mycelium was washed with physiological salt. Both the mycelium and the medium were assayed for tripeptides such as DLD-Hpg-Cys-Val and DLD-Pg-Cys-Val, using MS techniques such as LC-MS/MS. As standards, custom synthesized DLD-Hpg-Cys-Val and DLD-Pg-Cys-Val tripeptides were used. As a result, neither in the mycelium nor in the medium, tripeptides such as DLD-Hpg-Cys-Val and DLD-Pg-Cys-Val tripeptides were identified. As a conclusion, P. chrysogenum does not produce these non-natural tripeptides.

Example 2

Cloning of the Non-Ribosomal Peptide Synthetase Module and Domain Cassettes 2 a. Cloning of NRPS Module Fragments which Catalyze the Incorporation and Subsequent Epimerization of L-Hpg to D-Hpg Chromosomal DNA was isolated from Streptomyces coelicolor A3(2). Subsequently, PCR reactions were carried out, adding 3-8% DMSO to the reaction mixtures, furthermore, employing standard conditions. The following oligonucleotides were used: HpgFw1 (caccatggcgacgctgccggaactgttc; SEQ ID NO: 12) and HpgRev1 (tcaattaattaaccactc-ggact-caaggtcggac; SEQ ID NO: 13). The resulting PCR fragment Hpg1, yielding a ATE tridomain of module 6 of CDA I Synthetase from S. coelicolor, was cloned into a pENTR/SD/D-Topo vector (Invitrogen, The Netherlands), resulting in plasmid pHpg1.

2 b. Custom Synthesis of a Synthetic NRPS Module Fragment which Catalyzes the Incorporation and Subsequent Epimerization of L-Pg to D-Pg.

A synthetic DNA fragment consisting of the DNA sequence according to SEQ ID NO: 5 was custom-synthesized (DNA 2.0, Menlo Park, Calif., U.S.A.). The DNA fragment harbors a ATE tridomain. The AT fragment originated from the C-terminal module of the SnbD protein of S. pristinaspiralis Pristinamycin Synthetase, The E-domain was taken from the S. coelicolor CDA Synthetase module 6.

The DNA fragment was cloned into the vector pCR-Blunt (Invitrogen), using the Protocol delivered by the supplier, yielding vector pPg1.

2 c. Cloning of the Bi-Modular NPRS Fragments Specific for Cysteine and Valine Incorporation For this experiment, the genes of ACV ($\tilde{\delta}$(L-α-aminoadipate)-L-Cysteine, D-Valine) Tripeptide Synthetase from Penicillium chrysogenum and Nocardia lactamdurans were taken as templates. PCR amplifications using chromosomal DNA templates of either organism were carried out. For P. chrysogenum, the following oligonucleotides were employed: The oligo pair PcM2M3fw1 (caccttaattaatgag-gagaatgcagcaacggac; SEQ ID NO: 14) and PcM2M3rev1 (tcaatagcgagcgaggtgttc; SEQ ID NO: 15), resulting in Fragment PcM2M3__1 (domain organization CATCATETe), the oligo pair PcM2M3fw2 (caccactagtctggagtatctctcatctatc; SEQ ID NO: 16) and PcM2M3rev1 (tcaatagcgagcgaggtgttc; SEQ ID NO: 15), resulting in Fragment PcM2M3__2 (domain organization ATCATETe). Fragment PcM2M3__1 was cloned into pENTR/SD/D-Topo yielding pPcM2M3__1, and cloning of fragment PcM2M3__2 in the same vector gave plasmid pPcM2M3__2. In an analogues way, PCR amplifications with chromosomal DNA of Nocardia lactamdurans was carried out. Reactions using the oligonucleotides NIM2M3fw1 (caccttaattaatgccgaagaggtcaccacc; SEQ ID NO: 17) and NIM2M3rev1 (ggtcatcgctccctagg; SEQ ID NO: 18) gave DNA fragment NIM2M3__1 (domain organization CATCATETe), while reations with the oligos NIM2M3fw2 (caccactagtctcatctcaccgtcgatg; SEQ ID NO: 19) and NIM2M3rev1 (ggtcatcgctccctagg; SEQ ID NO: 18) resulted in fragment NIM2M3__2 (domain organization ATCATETe). Both fragments were finally cloned into pENTR/SD/D-Topo vectors, yielding plasmids pNIM2M3__1 and pNIM2M3__2, respectively.

2 d. Cloning of the NRPS Condensation Domain Fragment Specific for the Peptide Bond Formation between a D- and a L-Amino Acid Two different condensation domains with $^DC_L$ stereochemistry were cloned. The first domain was PCR-amplified from CDAI Synthetase using Streptomyces coelicolor chromosomal DNA, employing the oligo-nucleotides sc_C_fw (caccttaattaatagccagcaaccgacccgtgcg; SEQ ID NO: 20) and sc_C-rev (ttactagtgtcgcgggcgtacgcctcgtc; SEQ ID NO: 21), yielding fragment sc_C. The second fragment which consisted of a NRPS $^DC_L$ C-domain from the B. subtilis Iturin Synthetase ItuC module C2, according to SEQ ID NO: 22, was custom synthesized and named Bs_C. Both fragments were cloned into the vector pENTR/SD/D-Topo, resulting in the plasmids pSC_C and pBS_C, respectively.

Example 3

Construction of Tripeptide Non-Ribosomal Peptide Synthetase Genes by Fusion of the Cloned NRPS Module and Domain Cassettes The plasmid pHpg1 was digested with the restriction enzymes PacI and AscI, resulting in a 5.9 kb DNA fragment which contains the Hpg-specific NRPS module gene and most of the vector sequence. The plasmids pPcM1M2__1 was cut with AscI and PacI, showing a 8.5 kb DNA fragment. Ligation of this fragment and the 5.9 kb fragment from pHpg1 gave vector pSCPCHybrid1. Plasmids pPcM1M2__2, pSC_C were restricted with SpeI and AscI, resulting in 7.0 kb and 1.4 kb fragments, respectively. Both fragments were ligated and gave plasmid pPcM1M2_3. Plasmids pPcM1M2_3 and plasmid pHpg1 were cut with PciI and PacI, giving 12 kb and 4.5 kb DNA fragments, respectively. Ligation of both fragments resulted in the final construct pSC_SC_C_PCM2M3Hybrid1. Further restriction of pSC_SC_C_PCM2M3Hybrid1 and pBS_C with PacI and SpeI led to fragments of 16 kb (pSC_SC_C_PCM2M3Hybrid1 without the C-domain of module 2 of ACV Synthetase) and 1.4 kb (*Bacillus subtilis* C-domain), respectively. Ligation of both fragments gave plasmid pSC_BS_C_PCM2M3Hybrid2.

Restriction of pHpg1 and pNIM1M2_1 with PacI and AflII gave 3.7 kb and 8.8 kb DNA fragments. Ligation of both fragments yielded plasmid pSCNLHybrid1. Plasmids pSC_SC_C_PCM2M3Hybrid1 and pNIM1M2_2 were restricted with SpeI and AflII, resulting in 4 kb (ATEC tetradomain organization from Hpg module and (D)C(L) domain) and 7 kb (ATCATETe organization) fragments, respectively. Ligation of both fragments gave plasmid pSC_SC_C_NLM2M3Hybrid1. In analogy, plasmids pSC_BS_C_PCM2M3Hybrid1 and pNIM1M2_2 were restricted with SpeI and AflII, resulting in 4 kb (ATEC tetradomain organization from Hpg module and (D)C(L) domain) and 7 kb (ATCATETe organization) fragments, respectively. Ligation yielded plasmid pSC_BS_C_NLM2M3Hybrid2.

For the construction of a Phenylglycin specific Non-Ribosomal Peptide Synthetase fusion gene, the plasmids pPg1 and pSC_SC_C_NLM2M3Hybrid1 were restricted each with the restriction enzymes AflII and PacI. The 3.4 kb DNA fragment (harboring the ATE NRPS tridomain) of pPg1 was ligated into the 14 kb vector fragments obtained by restriction of pSC_SC_C_NLM2M3Hybrid1, resulting in plasmid pPg_SC_C_NIM2M3Hybrid1. In analogy, if vector pSC_SC_C_NLM2M3Hybrid1 was replaced by vector pSC_BS_C_NLM2M3Hybrid2, the resulting plasmid was pPg_BS_C_NIM2M3Hybrid2.

Example 4

Construction of a *Penicillium Chysogenum* Gateway® Expression Destination Vector for Hybrid-Non-Ribosomal Peptide Synthetases Plasmid pPT12, harboring the NotI-flanked Promotor-Terminator cassette from the IPN Synthase from *Penicillium chrysogenum*, was digested with NotI (for vector description, see Theilgaard et al. 2000, *Biotechnology and Bioengineering*, 72, 380-387). The so obtained IPNS Promoter-Terminator cassette was cloned into pBluescriptII SK (Stratagene, The Netherlands), that was also treated with NotI. Ligation led to pProduct1. Plasmid pProduct 1 was restricted with BamH1 and XhoI. Additionally, a DNA fragment which harbored a Phleomycin resistance cassette under the control of a gpdA promoter, was custom synthesized. The cassette has a sequence according to SEQ ID NO: 23.

After restriction of this custom synthesized DNA fragment with BamHI and XhoI the resulting DNA was ligated into the vector pProduct1 (which was opened with BamH1, XhoI). The resulting plasmid was named pProduct2. In a final cloning step, a DNA fragment containing a attR1-cat-ccdB-attR2 cassette (Chloramphenicol resistance and a toxicity gene for *E. coli*) was PCR-amplified from a Gateway® Destination vector such as pET-DEST42 (Invitrogen, Carlsbad, Calif., USA). The following oligo-nucleotides were used: fw: ttatcgatttgcataaaaaacagac (SEQ ID NO: 24), rev: ttatcgatgcttaccttcaagcttcg(SEQ ID NO: 25). The resulting DNA fragment was restricted with ClaI and subsequently cloned in pProduct2, which was previously opened by digestion with ClaI as well. Here, plasmids were screened which harbored the attR1-cat-ccdB-attR2 fragment in such an orientation that attR1 is fused next to the IPNS promoter $P_{IPNS}$. The resulting Gateway® destination vector was named pDEST-Pcexpr1.

Example 5

Construction of *P. Chrysogenum* Expression Constructs for Non-Ribosomal Peptide Synthetases For the construction of *P. chrysogenum* expression constructs, the Gateway® LR-Clonase reaction was carried out using standard conditions as described by Invitrogen. For detailed protocols, see manuals for the Gateway® technology at http[colon][slash][slash]www[dot]invitrogen[dot]com. For the reaction, the entry vectors pSCNLHybrid1, pSC_SC_C_NLM2M3Hybrid1 and pSC_BS_C_NLM2M3Hybrid2 were each incubated with the Gateway® destination vector pDEST-Pcexpr1. See table 1 for the resulting expression plasmid names.

Alternatively, for the construction of *P. chrysogenum* expression constructs, the constructs containing the engineered tripeptide NRPS-genes were functionally linked to the NotI-flanked promoter-terminator cassette from the pcbC-gene from *Penicillium chrysogenum* (for vector description, see Theilgaard et al. 2000, *Biotechnology and Bioengineering*, 72, 380-387) by fusion-PCR. See Table 1 for the resulting expression plasmid names.

TABLE 1

| ENTRY vector used in LR-Reaction | Resulting expression vector |
| --- | --- |
| pSCNLHybrid1 | pEXPR-NRPS4 |
| pSC_SC_C_NLM2M3Hybrid1 | pEXPR-NRPS5 |
| pSC_BS_C_NLM2M3Hybrid2 | pEXPR-NRPS6 |
| pPg_SC_C_NIM2M3Hybrid1 | pEXPR-NRPS7 |
| pPg_BS_C_NIM2M3Hybrid2 | pEXPR-NRPS8 |

Example 6

Transformation of *Penicillium Chrysogenum* with Linearized Plasmid pEXPR-NRPS4, Cultivation and Tripeptide Analysis In independent experiments, *Penicillium chrysogenum* was transformed with pEXPR-NRPS4 that was linearized prior to transformation with suitable enzymes that cut in the vector backbone, such as PsiI or PciI. Selection of transformants was done on mineral medium agar plates with 50 g/mL Phleomycin and 1M *Saccharose*. Phleomycin resistant colonies appearing on these protoplast regeneration plates were re-streaked on fresh phleomycin agar plates without the *saccharose* and grown until sporulation. The phleomycin resistant transformants were screened via colony PCR for the presence of the NRPS genes. For this, a small piece of colony was suspended in 50 L TE buffer (Sambrook et al., 1989) and incubated for 10 min at 95 C. To discard the cell debris, the mixture was centrifuged for 5 min at 3000 rpm. The supernatant (5 L) was used as a template for the PCR reaction with Super-Taq from HT Biotechnology Ltd. The PCR reactions were analyzed on the E-gel96 from Invitrogen.

The following oligo-nucleotides were used in the colony-PCR screen (see SEQ ID NO: 26 and SEQ ID NO: 27):

```
Transformed plasmid:         pEXPR-NRPS4
Oligo-nucleotides for colony Fw: GCCTGGTGCCTGATGC
PCR:                         Rev: GGTGTGGTCGGAGACG
```

The expected size of these PCR reactions was 303 bp.

The positive clones underwent one further purification step on fresh phleomycin agar plates without the saccharose. Subsequently, they were grown on mineral medium as described in "General Materials and Methods". Additionally, the amino acid L-Hpg (4-Hydroxyphenylglycine) or L-Pg (Phenylglycine) were added to a final concentration of 1 mM, depending on what tripeptide was analyzed. Cultivation was carried out on shake flask scale or on 24-well micro titer plates. At the end of the fermentation, the mycelium was removed by centrifugation or filtration and the mycelium was washed with physiological salt. Both the mycelium and the medium were assayed for tripeptides such as DLD-Hpg-Cys-Val (in case L-Hpg was added to the medium) and DLD-Pg-Cys-Val (in case L-Pg was added to the medium), using MS techniques such as LC-MS/MS. As standards, custom synthesized DLD-Hpg-Cys-Val and DLD-Pg-Cys-Val tripeptides were used. As a result, neither in the mycelium nor in the medium, tripeptides such as DLD-Hpg-Cys-Val and DLD-Pg-Cys-Val tripeptides were identified. As a conclusion, *P. chrysogenum* does not produce these un-natural tripeptides, if NRPS expression cassettes constructs such as pEXPR-NRPS4 were integrated.

Example 7

Transformation of *Penicillium Chrysogenum* with Linearized Plasmids pEXPR-NRPS5 and pEXPR-NRPS6, Cultivation and DLD-Hpg-Cys-Val Tripeptide Production In independent experiments, *Penicillium chrysogenum* was transformed with either pEXPR-NRPS5 or pEXPR-NRPS6 that were linearized prior to transformation with suitable enzymes that cut in the vector backbone, such as PsiI or PciI. The transformation of *P. chrysogenum* was carried out under conditions e.g. described in WO2004/106347. Selection of transformants was done on mineral medium agar plates with 50 g/mL Phleomycin and 1M *Saccharose*. Phleomycin resistant colonies appearing on these protoplast regeneration plates were re-streaked on fresh phleomycin agar plates without the saccharose and grown until sporulation. The phleomycin resistant transformants were screened via colony PCR for the presence of the NRPS genes. For this, a small piece of colony was suspended in 50 L TE buffer (Sambrook et al., 1989) and incubated for 10 min at 95 C. To discard the cell debris, the mixture was centrifuged for 5 min at 3000 rpm. The supernatant (5 L) was used as a template for the PCR reaction with Super-Taq from HT Biotechnology Ltd. The PCR reactions were analyzed on the E-gel96 from Invitrogen.

The following oligo-nucleotides were used in the colony-PCR screen (see SEQ ID NO: 26 and SEQ ID NO: 27):

```
Transformed plasmid     pEXPR-NRPS 5 or pEXPR-NRPS6
Oligo-nucleotides for   Fw: GCCTGGTGCCTGATGC
colony PCR              Rev: GGTGTGGTCGGAGACG
```

The expected size of these PCR reactions was 303 bp.

The positive clones underwent one further purification step on fresh phleomycin agar plates without the saccharose. Subsequently, they were grown on mineral medium as described in "General Materials and Methods". Additionally, the amino acids L-Hpg (4-Hydroxyphenylglycine) or L-Pg (Phenylglycine) were added to a final concentration of 1 mM, depending on what tripeptide was analyzed. Cultivation was carried out on shake flask scale or on 24-well micro titer plates. At the end of the fermentation, the mycelium was removed by centrifugation or filtration and the mycelium was washed with physiological salt. Both the mycelium and the medium were assayed for tripeptides such as DLD-Hpg-Cys-Val (in case L-Hpg was added to the medium) and DLD-Pg-Cys-Val (in case L-Pg was added to the medium), using MS techniques such as LC-MS/MS. As standards, custom synthesized DLD-Hpg-Cys-Val and DLD-Pg-Cys-Val tripeptides were used. The mycelium and the supernatant showed significant levels of the tripeptide DLD-Hpg-Cys-Val tripeptide. The negative control, for which an untransformed *P. chrysogenum* strain Wisconsin 54-1255 (ATCC 28089) was employed, showed no formation of DLD-Hpg-Cys-Val tripeptide. This result gives proof that the transformed engineered Non-Ribosomal Peptide Synthetases produce the unnatural tripeptide DLD-Hpg-Cys-Val.

Example 8

Transformation of *Penicillium Chrysogenum* with Linearized Plasmid pEXPR-NRPS7 and pEXPR-NRPS8, Cultivation and DLD-Pg-Cys-Val Tripeptide Production In independent experiments, *Penicillium chrysogenum* was transformed with either pEXPR-NRPS7 or pEXPR-NRPS8 that were linearized prior to transformation with suitable enzymes that cut in the vector backbone, such as PsiI or PciI. The transformation of *P. chrysogenum* was carried out under conditions e.g. described in WO2004/106347. Selection of transformants was done on mineral medium agar plates with 50 g/mL Phleomycin and 1M *Saccharose*. Phleomycin resistant colonies appearing on these protoplast regeneration plates were re-streaked on fresh phleomycin agar plates without the saccharose and grown until sporulation. The phleomycin resistant transformants were screened via colony PCR for the presence of the NRPS genes. For this, a small piece of colony was suspended in 50 L TE buffer (Sambrook et al., 1989) and incubated for 10 min at 95 C. To discard the cell debris, the mixture was centrifuged for 5 min at 3000 rpm. The supernatant (5 L) was used as a template for the PCR reaction with Super-Taq from HT Biotechnology Ltd. The PCR reactions were analyzed on the E-gel96 from Invitrogen.

The following oligo-nucleotides were used in the colony-PCR screen(see SEQ ID NO: 26 and SEQ ID NO: 27):

```
Transformed plasmid     pEXPR-NRPS 7 or pEXPR-NRPS8
Oligo-nucleotides for   Fw: GCCTGGTGCCTGATGC
colony PCR              Rev: GGTGTGGTCGGAGACG
```

The expected size of these PCR reactions was 303 bp.

The positive clones underwent one further purification step on fresh phleomycin agar plates without the saccharose. Subsequently, they were grown on mineral medium as described in "General Materials and Methods". Additionally, the amino acids L-Hpg (4-Hydroxyphenylglycine) or L-Pg (Phenylglycine) were added to a final concentration of 1 mM, depending on what tripeptide was analyzed. Cultivation was carried out on shake flask scale or on 24-well micro titer plates. At the end of the fermentation, the mycelium was removed by centrifugation or filtration and the mycelium was washed with physiological salt. Both the mycelium and the medium were assayed for tripeptides such as DLD-Pg-Cys-Val (in case L-Pg was added to the medium), using MS techniques such as LC-MS/MS. As standards, custom synthesized DLD-Hpg- Cys-Val and DLD-Pg-Cys-Val tripeptides were used. The mycelium and the supernatant showed significant levels of the tripeptide DLD-Pg-Cys-Val tripeptide. The negative control, for which an untransformed *P. chrysogenum* strain Wisconsin 54-1255 (ATCC 28089) was employed, showed no formation of DLD-Pg-Cys-Val tripeptide. This result gives proof that the transformed engineered Non-Ribosomal Peptide Synthetases produce the unnatural tripeptide DLD-Pg-Cys-Val.

Example 9

In Vitro Production of Amoxicillin by Conversion of DLD-HpgCV

Three different constructs, containing the pcbC-genes of *Penicillium chrysogenum* (pAJL-pcbC), *Nocardia lactamdurans* (pAJL-pcbC-NL) and *Aspergillus nidulans* (pXTN313) were inoculated from a glycerol stock and grown overnight at 37° C., in 2×TY and 35 μg chloroamphenicol per ml. The respective pcbC-genes encode IPNSs which are being produced as fusion proteins with MBP (maltose binding protein), encoded by the maE-gene from *Escherichia coli*. The malE-pcbC fusion genes are under control of the IPTG-inducible tac-promoter.

Plasmid DNA was isolated from the overnight cultures. The isolated DNA was used to transform *E. coli* TOP10 (Invitrogen). One isolated colony was used to inoculate 10 ml of 2×TY supplemented with 35 μg chloroamphenicol per ml. After O/N incubation at 37° C. and 280 rpm, the $OD^{600}$ was measured. The strains were diluted to 100 ml of fresh medium, to a final $OD^{600}$ of 0.015. Growth at 37° C. and 280 rpm was allowed until the $OD^{600}$ reached a value between 0.4 and 0.6. IPTG was added to a final concentration of 0.5 mM. The incubation was continued at 22° C. and 220 rpm, overnight.

Cells were harvested by centrifugation and washed with 0.9% NaCl in milliQ water. The cell pellets were resuspended in 1.5 ml extraction buffer (50 mM Tris.HCl pH 7.5; 0,5 mg lysozyme/ml, 5 mM DTT). Sonification was performed in order to lyse the cells. After centrifugation for 10 minutes at 14000 rpm in an Eppendorf centrifuge, 200 μl aliquots were collected and frozen in liquid nitrogen. The frozen cell free extracts were stored at –80° C.

IPNS activity assays were performed with ACV and HpgCV as substrates. Apart from the standard assay conditions for the IPNS activity assay, modifications were applied to the assay mix in order to maximize the chance of success.
Reaction Mixes Were as Follows:
Reaction Mix 1 (Standard Assay)
30-50 mM Tris.HCl pH 8.0 (preferably 36 mM)
1-6.7 mM ascorbate (preferably 3 mM)
50 μM to 2 mM $FeSO_4$ (preferably 86 μM)
0.3-2 mM tripeptide (preferably 1.5 mM for ACV and 0.75 mM for HpgCV)
0.75-4 mM DTT (preferably 3 mM)
The bis-ACV was reduced to ACV by mixing two aliquots of 7.5 mM bis-ACV with one aliquot of 60 mM DTT, followed by an incubation of 5 to 25 minutes at room temperature. Likewise, HpgCV was reduced prior to the actual assay.
Reaction Mix 2 (Alternative Assay)
30-50 mM HEPES pH 7.0 (preferably 36 mM)
0.1-0.2 mM ascorbate (preferably 0.1 mM)
1-50 μM $FeSO_4$ (preferably 25 μM)
0.3-2 mM tripeptide (preferably 1.5 mM for ACV and 1.5 mM for HpgCV)
0.2-1.2 mM TCEP (Tris(2-Carboxyethyl)phosphine) (preferably 1 mM)

Bis-ACV and HpgCV were pre-treated with TCEP in order to break S—S bonds in the dimers. To this end, two aliquots of 7.5 mM bis-ACV, or HpgCV, were mixed with one aliquot of 20 mM TCEP, followed by an incubation of 5 to 25 minutes at room temperature.

5 μl of the CFEs, containing the MBP-IPNS fusion proteins, were incubated with 595 μl of the reaction mixes mentioned above. After 10 minutes of incubation at 25° C., the reaction was stopped by adding 125 μl of the reaction with 50 μl ice-cold methanol. After incubation at –20° C. for at least one hour, the samples were analysed by LC/MS.

The LC/MS analysis was performed on an LCQ (Thermo Scientific), using the following settings:

| Eluents | Eluens A: 0.1% FA in MilliQ water | | | |
|---|---|---|---|---|
| | Eluens B: 0.1% FA in MilliQ water | | | |
| Gradient | T (min) | flow (ml/min) | % A | % B |
| | 0.0 | 0.2 | 98 | 2 |
| | 5.0 | 0.2 | 98 | 2 |
| | 20.0 | 0.2 | 78 | 22 |
| | 20.1 | 0.2 | 98 | 2 |
| | 30.0 | 0.2 | 98 | 2 |
| Column | Varian Inertsil 3 ODS 3 CP22568 150*2.1 mm 3 μm | | | |
| Column Temp. | 55° C. | | | |
| Flow | 0.2 ml/min | | | |
| Injection volume | 25 μl | | | |
| Tray Temp. | 4° C. | | | |
| Retention time: | | | | |
| IPN | Approx. 12.2 min | | | |
| Amoxicillin | Approx. 4.9 min | | | |
| Ampicillin | Approx. 16.5 min | | | |
| MS | | | | |
| Instrument | LCQ (SM05) | | | |
| LC/MS | OFF axis ESI/pos Probe height nr 6, depth nr 3 | | | |
| LC/MS/MS | 360 iw = 5.0 aa = 30% | | | |
| | 366 iw = 5.0 aa = 30% | | | |
| | 350 iw = 5.0 aa = 30% | | | |
| LC/MS/MS/MS | 349 iw = 5.0 aa = 30% | | | |
| m/z range | MS: 200-1000 | | | |
| micro scans | 1 | | | |
| inject time | 500 ms | | | |

The samples were diluted 10 times with milliQ water and 25 μl was injected into the LC/MS system.

Substrates (ACV, HpgCV, PgCV) and products (IPN, amoxicillin, ampicillin) were identified based on retention time (LC), the mass over charge (m/z) value (MS) as well as the fragmentation pattern upon fragmentation in the $MS^n$-mode.

The results are summarized in the table below.

TABLE 2

Conversion of the substrates ACV and HpgCV into IPN and amoxicillin respectively by the MBP-IPNS fusion proteins from different sources

| | ACV → IPN | | HpgCV → amoxicillin | |
|---|---|---|---|---|
| Origin pcbC-gene | Reaction mix 1 | Reaction mix 2 | Reaction mix 1 | Reaction mix 2 |
| *P. chrysogenum* | 16% | 50% | 0% | 0.0006% |
| *A. nidulans* | 36% | 98% | 0% | 0.0007% |
| *N. lactamdurans* | 36% | 99% | 0% | 0.0006% |

Surprisingly, under the experimental conditions of reaction mix 2, MBP-IPNS is capable of converting HpgCV into amoxicillin, while no amoxicillin is converted under the conditions of reaction mix 1.

Example 10

Development of a Bioassay Allowing the Detection of the Conversion of DLD-HpgCV to Amoxicillin The bacterial strains *Escherichia coli* ESS, *Bacillus subtilis* ATCC6633 and *Micrococcus luteus* ATCC9341 were grown overnight in 2×TY-medium at 30° C. and 280 rpm. After 16 hours of growth, the $OD^{600}$ was measured. Typically, the $OD^{600}$ amounts 5.0, ranging from 2.0 to 8.0.

A solution of amoxicillin was made at a concentration of 7 mg/ml. Subsequently, serial dilutions were made ranging from 1 mg/l down to 0.001 mg/l. MilliQ water served as a negative control.

In a 96 wells microplate, 25 µl of the serial dilutions were pipetted in the wells. Each microplate was prepared in duplicate. The overnight bacterial cultures were diluted in fresh 2×TY-medium to a final $OD^{600}$ of 0.01. To each well, 150 µl of the diluted bacterial cultures was added. The microplates were covered with a lid, and incubated overnight at 25° C. and the duplicate microplate at 37° C.

After 16 hours of incubation, the $OD^{600}$ was read in a microplate reader. From the results, the concentration of amoxicillin still allowing uninhibited growth of the test microorganisms can be read.

TABLE 3

Concentration of amoxicillin still allowing uninhibited growth in 2xTY medium

| Strain | [Amoxicillin] (mg/l) at 25° C. | [Amoxicillin] (mg/l) at 37° C. |
|---|---|---|
| *Escherichia coli* ESS (DS10031) | 0.1 | 0.1 |
| *Bacillus subtilis* ATCC6633 | 1.0 | 5 |
| *Micrococcus luteus* ATCC9341 | 0.001 | 0.002 |

Example 11

Development of a Bioassay Allowing the Detection of the Conversion of DLD-PgCV to Ampicillin The bacterial strains *Escherichia coli* ESS, *Bacillus subtilis* ATCC6633 and *Micrococcus luteus* ATCC9341 were grown overnight in 2×TY-medium at 30° C. and 280 rpm. After 16 hours of growth, the $OD^{600}$ was measured. Typically, the $OD^{600}$ amounts 5.0, ranging from 2.0 to 8.0.

A solution of ampicillin was made at a concentration of 7 mg/ml. Subsequently, serial dilutions were made ranging from 1 mg/l down to 0.001 mg/l. MilliQ water served as a negative control.

In a 96 wells microplate, 25 µl of the serial dilutions were pipetted in the wells. Each microplate was prepared in duplicate. The overnight bacterial cultures were diluted in fresh 2×TY-medium to a final $OD^{600}$ of 0.01. To each well, 150 µl of the diluted bacterial cultures was added. The microplates were covered with a gas permeable adhesive seal, and incubated overnight at 25° C. and the duplicate microplate at 37° C.

After 16 hours of incubation, the $OD^{600}$ was read in a microplate reader. From the results, the concentration of ampicillin still allowing uninhibited growth of the test microorganisms can be read.

TABLE 4

Concentration of ampicillin still allowing uninhibited growth in 2xTY medium

| Strain | [Ampicillin] (mg/l) at 25° C. | [Ampicillin] (mg/l) at 37° C. |
|---|---|---|
| *Escherichia coli* ESS (DS10031) | 0.05 | 0.05 |
| *Bacillus subtilis* ATCC6633 | 0.5 | 2.5 |
| *Micrococcus luteus* ATCC9341 | 0.001 | 0.002 |

Example 12

Screening of pcbC-Genes from Different Genera for the In Vitro Conversion of DLD-HpgCV to Amoxicillin The coding regions of pcbC-genes from 11 species were ordered at DNA 2.0 (1430 O'Brien Drive, Suite E, Menlo Park, Calif. 94025, USA). To this end, the DNA sequence of the coding region was taken as a basis. The following species were selected: *Cephalosporium Acremonium, Penicillium chrysogenum, Aspergillus (Emericella) nidulans, Streptomyces jumonjinensis, Nocardia lactamdurans, Streptomyces microflavis, Lysobacter lactamgenus, Flavobacterium* species, *Streptomyces clavuligerus, Streptomyces griseus, Streptomyces cattleya*.

The sequence of the start-codon was changed to CATATG, the recoginition site of NdeI, in order to facilitate future cloning steps. Likewise, a NsiI-site (ATGCAT) was introduced immediately behind the stop-codon. Internal NsiI- and NdeI-sites were removed as much as possible.

The plasmids carrying the pcbC-genes were cut with NsiI and NdeI and the coding region of the pcbC-gene was isolated and subcloned into vector pSJ127, which was cut with the same enzymes. In this way, the coding region of the pcbC-gene is cloned in frame with the malE-gene encoding maltose binding protein, under control of an inducible promoter. Upon induction of expression, a fusion protein will be synthesized consisting of the maltose binding protein at the N-terminus of the fusion protein and IPNS at the C-terminus.

*E. coli* TOP10, transformed with the ma/E-pcbC-plasmids, were grown in 2×TY-medium containing 35 µg chloroamphenicol/ml, overnight at 37° C. and 280 rpm. The next day, the $OD^{600}$ was measured and cells were diluted in fresh medium to a final $OD^{600}$ of 0.015. The cells were grown further (37° C., 280 rpm) until the $OD^{600}$ reached a value of 0.4-0.6. IPTG was added to a final concentration of 0.5 mM. Growth was proceeded at 22° C., 280 rpm overnight. Cells were harvested by centrifugation for 10 minutes at 5000 rpm and 4° C. Cells were washed with a 0.9% NaCl-solution, and pelleted again by centrifugation. The cell pellets were frozen at −20° C. for at least 16 hours.

Cell pellets were resuspended in 1.5 ml extraction buffer (50 mM Tris.HCl pH 7.5; 5 mM DTT) and extracts were made by sonification. The extracts were centrifuged in order to remove cellular debris in an Eppendorf centrifuge (10 minutes, 14000 rpm, 4° C.). The supernatant (cell free extract, CFE) was aliquoted into fresh Eppendorf tubes and frozen in liquid nitrogen, and subsequently stored at −80° C.

The conversion of HpgCV to amoxicillin was assayed as follows. Firstly, the substrate HpgCV was reduced by mixing 500 µl of 200 mM HpgCV and 500 µl 20 mM TCEP, followed by incubation at 25° C. for 10 minutes. Secondly, the following assay mixture was made (for 10 reactions): 300 µl 0.5 mM $FeSO_4.7H_2O$; 480 µl 1.25 mM ascorbate; 4270 µl 50 mM HEPES (pH 7.0). The assay was started by mixing 90 µl reduced substrate, 505 µl assay mixture and 5 µl of the CFE, containing the MBP-IPNS fusion protein.

The reaction mixture was incubated at 25° C. for 10 minutes.

25 µl of the reaction mixture was mixed with 150 µl of a diluted overnight culture of *Micrococcus luteus* in 2×TY ($OD^{600}$=0.01), in a microplate. In order to verify that any possible inhibition of growth was caused by the formation of amoxicillin, each sample was also tested in the presence of β-lactamase (Penase® from BBL Difco), which cleaves the β-lactam ring and thereby inactivates the antibiotic activity.

The microplate was covered with a lid and incubated overnight at 30° C. and 550 rpm. The $OD^{600}$ was read on a microplate reader.

Surprisingly, the MBP-IPNS fusion proteins originating from the pcbC-genes from *A. nidulans* as well as from *S. clavuligerus* both showed inhibition of the growth of *M. luteus*, which was grown fully in the presence of Penase®, indicating that the inhibition was due to the formation of amoxicillin from DLD-HpgCV.

This was confirmed by LC-MS/MS analysis. To this end, the reaction was stopped by adding 125 µl reaction mixture with 50 µl methanol (−20° C.). The samples were incubated for at least 1 hour at −20° C. A centrifugation step (14000 rpm for 15 minutes at 4° C.) was performed, followed by LC-MS/MS analysis (see Example 9). The results confirmed the results of the bio-assay.

As a control, LLD-ACV was included. Indeed, as expected, almost all MBP-IPNS fusion proteins formed IPN (isopenicillinN). Addition of Penase® to the reaction mixture deleted the observed effect. Again, the results were confirmed by LC-MS/MS.

Example 13

Engineering pcbC-Genes

The clones pSJ-AnIPNS (pcbc-gene from *A. nidulans*) and pSJ-ScIPNS (pcbc-gene from *S. clavuligerus*) were subjected to error prone PCR (EP-PCR) using the Diversify PCR kit from Clontech according to the guidelines of the supplier. In short, the number of errors introduced by PCR can be modified by applying different PCR conditions.

The amplified pcbC-inserts were subcloned into the expression vector pBADMHmalEDEST, using the restriction enzymes NdeI and NsiI. Also in this plasmid, IPNS will be produced as an MBP fusion protein.

Of each condition applied, 10 clones were sequenced. The libraries in which a mutation rate of approximately 1 mutation per kb was found were selected for the screening for improved variants with respect to the conversion of HpgCV into amoxicillin.

The selected *A. nidulans*- and *S. clavuligerus* pcbC libraries were grown, and the insert was subcloned into the expression vector pBADMHmalEDEST, using the restriction enzymes NdeI and NsiI. Also in this plasmid, IPNS will be produced as an MBP fusion protein.

A third library was constructed, in which mutations were introduced at specific positions within the pcbc-gene from *A. nidulans* (site directed approach). These positions were selected on two criteria: a) the creation of space in the active center, and b) weakening the C-terminus binding.

The creation of space in the active center may be beneficial for improving the activity of the native IPNS on HpgCV, since the Hpg-moiety is larger than the α-aminoadipate-moiety in ACV.

The C-terminus of the IPNS molecule acts as a quasi-substrate when the enzyme is not loaded with a substrate. Upon the approach of the substrate to the active center, the C-terminus withdraws, creating space for the substrate. In order to prevent this competition between C-terminus and substrate, alterations were introduced here as well.

Eight amino acid positions were selected for modification: I75, Y91, S183, V185, N287, L321, L324 and T331.

Primers were designed, 33-mers, in which the three middle nucleotides (encoding the amino acid to be modified) were randomized (NNN), thus creating the possibility for any amino acid to be present in the resulting IPNS molecule at the indicated positions.

All eight positions were thus modified by fusion PCR, resulting in eight sub-libraries, each with single site mutations. One additional library was made in which all the mutations were combined in a random fashion.

Also in this case, the inserts of the thus obtained library was subcloned in the expression vector pBADMHmalEDEST, using the restriction enzymes NdeI and NsiI.

The three libraries were plated from glycerol stocks on selective agar-medium, containing 50 µg zeocin per ml. Of each EP-PCR library, 2500 independent clones were picked and used to inoculate 150 µl 2×TY-medium containing 50 µg zeocin per ml, in 96 wells plates. Of the site directed library, 200 clones were picked from each sub-library for inoculation of 150 µl 2×TY-medium containing 50 µg zeocin per ml, in 96 wells plates.

After growth overnight at 37° C. and 280 rpm, 5 µl of the confluent cultures was transferred to 1 ml fresh 2×TY-medium containing 50 µg zeocin per ml, in a deepwell microplate. Growth was allowed at 37° C. and 280 rpm, until the $OD^{600}$ reached a value between 0.4 and 0.6, on average across the microplate. Cells were induced to produce the MBP-IPNS fusion protein by the addition of 40 µl 5% L-arabinose to each of the individual wells. Subsequently, the cells were grown for 24 hours at 22° C. and 220 rpm.

Cells were harvested by centrifugation. The supernatant was discarded and the cell pellets were frozen overnight at −20° C.

To each well, containing a cell pellet, 100 µl Lysis Buffer (50 mM HEPES pH 7.0; 0.5 mg/ml lysozyme; 0.1 mg/ml DNAseI; 5 mM DTT; 5 mM MgSO4) was added, followed by an incubation at room temperature for 30 minutes.

The microplates were spun, and 50 µl of the supernatant was transferred to a fresh microplate. 50 µl assay-mix (50 mM HEPES pH 7.0; 1 mM TCEP; 100 µM Na-ascorbate; 25 µM Fe-sulfate; 5 mM HpgCV) was added to the supernatant, followed by an incubation for 30 minutes at 25° C. 125 µl of a diluted *M. luteus*-culture in 2×TY (final $OD^{600}$ is 0.01) was added. The plate was incubated overnight at 30° C. The $OD^{600}$ was read using a microplate reader.

18 clones, 16 originating from the V185 sub-library and 2 from the recombined sub-library were selected from the site directed *A. nidulans* library. All these clones showed a complete inhibition of the growth of *M. luteus*, indicating that a compound was formed inhibiting the growth of the indicator strain. This inhibition was retested according to the above protocol, and again positive. Moreover, the inhibition was absent upon the addition of Penase®, indicating that the inhibitory compound is a β-lactam.

The positive clones were grown in 10 ml 2×TY with 50 μg zeocin per ml. As a control source of IPNS, pBAD-AnpcbC was included in the assay. After overnight growth at 37° C. and 280 rpm, the $OD^{600}$ was determined. 100 ml 2×TY medium containing 50 μg zeocin per ml was inoculated to an initial $OD^{600}$ of 0.015. The cells were grown at 37° C. and 280 rpm until the $OD^{600}$ reached a value of 0.4 to 0.6. Production of the fusion protein MBP-IPNS was induced by the addition of L-arabinose to a final concentration of 0.2%. Growth was maintained at 22° C. and 220 rpm, overnight. Cells were harvested and washed and frozen at −20° C. overnight. Cell lysates were prepared by the addition of 1.5 ml Lysis Buffer (50 mM HEPES pH 7.0; 0.5 mg/ml lysozyme; 0.1 mg/ml DNAseI; 5 mM DTT; 5 mM MgSO4), followed by an incubation at room temperature for 30 minutes. The extract was centrifuged and the supernatant (CFE) was pipetted to a fresh tube.

Two Bioassays Were Done:

1) A liquid bio-assay: 8 μl of the CFE was mixed with 592 μl of assay mix (50 mM HEPES pH 7.0; 1 mM TCEP; 100 μM Na-ascorbate; 25 μM Fe-sulfate; 5 mM HpgCV). After incubation for 10 minutes at 25° C., 125 μl of a diluted *M. luteus*-culture in 2×TY (final $OD^{600}$ is 0.01) was added. As control substrates, ACV was used (both LLD- and DLD-PgCV may be used, although DLD-PgCV is the preferred substrate). In addition, for each sample an extra control was included, in which Penase® was added to the assay-mix. After overnight growth at 30° C., the $OD^{600}$ was read.

2) A bio-assay on agar-plates: 8 μl of the CFE was mixed with 592 μl of assay mix (50 mM HEPES pH 7.0; 1 mM TCEP; 100 μM Na-ascorbate; 25 μM Fe-sulfate; 5 mM HpgCV). After incubation for 10 minutes at 25° C., 50 μl of the assay-mix was spotted in an agar-plate in which wholes were made. Of each sample an extra control was included, in which Penase® was added to the assay-mix. The agar consisted of 2×TY-agar supplemented with *M. luteus* to a final $OD^{600}$ of 0.01. After overnight incubation at 30° C., the presence or absence of cleared zones, due to the action of β-lactams, was scored.

Table 5 shows an overview of the activity of some of the mutants. Each mutant represents a larger group of mutants having a comparable IPNS activity on HpgCV as a substrate. The activity of the wild type IPNS enzymes from *A. nidulans* en *S. clavuligerus* was below the detection limit in these screening assays.

TABLE 5

Overview of the bioassays on the IPNS activity of the selected clones and controls.

| | | Liquid bio-assay | | Agar bio-assay | |
|---|---|---|---|---|---|
| Clone | Substrate | As such | With Penase ® | As such | With Penase ® |
| 35A12 | HpgCV | + | − | + | − |
| 35F1 | HpgCV | + | − | + | − |
| 36A4 | HpgCV | + | − | + | − |
| 36F3 | HpgCV | + | − | + | − |
| 36C4 | HpgCV | + | − | + | − |
| Wt A. nid. | HpgCV | − | − | − | − |
| Wt S. cla | HpgCV | − | − | − | − |
| 35A12 | ACV | + | − | + | − |
| 36F3 | ACV | + | − | + | − |
| Wt A. nid. | ACV | + | − | + | − |
| 35A12 | PgCV | + | − | + | − |
| 36F3 | PgCV | + | − | + | − |
| Wt A. nid. | PgCV | − | − | − | − |

All the positive clones in the screening were subjected to sequence analysis and representative clones were subjected to LC/MS analysis. LC/MS analysis was performed allowing the identification of the formed products based on retention time, the mass of the compound and the fragmentation pattern of the product. The amount of amoxicillin that is produced was determined by the standard addition method and is expressed in AU/mg protein, wherein AU represents the amount of amoxicillin (in ng) formed in 10 minutes under the specified reaction conditions. Table 6 summarizes the clones, the changed amino acid residues and the activity of the clones on HpgCV (in AU amoxicillin/mg protein in the *E. coli* CFE).

TABLE 6

Overview of the mutations and activity on HpcCV of the active IPNS mutants

| | Activity | Position in *A. nidulans* IPNS | | | | | | |
|---|---|---|---|---|---|---|---|---|
| Mutant | (AU/mg protein) | 111 | 135 | 185 | 190 | 211 | 293 | 331 |
| 36A4 | 1120 | | | V185R | | | | |
| 35A12 | 90 | | | V185K | | | | |
| 35F1 | 130 | | | V185K | | | V293A | |
| 36F3 | 50 | T111A | H135R | V185R | | | | |
| 35H12 | 30 | | | V185K | P190H | | | |
| 36C4 | n.d. | | | V185H | | | | T331C |
| wt | n.d. | | | | | | | | n.d. = not detectable

Example 14

Conversion of DLD-PgCV to Ampicillin

The activity of the mutant pcbC-clones 36A4 (V185R), 35A12 (V185K), 35F1 (V185K, V293A), 36F3 (T111A, H135R, V185R), 35H12 (V185K, P190H), 36C4 (V185H, T331C) and the wild-type pcbC-gene from *A. nidulans* was determined on DLD-PgCV as a substrate. To this end, the clones were cultured in 10 ml 2×TY with 50 μg zeocin per ml. After overnight growth at 37° C. and 280 rpm, the $OD^{600}$ was determined. 100 ml 2×TY medium containing 50 μg zeocin per ml was inoculated to an initial OD$^{600}$ of 0.015. The cells were grown at 37° C. and 280 rpm until the OD$^{600}$ reached a value of 0.4 to 0.6. Production of the fusion protein MBP-IPNS was induced by the addition of L-arabinose to a final concentration of 0.2%. Growth was maintained at 22° C. and 220 rpm, overnight. Cells were harvested and washed and frozen at −20° C. overnight. Cell lysates were prepared by the addition of 1.5 ml Lysis Buffer (50 mM HEPES pH 7.0; 0.5 mg/ml lysozyme; 0.1 mg/ml DNAseI; 5 mM DTT; 5 mM MgSO4), followed by an incubation at room temperature for 30 minutes. The extract was centrifuged and the supernatant (CFE) was pipetted to a fresh tube.

8 μl of the CFE was mixed with 592 μl of assay mix (50 mM HEPES pH 7.0; 1 mM TCEP; 100 μM Na-ascorbate; 25 μM Fe-sulfate; 5 mM PgCV). After incubation for 10 minutes at 25° C., 100 μl of a diluted *M. luteus*-culture in 2×TY (final OD$^{600}$ is 0.01) was added to 50μl of the reaction mixture. As a control substrate, ACV was used. In addition, for each sample an extra control was included, in which Penase® was added to the assay-mix. After overnight growth at 30° C., the OD$^{600}$ was read. All samples, even the wild-type *A. nidulans* IPNS fusion protein to MBP, resulted surprisingly in inhibition of growth of *M. luteus*.

LC/MS analysis was performed on these samples, allowing the identification of the formed products based on retention time, the mass of the compound and the fragmentation pattern of the product. The amount of ampicillin that was produced was determined by the standard addition method. In table 7, the activity on PgCV has been summarized.

TABLE 7

Activity of the mutant and wild-type MBP-IPNS fusion proteins on PgCV (in ng product per mg total protein, per 10 minutes) as determined by LC-MS analysis

| Mutant | Activity (AU/mg protein) | 111 | 135 | 185 | 190 | 211 | 293 | 331 |
|---|---|---|---|---|---|---|---|---|
| 36A4 | 900 | | | V185R | | | | |
| 35A12 | 150 | | | V185K | | | | |
| 35F1 | 150 | | | V185K | | | V293A | |
| 36F3 | 30 | T111A | H135R | V185R | | | | |
| 35H12 | 50 | | | V185K | P190H | | | |
| 36C4 | 1 | | | V185H | | | | T331C |
| w.t. | 1 | | | | | | | |

Example 15

Construction of a *Penicillium* Strain Producing D-Hpg or L-Hpg

15a Construction of *Penicillium* Expression Plasmids

The genes of the hydroxymandelate synthase from *Amycolatopsis orientalis* and *Streptomyces coelicolor* (hmaS), and the genes encoding hydroxyphenylglycine aminotransferase (hpgAT from *Pseudomonas putida* and hpgT from *Streptomyces coelicolor* respectively) were cloned in plasmid pIPCLTA by PCR amplification of these genes from the different corresponding pBAD plasmids described in WO 02/34921. The gene mdlB, encoding mandelate dehydrogenase from *Pseudomonas putida*, was amplified from pGEM-Bldm. The insertion in the NdeI and NsiI sites of of pIPCLTA was chosen, leading to an ATG fusion of the appropriate gene with the *Penicillium* promoter. All genes were amplified by PCR, and the amplification primers were constructed by introducing a NdeI restriction site in the upstream primer and a NsiI restriction site in the downstream primer. Because the genes hpgAT from *Pseudomonas putida* contains an internal NsiI-site, an alternative approach was carried out, in which the insert was amplified using primers which introduced NdeI- and BsaI-sites. The PCR fragment with the additional NdeI/BsaI sites was subcloned as a blunt end fragment in the cloning vector pCR-blunt-TOPO (Invitrogen) leading to the construction of pCR-bl-hpgAT$_{Pp}$. After sequence determination revealed that it contained the correct insert including the flanking NdeI/BsaI sites, this plasmid was used for the construction of pIPphpgATgWA by cloning the NdeI/BsaI fragment containing the hpgAT$_{Pp}$ gene in the NdeI/Ppu10I site of pIPCLTA.

In pIPCLTA, the genes introduced in this vector are under control of the pcbC-promoter of *Penicillium chrysogenum*. In addition, the transcription terminator of the penDE-gene, encoding acyltransferase, has been used in these constructs. The Following Expression Cassettes Were Constructed:

| Expression vector | Gene | Encoded protein | Promoter | Terminator |
|---|---|---|---|---|
| plAohmaSgWA | Ao-hmaS | p-hydroxymandelate synthase | pcbC | penDE |
| plScohmaSgWA | Sco-hmaS | p-hydroxymandelate synthase | pcbC | penDE |
| plPpmdlBgWA | Pp-mdlB | L-mandelate dehydrogenase | pcbC | penDE |
| plPphpgATgWA | Pp-hpgAT | L-p-hydroxyphenylglycine aminotransferase | pcbC | penDE |
| plScohpgTgWA | Sco-hpgT | L-p-hydroxyphenylglycine aminotransferase | pcbC | penDE |

The following primers were used in the cloning amplification of the genes mentioned above:

```
A: Amycolatopsis orientalis genes
Construction of plAohmaSgWA
hmaS-Ao-Nde:
                                     (SEQ ID NO: 28)
5'-CAGGAGGAATTACATATGCAGAATTTCGAG
hmaS-Ao-Nsi:
                                     (SEQ ID NO: 29)
5'-CGGCCAGGGATGCATACGTCATCGCCGAGC B: Streptomyces coelicolor genes
Construction of plScohmaSgWA
hmaS-Sc-Nde:
                                     (SEQ ID NO: 30)
5'-CAGGAGGAATTACATATGCCGCCCAGTGAC
hmaS-Sc-Nsi:
                                     (SEQ ID NO: 31)
5'-GAATTCCCATATGCATCCAGGTCATCGGCC
Construction of plScohpgTgWA
hpgT-Sc-Nde:
                                     (SEQ ID NO: 32)
5'-CAGGAGGAATTACATATGACCACCACCACC
hpgT-Sc-Nsi:
                                     (SEQ ID NO: 33)
5'-TCCCATATGCATCCTCAACCGTTAGACGCC C: Pseudomonas putida genes
Construction of plPpmdlBgWA
hpgT-Sc-Nde:
                                     (SEQ ID NO: 34)
5'-GTGAGGTAACATATGAGCCAGAATCTCTTT
hpgT-Sc-Nsi:
                                     (SEQ ID NO: 35)
5'-GTAATCAATGCATCACTCATGCGTGTGTTC
Construction of plPphpgA TgWA
hpgAT-Nde
                                     (SEQ ID NO: 36)
5'-CAGGAGGAATTACATATGTCTATTTATAGC
hpgAT-BsaI
                                     (SEQ ID NO: 37)
5'-GTCCTCGGTCTCATGCAT CTCGAGTTAGCCCAGGAGGT
```

15b Transformation of Pencillium Chrysogenum

The plasmids plAohmaSgWA, plScohmaSgWA, plPpmdlBgWA, plPphpgATgWA and plScohpgTgWA were cut with NotI, which excises the expression cassette from the vector.

Penicillium chrysogenum DS12975, an industrial penicillin-producing strain from DSM, was transformed with 4 µg of DNA (i.e. the NotI-digests) and 0.25 µg of a selection marker fragment. In this case, a fragment was used which confers resistance to phleomycin.

The Following Combinations of Expression Cassettes Were Transformed:

| Transformation | Gene 1 | Gene 2 | Gene 3 |
|---|---|---|---|
| 1 | Sc-hmaS | Pp-mdlB | Pp-hpgAT |
| 2 | Ao-hmaS | Pp-mdlB | Pp-hpgAT |
| 3 | Sc-hmaS | Pp-mdlB | Sc-hpgT |
| 4 | Ao-hmaS | Pp-mdlB | Sc-hpgT |

Selection of transformants was done on mineral medium agar plates with 1 gram per liter and 1 M *saccharose*. Phleomycin resistant colonies appearing upon protoplast regeneration were re-streaked on fresh phleomycin agar plates without saccharose and grown until sporulation.

Transformants were streaked on the same medium and integration of the expression cassettes was verified by PCR, using specific primers for the individual genes.

Transformants containing the three intended genes were streaked on agar slant tubes and sporulated on rice.

The Following Strains Were Selected for Further Analysis:

| Strain | Genes integrated into the genome |
|---|---|
| AFF108 | Ao-hmaS, Pp-mdlB, Pp-hpgAT |
| AFF133 | Ao-hmaS, Pp-mdlB, Pp-hpgAT |
| AFF146 | Sc-hmaS, Pp-mdlB, Pp-hpgAT |
| AFF152 | Sc-hmaS, Pp-mdlB, Pp-hpgAT |
| AFF158 | Ao-hmaS, Pp-mdlB, Sc-hpgT |
| AFF162 | Ao-hmaS, Pp-mdlB, Sc-hpgT |
| AFF164 | Ao-hmaS, Pp-mdlB, Sc-hpgT |
| AFF191 | Sc-hmaS, Pp-mdlB, Sc-hpgT |
| AFF193 | Sc-hmaS, Pp-mdlB, Sc-hpgT |
| AFF195 | Sc-hmaS, Pp-mdlB, Sc-hpgT |

15c Fermentative Production of D-Hpg by *Penicillium* Transformants

*Penicillium chrysogenum* transformants AFF108, AFF133, AFF146 and AFF152 were cultivated on shake flasks for 6 days. Intracellular and extracellular products were determined by NMR.

TABLE 8

Intracellular D-Hpg concentrations detected by NMR.
Cells were grown for 3 to 6 days.

| Strain | D-Hpg (µg/g dry weight) | |
|---|---|---|
|  | Day 3 | Day 4-6 |
| DS12975 | 0 | 0 |
| AFF108 | 40 | 0 |
| AFF133 | 80 | 0 |
| AFF146 | 40 | 0 |
| AFF152 | 40 | 0 |

Cells were grown for 3, 4, 5, and 6 days to find an optimum for D-Hpg production. The concentration after 3 days was high enough to detect peaks in the NMR spectrum and to quantify the D-Hpg content. All selected transformants produced detectable levels of D-Hpg but the highest D-Hpg concentration was observed in AFF133 (80 μg/g DW). The results are listed in table 8.

15d Fermentative Production of L-Hpg by *Penicillium* Transformants

*Penicillium chrysogenum* strains AFF158, AFF162, AFF164, AFF191, AFF193 and AFF195, containing the L-Hpg biosynthesis genes, were cultivated on shake flasks for 3, 4, 5 and 6 days. Intracellular and extracellular products were determined by NMR. Again, no extracellular product could be detected but intracellularly, substantial levels of L-Hpg were perceived (see table 9).

The intracellular L-Hpg levels could be quantified for all strains and are listed in table 6. Unlike the D-Hpg levels, the L-Hpg levels increased in time and reached an optimum around 5 or 6 days of growth. In AFF195 mycelium the highest concentration was measured which was 2,6 mg L-Hpg per gram dry weight. The L-Hpg producing strains gained an approx. 30 times higher intracellular concentration than the AFF133, the highest D-Hpg producer.

TABLE 9

Intracellular L-Hpg concentrations detected by NMR.

| | L-Hpg (μg per gram dry weight) | | | |
|---|---|---|---|---|
| Strain | Day 3 | Day 4 | Day 5 | Day 6 |
| DS12975 | 0 | 0 | 0 | 0 |
| AFF158 | 360 | 340 | 180 | 380 |
| AFF162 | 740 | 880 | 940 | 2200 |
| AFF164 | 1160 | 1020 | 960 | 1880 |
| AFF191 | 620 | 860 | 860 | 2060 |
| AFF193 | 600 | 680 | 1600 | 740 |
| AFF195 | 740 | 680 | 1040 | 2640 |

In a next experiment the cells were cultivated for 5, 6 and 7 days however, after 5 or 6 days the L-Hpg concentration did not increase further but started to decrease (data not shown).

Example 16

Fermentative Production of Amoxicillin by *P. Chrysogenum*

A *Pencillium chrysogenum* strain devoid of the penicillin biosynthetic clusters as discribed in patent application PCT/EP2007/054045 was transformed with combinations of 1) the plasmid pEXPR-NRPS6 (see table 1) harbouring an NRPS-gene encoding HpgCVS (DLD-Hpg-Cys-Val Synthetase), 2) a plasmid harbouring the gene encoding the IPNS mutant V185R and 3) a plasmid harbouring the gsp-gene from *Bacillus brevis*, encoding a Ppant-transferase (PPT), under control of the gpdA-promoter.

Selection of transformants was done on mineral medium agar plates with 50 μg phleomycin per ml and 1 M saccharose. Phleomycin resistant colonies appearing upon protoplast regeneration were re-streaked on fresh phleomycin agar plates without saccharose and grown until sporulation.

Of each transformation about 100 colonies were grown on mineral medium. Additionally, the amino acid L-Hpg was added at a concentration varying from 1 mM to 10 mM. Cultivation was carried out on shake flask scale or in 24-well microtiter plates. Incubation was done at 25° C. for one week at 200 rpm.

At several time points (4 days tot 7 days), samples were taken. The broth was centrifuged in order to remove the mycelium. A total broth sample was removed and freeze-dried. Both the freeze-dried broth sample and the supernatant were analyzed for the presence of amoxicillin.

In case of the supernatant, 10 and 50 μl of the supernatant was added to 190 and 150 μl respectively of a diluted *M. luteus* culture, as described in example 2. As a control, Penase® was added to the sample, which degrades amoxicillin. Several transformants showed an inhibition of growth of *M. luteus*, indicating the action of amoxicillin produced by the transformant. The addition of Penase® prevented the inhibition of growth of *M. luteus*.

The freeze-dried broth samples were treated with 100-500 μl of hot milliQ water (90° C.; volume depending on the amount of biomass), in order to make a lysate. 10 μl and 50 μl of the lysate were mixed with 150 μl and 190 μl of a diluted *M. luteus* culture respectively, as described above. A Penase® control was added as well. Also in this case, several samples did inhibit the growth of *M. luteus*. The positive extracts corresponded to the supernatant samples. The identity of the β-lactam that was formed was confirmed to be amoxicillin by LC/MS/MS, as described in example 9.

The invention claimed is:

1. An isolated non-ribosomal peptide synthetase (NRPS) that catalyses formation of the tripeptide hydroxyphenylglycyl-cysteinyl-valine or the tripeptide phenylglycyl-cysteinyl-valine from hydroxyphenylglycine, cysteine and valine or from phenylglycine, cysteine and valine, respectively, the NRPS comprising (i) a first module M1 specific for hydroxyphenylglycine or phenylglycine comprising SEQ ID NO: 2 or SEQ ID NO: 4 or, where the first module M1 is specific for hydroxyphenylglycine the first module M1 comprises a sequence additionally selected from the sixth module of a Calcium-Dependent Antibiotic (CDA) synthetase of a *Streptomyces* coelicolor or the fourth module of a *Chloroerenomycin* Synthetase of a *Amycolatopsis* orientalis or the fifth module of a *Chloroerenomycin* Synthetase of a *Amycolatopsis* orientalis, or the seventh module of a *Complestatin* Synthetase of a *Streptomyces* lavendulae, and where the first module M1 is specific for phenylglycine the first module M1 comprises a sequence additionally selected from a C-terminal module of a SnbD protein of a *Pristinamycin* Synthetase of a *Streptomyces pristinaspirali*, (ii) a second module M2 specific for cysteine comprises SEQ ID NO: 6 or SEQ ID NO: 8 or a second module of an δ-(L-α-aminoadipyl)-L-cysteinyl-D-valine synthetase of a Nocardia lactamdurans or a second module of an δ-(L-α-aminoadipyl)-L-cysteinyl-D-valine synthetase of a *Penicillium chrysogenum* or a second module of an δ-(L-α-aminoadipyl)-L-cysteinyl-D-valine synthetase of an *Acremonium chrysogenum* or a second module of an δ-(L-α-aminoadipyl)-L-cysteinyl-D-valine synthetase of an *Aspergillus nidulans* or a domain of the second module of *Bacillus subtilis* RB14 Iturin Synthetase Protein ItuC, or an amino acid sequence of *Penicllium chrysogenum* enabling incorporation of the amino acid L-cysteine while being coupled to the amino acid Hpq or Pq, (iii) a third module M3 specific for valine having SEQ ID NO: 10 or a third module of an δ-(L-α-aminoadipyl)-L-cysteinyl-D-valine synthetase of a Nocardia lactamdurans or a third module of an δ-(L-α-aminoadipyl)-L-cysteinyl-D-valine synthetase of a *Penicillium chrysogenum* or a third module of an δ-(L-α-aminoadipyl)-L-cysteinyl-D-valine synthetase of an *Acremonium chrysogenum* or a third module of an δ-(L-α-aminoadipyl)-L-cysteinyl-D-valine synthetase of an *Aspergillus nidulans*, the third module M3 enabling incorporation of the amino acid L-valine to hydroxyphenylglycyl-Cysteine or phenylglycyl-Cysteine.

2. The peptide synthetase of claim 1, wherein the first module M1 specific for hydroxyphenylglycine is obtained from at least one of a Calcium-Dependent Antibiotic Synthetase, a *Chloroerenomycin* Synthetase and a *Complestatin* Synthetase.

3. The peptide synthetase of claim 1, wherein the first module M1 specific for phenylglycine is obtained from a *Pristinamycin* Synthetase.

4. The peptide synthetase of claim 1, wherein the M2 module comprises a condensation domain that is D-specific for the donor and L-specific for the acceptor ($^DC_L$) that is fused to an adenylation domain obtained from the second module of an δ-(L-α-aminoadipyl)-L-cysteinyl-D-valine synthetase (ACVS), wherein the $^{D}C_{L}$ domain is heterologous to the adenylation domain.

5. The peptide synthetase of claim 4, wherein the $^{D}C_{L}$ domain of the module M2 is obtained from the enzyme that is the source of the first module M1.

6. The peptide synthetase of claim 4, wherein the $^{D}C_{L}$ domain of the module M2 is the condensation domain of the seventh module of a Calcium-Dependent Antibiotic Synthetase.

7. The peptide synthetase of claim 4, wherein the $^{D}C_{L}$ domain of the module M2 is the condensation domain of the second module of an Iturin Synthetase.

8. The peptide synthetase of claim 1, further comprising adenylation and thiolation domains of the M2 module and the complete M3 module are obtained from an ACVS, preferably a bacterial or fungal ACVS.

* * * * *